United States Patent
Carling et al.

(10) Patent No.: US 6,476,030 B1
(45) Date of Patent: Nov. 5, 2002

(54) PYRAZOLO-TRIAZINE DERIVATIVES AS LIGANDS FOR GABA RECEPTORS

(75) Inventors: William Robert Carling, Bishops Storford (GB); Andrew Mitchinson, Sawbridgeworth (GB); Kevin William Moore, Buntingford (GB); Michael Geoffrey Russell, Welwyn Garden City (GB); Gayle Scott, Lanark (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/806,879

(22) PCT Filed: Oct. 13, 1999

(86) PCT No.: PCT/GB99/03401

§ 371 (c)(1),
(2), (4) Date: Jun. 8, 2001

(87) PCT Pub. No.: WO00/23449

PCT Pub. Date: Apr. 27, 2000

(30) Foreign Application Priority Data

Oct. 16, 1998 (GB) ............................................. 9822716
Aug. 25, 1999 (GB) ............................................. 9920092

(51) Int. Cl.[7] ................... C07D 487/04; A61K 31/5365
(52) U.S. Cl. ................. 514/243; 514/232.5; 514/233.2; 514/228.5; 544/184; 544/112; 544/81; 544/61
(58) Field of Search ................... 544/184, 112, 544/81, 61; 514/243, 232.5, 233.2, 228.5

(56) References Cited

FOREIGN PATENT DOCUMENTS

| WO | WO 95/10521 | 4/1995 |
|----|----|----|
| WO | WO 98/04559 | 2/1998 |
| WO | WO 98/04560 | 2/1998 |
| WO | WO 99/00391 | 1/1999 |
| WO | WO 99/36423 | 7/1999 |

OTHER PUBLICATIONS

K. A. Wafford et al., Mol. Pharmacol., 50:670–678(1996).
G. R. Dawson et al., Psychopharmacology, 121:109–117(1995).
P. J. Bayley et al., J. Psychopharmacol., 10:206–213(1996).
L. J. Bristow et al., J. Pharmacol. Exp. Ther., 279:492–501(1996).

*Primary Examiner*—John M. Ford
(74) *Attorney, Agent, or Firm*—J. Eric Thies; Melvin Winokur

(57) ABSTRACT

Compounds according to Formula (I):

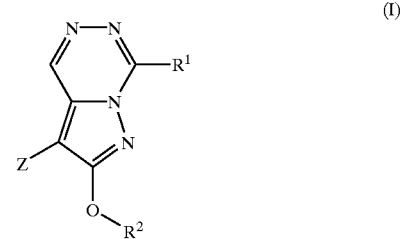

or a salt or prodrug thereof, have good affinity as ligands for the alpha2 and/or alpha3 subunit of the human $GABA_A$ receptor and are useful for treatment of disorders of the central nervous system, including anxiety and convulsions.

9 Claims, No Drawings

PYRAZOLO-TRIAZINE DERIVATIVES AS LIGANDS FOR GABA RECEPTORS

This is an application under 35 U.S.C. 371 of PCT/GB99/03401 and claims priority from Great Britain Patent Application No. GB 9822716.8, filed Oct. 16, 1998 and Great Britain Patent Application No. GB9920092.5, filed Aug. 25, 1999.

The present invention relates to a class of substituted pyrazolotriazine derivatives and to their use in therapy. More particularly, this invention is concerned with substituted pyrazolo[1,5-d][1,2,4]triazine derivatives which are ligands for GABA$_A$ receptors and are therefore useful in the therapy of deleterious mental states.

Receptors for the major inhibitory neurotransmitter, gamma-aminobutyric acid (GABA), are divided into two main classes: (1) GABA$_A$ receptors, which are members of the ligand-gated ion channel superfamily; and (2) GABA$_B$ receptors, which may be members of the G-protein linked receptor superfamily. Since the first cDNAs encoding individual GABA$_A$ receptor subunits were cloned the number of known members of the mammalian family has grown to include at least six α subunits, four β subunits, three γ subunits, one δ subunit, one ε subunit and two ρ subunits.

Although knowledge of the diversity of the GABA$_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional GABA$_A$ receptor expressed by transiently transfecting cDNAs into cells. As indicated above, δ, ε and ρ subunits also exist, but are present only to a minor extent in GABA$_A$ receptor populations.

Studies of receptor size and visualisation by electron microscopy conclude that, like other members of the ligand-gated ion channel family, the native GABA$_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and are thought to account for over 40% of GABA$_A$ receptors in the rat. Subtype assemblies containing α2 and α3 subunits respectively are thought to account for about 25% and 17% of GABA$_A$ receptors in the rat. Subtype assemblies containing an α5 subunit are expressed predominantly in the hippocampus and cortex and are thought to represent about 4% of GABA$_A$ receptors in the rat.

A characteristic property of all known GABA$_A$ receptors is the presence of a number of modulatory sites, one of which is the benzodiazepine (BZ) binding site. The BZ binding site is the most explored of the GABA$_A$ receptor modulatory sites, and is the site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BZ1 subtype has been shown to be pharmacologically equivalent to a GABA$_A$ receptor comprising the α1 subunit in combination with a β subunit and γ2. This is the most abundant GABA$_A$ receptor subtype, and is believed to represent almost half of all GABA$_A$ receptors in the brain.

Two other major populations are the α2βγ2 and α3βγ2/3 subtypes. Together these constitute approximately a further 35% of the total GABA$_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. Compounds which are modulators of the benzodiazepine binding site of the GABA$_A$ receptor by acting as BZ agonists are referred to hereinafter as "GABA$_A$ receptor agonists". The α1-selective GABA$_A$ receptor agonists alpidem and zolpidem are clinically prescribed as hypnotic agents, suggesting that at least some of the sedation associated with known anxiolytic drugs which act at the BZ1 binding site is mediated through GABA$_A$ receptors containing the α1 subunit. Accordingly, it is considered that GABA$_A$ receptor agonists which interact more favourably with the α2 and/or α3 subunit than with α1 will be effective in the treatment of anxiety with a reduced propensity to cause sedation. Also, agents which are antagonists or inverse agonists at α1 might be employed to reverse sedation or hypnosis caused by α1 agonists.

SUMMARY OF THE INVENTION

The present invention is directed to compounds according to Formula (I

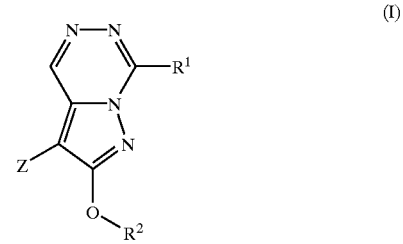

or a salt or prodrug thereof, have good affinity as ligands for the alpha2 and/or alpha3 subunit of the human GABA$_A$ receptor and are useful for treatment of disorders of the central nervous system, including anxiety and convulsions.

DETAILED DESCRIPTION OF THE INVENTION

The compounds of the present invention, being selective ligands for GABA$_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior: to anaesthesia or minor procedures such as endoscopy, including gastric endoscopy.

The present invention provides a class of pyrazolotriazine derivatives which possess desirable binding properties at various $GABA_A$ receptor subtypes. The compounds in accordance with the present invention have good affinity as ligands for the $\alpha 2$ and/or $\alpha 3$ subunit of the human $GABA_A$ receptor. The compounds of this invention may interact more favourably with the $\alpha 2$ and/or $\alpha 3$ subunit than with the $\alpha 1$ subunit. Desirably, the compounds of the invention will exhibit functional selectivity in terms of a selective efficacy for the $\alpha 2$ and/or $\alpha 3$ subunit relative to the $\alpha 1$ subunit.

The compounds of the present invention are $GABA_A$ receptor subtype ligands having a binding affinity ($K_i$) for the $\alpha 2$ and/or $\alpha 3$ subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the $\alpha 2$ and/or $\alpha 3$ subunit relative to the $\alpha 1$ subunit. However, compounds which are not selective in terms of their binding affinity for the $\alpha 2$ and/or $\alpha 3$ subunit relative to the $\alpha 1$ subunit are also encompassed within the scope of the present invention; such compounds will desirably exhibit functional selectivity in terms of a selective efficacy for the $\alpha 2$ and/or $\alpha 3$ subunit relative to the $\alpha 1$ subunit.

The present invention provides a compound of formula I, or a salt or prodrug thereof:

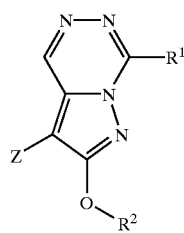

(I)

wherein
Z represents halogen; or $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl or di($C_{1-6}$)alkylamino, any of which groups may be optionally substituted;
$R^1$ represents $C_{3-7}$ cycloalkyl, phenyl, furyl, thienyl, pyridinyl or pyrazinyl, any of which groups may be optionally substituted; and
$R^2$ represents $C_{3-7}$ cycloalkyl($C_{1-6}$)alkyl, aryl($C_{1-6}$)alkyl or heteroaryl($C_{1-6}$)alkyl, any of which groups may be optionally substituted.

The present invention also provides a compound of formula I as depicted above, or a salt or prodrug thereof, wherein
Z represents $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl or di($C_{1-6}$)alkylamino, any of which groups may be optionally substituted;
$R^1$ represents $C_{3-7}$ cycloalkyl, phenyl, furyl, thienyl or pyridinyl, any of which groups may be optionally substituted; and
$R^2$ is as defined above.

The groups Z, $R^1$ and $R^2$ may be unsubstituted, or substituted by one or more substituents, suitably by one, two or three substituents, and more particularly by one or two substituents. In general, the groups Z, $R^1$ and $R^2$ will be unsubstituted or monosubstituted. Examples of optional substituents on the groups Z, $R^1$ and $R^2$ include $C_{1-6}$ alkyl, aryl($C_{1-6}$)alkyl, pyridyl($C_{1-6}$)alkyl, halogen, halo($C_{1-6}$)alkyl, dihalo($C_{1-6}$)alkyl, trifluoromethyl, cyano, cyano($C_{1-6}$)alkyl, hydroxy, hydroxymethyl, $C_{1-6}$ alkoxy, $C_{3-7}$ cycloalkyl($C_{1-6}$)alkoxy, cyano($C_{1-6}$)alkoxy, $C_{3-7}$ cycloalkoxy, amino, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, aryl($C_{1-6}$)alkyl, halogen, cyano, hydroxy, hydroxymethyl, $C_{1-6}$ alkoxy and $C_{3-7}$ cycloalkyl($C_{1-6}$)alkoxy. Typical substituents include $C_{1-6}$ alkyl, halogen, halo($C_{1-6}$)alkyl, dihalo($C_{1-6}$)alkyl, trifluoromethyl, cyano, $C_{1-6}$ alkoxy, cyano($C_{1-6}$)alkoxy, $C_{3-7}$ cycloalkoxy, amino and di($C_{1-6}$)alkylamino($C_{1-6}$)alkyl. Illustrative substituents include $C_{1-6}$ alkyl, halogen and trifluoromethyl, especially $C_{1-6}$ alkyl or halogen. Specific substituents include methyl, ethyl, n-propyl, isopropyl, fluoro, chloro, fluoroethyl, difluoroethyl, trifluoromethyl, cyano, methoxy, ethoxy, cyanomethoxy, cyclobutyloxy, amino and dimethylaminomethyl. Particular substituents include methyl, ethyl, n-propyl, isopropyl, fluoro, choro and trifluoromethyl, especially methyl or fluoro.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical $C_{6-8}$ bicycloalkyl groups include bicyclo[2.1.1] hexyl and bicyclo [2.2.1]heptyl.

Typical aryl groups include phenyl and naphthyl, preferably phenyl.

The expression "aryl($C_{1-6}$)alkyl" as used herein includes benzyl, phenylethyl, phenylpropyl and naphthylmethyl, especially benzyl.

Suitable heterocycloalkyl groups include azetidinyl, pyrrolidinyl, piperdinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups. Further heteroaryl groups include [1,2,4] triazolo[1,5-a]pyridinyl, 5,6,7,8-tetrahydro[1,2,4]triazolo[1,5-a]pyridinyl and 5,6,7,8-tetrahydro[1,2,4]triazolo[1,5-a]pyrazinyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl. The expression "heteroaryl($C_{1-6}$)alkyl" as used herein further includes [1,2,4]triazolo[1,5-a]pyridinylmethyl, 5,6,7,8-tetrahydro[1,2,4]triazolo[1,5-a]pyridinylmethyl and 5,6,7,8-tetrahydro[1,2,4]triazolo[1,5-a]pyrazinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, the substituent Z in the compounds of formula I above represents halogen (e.g. bromo or iodo); or $C_{1-6}$ alky, aryl or heteroaryl, any of which groups may be optionally substituted. Suitably, Z may represent $C_{1-6}$ alkyl, aryl or heteroaryl, any of which groups may be optionally substituted.

Suitable values for the substituent Z include tert-butyl, 1,1-dimethylpropyl, phenyl, pyridinyl, furyl and thienyl, any of which groups may be optionally substituted by one or more substituents.

Specific examples of optional substituents on the group Z include methyl, fluoro, chloro, trifluoromethyl, cyano and amino. Illustrative optional substituents include fluoro, chloro, trifluoromethyl, cyano and amino.

Examples of typical optional substituents on the group Z include methyl, fluoro, chloro and trifluoromethyl. Particular substituents include fluoro, chloro and trifluoromethyl, especially fluoro.

Representative values of Z in the compounds of formula I above include tert-butyl, 1,1-dimethylpropyl, phenyl, fluorophenyl, difluorophenyl, chlorophenyl, trifluoromethyl-phenyl, cyanophenyl, aminophenyl, pyridinyl, furyl and thienyl.

Typical examples of suitable values for the group Z include tert-butyl, 1,1-dimethylpropyl, phenyl, fluorophenyl, difluorophenyl, chlorophenyl, trifluoromethyl-phenyl, pyridinyl, furyl and thienyl.

Further examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]hept-1-yl, phenyl, pyrrolidinyl, methyl-pyrrolidinyl, piperidinyl, morpholinyl, thiomorpholinyl, pyridinyl, furyl, thienyl, chloro-thienyl and diethylamino.

In a particular embodiment, the substituent Z represents $C_{3-7}$ cycloalkyl, either unsubstituted or substituted by $C_{1-6}$ alkyl, especially methyl. Favourably, Z represents cyclobutyl.

In another embodiment, Z represents tert-butyl.

In a further embodiment, Z represents phenyl.

In a still further embodiment, Z represents fluorophenyl.

Examples of typical optional substituents on the group $R^1$ include methyl, fluoro, chloro and methoxy. Particular substituents include methyl, fluoro and methoxy, especially fluoro.

Specific values of $R^1$ include cyclopropyl, phenyl, methylphenyl, fluorophenyl, difluorophenyl, trifluorophenyl, chlorophenyl, methoxyphenyl, furyl, thienyl, methyl-thienyl, pyridinyl and pyrazinyl.

Typical values of $R^1$ include cyclopropyl, phenyl, methylphenyl, fluorophenyl, difluorophenyl, trifluorophenyl, methoxyphenyl, furyl, thienyl, methyl-thienyl, pyridinyl and pyrazinyl.

Representative values of $R^1$ include cyclopropyl, phenyl, methylphenyl, fluorophenyl, difluorophenyl, methoxyphenyl, furyl, thienyl, methyl-thienyl and pyridinyl.

Particular values of $R^1$ include cyclopropyl, phenyl, fluorophenyl, difluorophenyl, trifluorophenyl, chlorophenyl, furyl, thienyl, pyridinyl and pyrazinyl.

Illustrative values of $R^1$ include phenyl, fluorophenyl, difluorophenyl, trifluorophenyl, furyl, thienyl, pyridinyl and pyrazinyl.

More particularly, $R^1$ may represent unsubstituted or monosubstituted phenyl. Most particularly, $R^1$ represents phenyl or fluorophenyl. In one specific embodiment, $R^1$ represents fluorophenyl.

Suitably, $R^2$ represents aryl($C_{1-6}$)alkyl or heteroaryl($C_{1-6}$)alkyl, either of which groups may be optionally substituted.

Suitable values for the substituent $R^2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents. Further values for the substituent $R^2$ suitably include [1,2,4]triazolo[1,5-a]pyridinylmethyl, 5,6,7,8-tetrahydro[1,2,4]triazolo[1,5-a]pyridinylmethyl and 5,6,7,8-tetrahydro[1,2,4]triazolo[1,5-a]pyrazinylmethyl, any of which groups may be optionally substituted by one or more substituents.

Typical values of $R^2$ include benzyl, pyrazolylmethyl, thiazolylmethyl, benzimidazolylmethyl, triazolylmethyl, pyridinylmethyl, pyridazinylmethyl, pyrimidinylmethyl, pyrazinylmethyl, quinoxalinylmethyl, [1,2,4]triazolo[1,5-a]pyridinylmethyl, 5,6,7,8-tetrahydro[1,2,4]triazolo[1,5-a]pyridinylmethyl and 5,6,7,8-tetrahydro[1,2,4]triazolo[1,5-a]pyrazinylmethyl, any of which groups may be optionally substituted by one or more substituents.

In one embodiment, $R^2$ represents triazolylmethyl or pyridinylmethyl, either of which groups may be optionally substituted by one or more substituents.

Suitably, $R^2$ represents an optionally substituted triazolylmethyl group.

Examples of suitable optional substituents on the group $R^2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$)alkylmorpholinyl($C_{1-6}$)alkyl, especially $C_{1-6}$ alkyl.

Further examples of suitable optional substituents on $R^2$ include dihalo($C_{1-6}$)alkyl, cyano($C_{1-6}$)alkoxy and $C_{3-7}$ cycloalkoxy.

Examples of typical optional substituents on the group $R^2$ include $C_{1-6}$ alkyl, halo($C_{1-6}$)alkyl, dihalo($C_{1-6}$)alkyl, cyano, $C_{1-6}$ alkoxy, cyano($C_{1-6}$)alkoxy, $C_{3-7}$ cycloalkoxy and di($C_{1-6}$)alkylamino($C_{1-6}$)alkyl, especially $C_{1-6}$ alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl.

Another specific optional substituent on $R^2$ is isopropyl.

Further illustrations of specific substituents on $R^2$ include fluoroethyl, difluoroethyl, methoxy, cyanomethoxy and cyclobutyloxy.

Particular examples of specific substituents on the group $R^2$ include methyl, ethyl, n-propyl, isopropyl, fluoroethyl, difluoroethyl, cyano, methoxy, ethoxy, cyanomethoxy, cyclobutyloxy and dimethylaminomethyl.

Selected substituents for the group $R^2$ include methyl, ethyl, n-propyl and isopropyl, especially methyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Further values of $R^2$ include ethyl-triazolylmethyl and isopropyl triazolylmethyl.

Still further values of $R^2$ include dimethylaminomethyl-benzyl, methyl-benzimidazolylmethyl, fluoroethyl-triazolylmethyl, difluoroethyl-triazolylmethyl, cyano-pyridinylmethyl, methoxy-pyridinylmethyl, cyanomethoxy-pyridinylmethyl, cyclobutyloxy-pyridinylmethyl, [1,2,4]triazolo[1,5-a]pyridinylmethyl, 5,6,7,8-tetrahydro[1,2,4]triazolo[1,5-a]pyridinylmethyl and 5,6,7,8-tetrahydro[1,2,4]triazolo[1,5-a]pyrazinylmethyl.

Illustrative values of $R^2$ include dimethylaminomethyl-benzyl, dimethyl-pyrazolylmethyl, thiazolylmethyl, methyl-thiazolylmethyl, methyl-benzimidazolylmethyl, methyl-triazolylmethyl, ethyl-triazolylmethyl, propyl-triazolylmethyl, isopropyl-triazolylmethyl, fluoroethyl-triazolylmethyl, difluoroethyl-triazolylmethyl, pyridinylmethyl, methyl-pyridinylmethyl, cyano-pyridinylmethyl, methoxy-pyridinylmethyl, ethoxy-pyridinylmethyl, cyanomethoxy-pyridinylmethyl, cyclobutyloxy-pyridinylmethyl, pyridazinylmethyl, pyrimidinylmethyl, pyrazinylmethyl, quinoxalinylmethyl, [1,2,4]triazolo[1,5-a]pyridinylmethyl, 5,6,7,8-tetrahydro[1,2,4]triazolo[1,5-a]pyridinylmethyl and 5,6,7,8-tetrahydro[1,2,4]triazolo[1,5-a]pyrazinylmethyl.

Specific values of $R^2$ include methyl-triazolylmethyl, ethyl-triazolylmethyl, propyl-triazolylmethyl, isopropyl-triazolylmethyl and pyridinylmethyl.

A favoured value of $R^2$ is methyl-triazolylmethyl.

A particular sub-class of compounds according to the invention is represented by the compounds of formula IIA, and salts and prodrugs thereof:

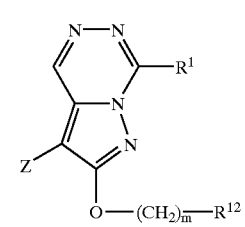

(IIA)

wherein

Z and $R^1$ are as defined with reference to formula I above;

m is 1 or 2, preferably 1; and $R^{12}$ represents aryl or heteroaryl, either of which groups may be optionally substituted.

Suitably, $R^{12}$ represents phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl or quinoxalinyl, any of which groups may be optionally substituted by one or more substituents. Suitably, $R^{12}$ may also represent [1,2,4]triazolo[1,5-a]pyridinyl, 5,6,7,8-tetrahydro[1,2,4]triazolo[1,5-a]pyridinyl or 5,6,7,8-tetrahydro[1,2,4]triazolo[1,5-a]pyrazinyl, any of which groups may be optionally substituted by or more substituents.

Typical values of $R^{12}$ include phenyl, pyrazolyl, thiazolyl, benzimidazolyl, triazolyl, pyridinyl, pyridazinyl, pyrimidinyl, pyrazinyl, quinoxalinyl, [1,2,4]triazolo [1,5-a]

pyridinyl, 5,6,7,8-tetrahydro[1,2,4]triazolo[1,5-a]pyridinyl and 5,6,7,8-tetrahydro[1,2,4]triazolo[1,5-a]pyrazinyl, any of which groups may be optionally substituted by one or more substituents.

Suitable values of $R^{12}$ include triazolyl and pyridinyl, either of which groups may be optionally substituted by one or more substituents.

A particular value of $R^{12}$ is optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl, especially $C_{1-6}$ alkyl.

Further examples of typical substituents on $R^{12}$ include halo($C_{1-6}$)alkyl, dihalo($C_{1-6}$)alkyl, cyano($C_{1-6}$)alkoxy and $C_{3-7}$ cycloalkoxy.

Examples of suitable optional substituents on $R^{12}$ include $C_{1-6}$ alkyl, halo($C_{1-6}$)alkyl, dihalo($C_{1-6}$)alkyl, cyano, $C_{1-6}$ alkoxy, cyano($C_{1-6}$)alkoxy, $C_{3-7}$ cycloalkoxy and di($C_{1-6}$)alkylamino($C_{1-6}$)alkyl, especially $C_{1-6}$ alkyl.

Illustrative values of specific substituents on the group $R^{12}$ include methyl, ethyl, n-propyl, benzyl, pyridinylmethyl, chloro cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl.

Another specific optional substituent on $R^{12}$ is isopropyl.

Further illustrations of specific substituents on $R^{12}$ include fluoroethyl, difluoroethyl, methoxy, cyanomethoxy and cyclobutyloxy.

Particular examples of specific substituents on the group $R^{12}$ include methyl, ethyl, n-propyl, isopropyl, fluoroethyl, difluoroethyl, cyano, methoxy, ethoxy, cyanomethoxy, cyclobutyloxy and dimethylaminomethyl.

Selected substituents for the group $R^{12}$ include methyl, ethyl, n-propyl, and isopropyl, especially methyl.

Particular values of $R^{12}$ include cyanophenyl, hydroxymethylphenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Further values of $R^{12}$ include ethyl-triazolyl and isopropyl-triazolyl.

Still further values of $R^{12}$ include dimethylaminomethyl-phenyl, methyl-benzimidazolyl, fluoroethyl-triazolyl, difluoroethyl-triazolyl, cyano-pyridinyl, methoxy-pyridinyl, cyanomethoxy-pyridinyl, cyclobutyloxy-pyridinyl, [1,2,4] triazolo[1,5-a]pyridinyl, 5,6,7,8-tetrahydro[1,2,4]triazolo[1, 5-a]pyridinyl and 5,6,7,8-tetrahydro[1,2,4]triazolo[1,5-a] pyrazinyl.

Illustrative values of $R^{12}$ include dimethylaminomethyl-phenyl, dimethyl-pyrazolyl, thiazolyl, methyl-thiazolyl, methyl-benzimidazolyl, methyl-triazolyl, ethyl-triazolyl, propyl-triazolyl, isopropyl-triazolyl, fluoroethyl-triazolyl, difluoroethyl-triazolyl, pyridinyl, methyl-pyridinyl, cyano-pyridinyl, methoxy-pyridinyl, ethoxy-pyridinyl, cyanomethoxy-pyridinyl, cyclobutyloxy-pyridinyl, pyridazinyl, pyrimidinyl, pyrazinyl, quinoxalinyl, [1,2,4] triazolo[1,5-a]pyridinyl, 5,6,7,8-tetrahydro[1,2,4]triazolo[1, 5-a]pyridinyl and 5,6,7,8-tetrahydro[1,2,4]triazolo[1,5-a] pyrazinyl.

Specific values of $R^{12}$ include methyl-triazolyl, ethyl-triazolyl, propyl-triazolyl, isopropyl-triazolyl and pyridinyl.

A favoured value of $R^{12}$ is methyl-triazolyl.

A particular subset of the compounds of formula IIA above is represented by the compounds of formula IIB, and pharmaceutically acceptable salts thereof:

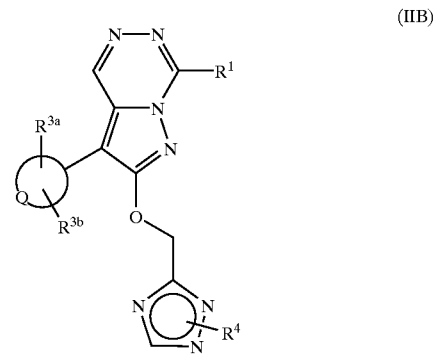

(IIB)

wherein $R^1$ is as defined with reference to formula I above;

Q represents the residue of a cyclopropyl, cyclobutyl, cyclopentyl, cyclohexyl, phenyl, pyridinyl, furyl or thienyl ring;

$R^{3a}$ represents hydrogen, methyl, fluoro, chloro, trifluoromethyl, cyano or amino;

$R^{3b}$ represents hydrogen or fluoro; and $R^4$ represents hydrogen, methyl, ethyl, n-propyl, isopropyl, fluoroethyl or difluoroethyl.

The present invention also provides a compound of formula IIB as depicted above, or a pharmaceutically acceptable salt thereof, wherein $R^1$ is as defined with reference to formula I above;

$R^{3a}$ represents hydrogen, methyl, fluoro, chloro or trifluoromethyl;

$R^4$ represents hydrogen, methyl, ethyl, n-propyl or isopropyl; and

Q and $R^{3b}$ are as defined above.

The present invention further provides a compound of formula IIB as depicted above, or a pharmaceutically. acceptable salt thereof, wherein $R^1$ is as defined with reference to formula I above;

Q represents the residue of a cyclopropyl, cyclobutyl, cyclopentyl, cyclohexyl or phenyl ring;

$R^{3a}$ represents hydrogen. methyl or fluoro;

$R^{3b}$ represents hydrogen; and $R^4$ represents hydrogen or methyl.

In relation to formula IIB above, $R^1$ suitably represents phenyl, fluorophenyl, difluorophenyl, trifluorophenyl, furyl, thienyl, pyridinyl or pyrazinyl, especially phenyl or fluorophenyl, and more especially fluorophenyl.

In one embodiment of the compounds of formula IIB above, Q represents the residue of a cyclobutyl, phenyl, pyridinyl, furyl or thienyl ring. In a subset of this embodiment, Q represents the residue of a phenyl, pyridinyl, furyl or thienyl ring.

In a particular embodiment, Q suitably represents the residue of a cyclobutyl ring. In another embodiment, Q represents the residue of a phenyl ring.

Suitably, $R^{3a}$ represents hydrogen or fluoro, typically hydrogen.

Typically, $R^{3b}$ represents hydrogen.

Suitably, $R^4$ represents methyl.

Specific compounds within the scope of the present invention include:

7-(2-fluorophenyl)-2-(2-methyl-2H-[1,2,4]triazol-3-ylmethoxy)-3-phenylpyrazolo[1,5-d][1,2,4]triazine;

3-(2-fluorophenyl)-7-(2-fluorophenyl)-2-(2-methyl-2H-[1,2,4]triazol-3-ylmethoxy)pyrazolo[1,5-d][1,2,4]triazine;

3-(3-fluorophenyl)-7-(2-fluorophenyl)-2-(2-methyl-2H-[1,2,4]triazol-3-ylmethoxy)pyrazolo[1,5-d][1,2,4]triazine;

3-(4-fluorophenyl)-7-(2-fluorophenyl)-2-(2-methyl-2H-[1,2,4]triazol-3-ylmethoxy)pyrazolo[1,5-d][1,2,4]triazine;

2-(2-ethyl-2H-[1,2,4]triazol-3-ylmethoxy)-7-(2-fluorophenyl)-3-phenylpyrazolo[1,5-d][1,2,4]triazine;

7-(2-fluorophenyl)-2-(1-methyl-1H-[1,2,4]triazol-3-ylmethoxy)-3-phenylpyrazolo[1,5-d][1,2,4]triazine;

7-(3-fluorophenyl)-2-(2-methyl-2H-[1,2,4]triazol-3-ylmethoxy)-3-phenyl-pyrazolo[1,5-d][1,2,4]triazine;

7-(2-fluorophenyl)-3-phenyl-2-(pyridin-2-ylmethoxy)pyrazolo[1,5-d][1,2,4]triazine;

7-(4-fluorophenyl)-2-(2-methyl-2H-[1,2,4]triazol-3-ylmethoxy)-3-phenylpyrazolo[1,5-d][1,2,4]triazine;

7-(2,6-difluorophenyl)-2-(2-methyl-2H-[1,2,4]triazol-3-ylmethoxy)-3-phenylpyrazolo[1,5-d][1,2,4]triazine;

2-(2-methyl-2H-[1,2,4]triazol-3-ylmethoxy)-3-phenyl-7-(thien-2-yl)-pyrazolo[1,5-d][1,2,4]triazine;

3,7-diphenyl-2-(2-methyl-2H-[1,2,4]triazol-3-ylmethoxy)pyrazolo[1,5-d][1,2,4]triazine;

7-(2,5-difluorophenyl)-2-(2-methyl-2H-1,2,4]triazol-3-ylmethoxy)-3-phenylpyrazolo[1,5-d][1,2,4]triazine;

3-(2,5-difluorophenyl)-7-(2-fluorophenyl)-2-(2-methyl-2H-[1,2,4]triazol-3-ylmethoxy)pyrazolo[1,5-][1,2,4]triazine;

3-(2,6-difluorophenyl)-7-(2-fluorophenyl)-2-(2-methyl-2H-[1,2,4]triazol-3-ylmethoxy)pyrazolo[1,5-d][1,2,4]triazine;

3-(2,3-difluorophenyl)-7-(2-fluorophenyl)-2-(2-methyl-2H-[1,2,4]triazol-3-ylmethoxy)pyrazolo[1,5-d][1,2,4]triazine;

3-bromo-7-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-[3-(trifluoromethyl)phenyl]pyrazolo[1,5-d][1,2,4]triazine;

7-(2-fluorophenyl)-2-(2-methyl-2H-[1,2,4]triazol-3-ylmethoxy)-3-(thien-3-yl)pyrazolo[1,5-d][1,2,4]triazine;

3-(3,5-difluorophenyl)-7-(2-fluorophenyl)-2-(2-methyl-2H-[1,2,4]triazol-3-ylmethoxy)pyrazolo[1,5-d][1,2,4]triazine;

7-(2,5-difluorophenyl)-3-(1,1-dimethylethyl)-2-(2-methyl-2H-[1,2,4]triazol-3-ylmethoxy)pyrazolo[1,5-d][1,2,4]triazine;

7-(2,5-difluorophenyl)-3-(1,1-dimethylethyl)-2-(2-ethyl-2H-[1,2,4]triazol-3-ylmethoxy)pyrazolo[1,5-d][1,2,4]triazine;

7-(2,5-difluorophenyl)-3-(1,1-dimethylethyl)-2-(2-propyl-2H-[1,2,4]triazol-3-ylmethoxy)pyrazolo[1,5-d][1,2,4]triazine;

3-(1,1-dimethylethyl)-7-(2-fluorophenyl)-2-(2-methyl-2H-[1,2,4]triazol-3-ylmethoxy)pyrazolo[1,5-d][1,2,4]triazine;

3-(1,1-dimethylethyl)-2-(2-ethyl-2H-[1,2,4]triazol-3-ylmethoxy)-7-(2-fluorophenyl)pyrazolo[1,5-d][1,2,4]triazine;

3-(1,1-dimethylethyl)-7-(2-fluorophenyl)-2-(2-propyl-2H-[1,2,4]triazol-3-ylmethoxy)pyrazolo[1,5-d][1,2,4]triazine;

7-(2,5-difluorophenyl)-3-(1,1-dimethylpropyl)-2-(2-methyl-2H-[1,2,4]triazol-3-ylmethoxy)pyrazolo[1,5-d][1,2,4]triazine;

3-(1,1-dimethylethyl)-2-(2-methyl-2H-[1,2,4]triazol-3-ylmethoxy)-7-(2,3,6-trifluorophenyl)pyrazolo[1,5-d][1,2,4]triazine;

3-(1,1-dimethylethyl)-2-(2-ethyl-2H-[1,2,4]triazol-3-ylmethoxy)-7-(2,3,6-trifluorophenyl)pyrazolo[1,5-d][1,2,4]triazine;

7-(2,5-difluorophenyl)-3-(1,1-dimethylethyl)-2-(2-isopropyl-2H-[1,2,4]triazol-3-ylmethoxy)pyrazolo[1,5-d][1,2,4]triazine;

3-(2-fluorophenyl)-2-(2-methyl-2H-[1,2,4]triazol-3-ylmethoxy)-7-(pyrazin-2-yl)pyrazolo[1,5-d][1,2,4]triazine;

3-(2-chlorophenyl)-7-(2-fluorophenyl)-2-(2-methyl-2H-[1,2,4]triazol-3-ylmethoxy)pyrazolo[1,5-d][1,2,4]triazine;

7-(2,5-difluorophenyl)-3-(1,1-dimethylpropyl)-2-(2-ethyl-2H-[1,2,4]triazol-3-ylmethoxy)pyrazolo[1,5-d][1,2,4]triazine;

3-(1,1-dimethylpropyl)-7-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-(pyridin-3-yl)pyrazolo[1,5-d][1,2,4]triazine;

3-(2-fluorophenyl)-7-(furan-2-yl)-2-(2-methyl-2H-[1,2,4]triazol-3-ylmethoxy)pyrazolo[1,5-d][1,2,4]triazine;

3-(1,1-dimethylethyl)-7-(4-fluorophenyl)-2-(2-methyl-2H-[1,2,4]triazol-3-ylmethoxy)pyrazolo[1,5-d][1,2,4]triazine;

3-(1,1-dimethylethyl)-2-(2-ethyl-2H-[1,2,4]triazol-3-ylmethoxy)-7-(4-fluorophenyl)pyrazolo[1,5-d][1,2,4]triazine;

3-(1,1-dimethylethyl)-7-(4-fluorophenyl)-2-(2-propyl-2H-[1,2,4]triazol-3-ylmethoxy)pyrazolo[1,5-d][1,2,4]triazine;

3-(1,1-dimethylpropyl)-2-(2-ethyl-2H-[1,2,4]triazol-3-ylmethoxy)-7-(2-fluorophenyl)pyrazolo[1,5-d][1,2,4]triazine;

3-(2-fluorophenyl)-7-(4-fluorophenyl)-2-(2-methyl-2H-[1,2,4]-triazol-3-ylmethoxy)pyrazolo[1,5-d][1,2,4]triazine;

3-(3-chlorophenyl)-7-(2-fluorophenyl)-2-(2-methyl-2H-[1,2,4]triazol-3-ylmethoxy)pyrazolo[1,5-d][1,2,4]triazine;

3-(1,1-dimethylpropyl)-2-(2-methyl-2H-[1,2,4]triazol-3-ylmethoxy)-7-(2,3,6-trifluorophenyl)pyrazolo[1,5-d][1,2,4]triazine;

3-(1,1-dimethylpropyl)-2-(2-ethyl-2H-[1,2,4]triazol-3-ylmethoxy)-7-(2,3,6-trifluorophenyl)pyrazolo[1,5-d][1,2,4]triazine;

3-(2-fluorophenyl)-2-(2-methyl-2H-[1,2,4]triazol-3-ylmethoxy)-7-(pyridin-3-yl)pyrazolo[1,5-d][1,2,4]triazine;

2-(2-ethyl-2H-[1,2,4]triazol-3-ylmethoxy)-7-(2-fluorophenyl)-3-(pyridin-4-yl)pyrazolo[1,5-d][1,2,4]triazine;

2-(2-ethyl-2H-[1,2,4]triazol-3-ylmethoxy)-3-(2-fuorophenyl)-7-(4-fluorophenyl)pyrazolo[1,5-d][1,2,4]triazine;

3-(2-fluorophenyl)-7-(4-fluorophenyl)-2-(2-propyl-2H-[1,2,4]triazol-3-ylmethoxy)pyrazolo[1,5-d][1,2,4]triazine;

7-(2,6-difluorophenyl)-3-(2-fluorophenyl)-2-(2-methyl-2H-[1,2,4]triazol-3-ylmethoxy)pyrazolo[1,5-d][1,2,4]triazine;

7-(2,6-difluorophenyl)-2-(2-ethyl-2H-[1,2,4]triazol-3-ylmethoxy)-3-(2-fluorophenyl)pyrazolo[1,5-d][1,2,4]triazine;

3-(2-fluorophenyl)-7-(3-fluorophenyl)-2-(2-methyl-2H-[1,2,4]triazol-3-ylmethoxy)pyrazolo[1,5 -d][1,2,4]triazine;

7-(2,4-difluorophenyl)-3-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-(pyridin-2-yl)pyrazolo[1,5-d][1,2,4]triazine;

7-(2-fluorophenyl)-2-(2-methyl-2H-[1,2,4]triazol-3-ylmethoxy)-3-(thien-2-yl)pyrazolo[1,5-d][1,2,4]triazine;

7-(2-fluorophenyl)-3-(furan-2-yl)-2-(2-methyl-2H-[1,2,4]triazol-3-ylmethoxy)pyrazolo[1,5-d][1,2,4]triazine;

7-(2,4-difluorophenyl)-3-(1,1-dimethylethyl)-2-(2-methyl-2H-[1,2,4]triazol-3-ylmethoxy)pyrazolo[1,5-d][1,2,4]triazine;

7-(2,4-difluorophenyl)-3-(1,1-dimethylethyl)-2-(2-ethyl-2H-[1,2,4]triazol-3-ylmethoxy)pyrazolo[1,5-d][1,2,4]triazine;

7-(2,4-difluorophenyl)-3-(1,1-dimethylethyl)-2-(2-ethyl-2H-[1,2,4]triazol-3-ylmethoxy)pyrazolo[1,5-d][1,2,4]trazine;

2-(2-ethyl-2H-[1,2,4]triazol-3-ylmethoxy)-3,7-bis(2-fluorophenyl)pyrazolo[1,5-d][1,2,4]triazine;

3,7-bis(2-fluorophenyl)-2-(1-methyl-1H-[1,2,4]triazol-3-ylmethoxy)pyrazolo[1,5-d][1,2,4]triazine;

3,7-bis(2-fluorophenyl)-2-(3-methyl-3H-[1,2,3]triazol-4-ylmethoxy)pyrazolo[1,5-d][1,2,4]triazine;

3,7-bis(2-fluorophenyl)-2-(1-methyl-1H-[1,2,3]triazol-4-ylmethoxy)pyrazolo[1,5-d][1,2,4]triazine;

3,7-bis(2-fluorophenyl)-2-(6-methylpyridin-2-ylmethoxy)pyrazolo[1,5-d][1,2,4]triazine;

3,7-bis(2-fluorophenyl)-2-(pyridin-3-ylmethoxy)pyrazolo[1,5-d][1,2,4]triazine;

3,7-bis(2-fluorophenyl)-2-(pyridin-4-ylmethoxy)pyrazolo[1,5-d][1,2,4]triazine;

2-(3-cyclobutyloxypyridin-2-ylmethoxy)-3,7-bis(2-fluorophenyl)pyrazolo[1,5-d][1,2,4]triazine;

2-[3,7-bis(2-fluorophenyl)pyrazolo[1,5-d][1,2,4]triazin-2-yloxymethyl]-pyridin-3-yloxyacetonitrile;

3,7-bis(2-fluorophenyl)-2-(3-methoxypyridin-2-ylmethoxy)pyrazolo[1,5-d][1,2,4]triazine;

2-(3-ethoxypyridin-2-ylmethoxy)-3,7-bis(2-fluorophenyl)pyrazolo[1,5-d][1,2,4]triazine;

3,7-bis(2-fluorophenyl)-2-(3-methylpyridin-2-ylmethoxy)pyrazolo[1,5-d][1,2,4]triazine;

N-[3-[3,7-bis(2-fluorophenyl)pyrazolo[1,5-d][1,2,4]triazin-2-yloxymethyl]benzyl]-N,N-dimethylamine;

3,7-bis(2-fluorophenyl)-2-(4-methylthiazol-2-ylmethoxy)pyrazolo[1,5-d][1,2,4]triazine;

3,7-bis(2-fluorophenyl)-2-(5-methylthiazol-2-ylmethoxy)pyrazolo[1,5-d][1,2,4]triazine;

3,7-bis(2-fluorophenyl)-2-(thiazol-4-ylmethoxy)pyrazolo[1,5-d][1,2,4]triazine;

3,7-bis(2-fluorophenyl)-2-(2-isopropyl-2H-[1,2,4]triazol-3-ylmethoxy)pyrazolo[1,5-d][1,2,4]triazine;

6-[3,7-bis(2-fluorophenyl)pyrazolo[1,5-d][1,2,4]triazin-2-yloxymethyl]-nicotinonitrile;

3,7-bis(2-fluorophenyl)-2-(pyridazin-3-ylmethoxy)pyrazolo[1,5-d][1,2,4]triazine;

3,7-bis(2-fluorophenyl)-2-(pyrazin-2-ylmethoxy)pyrazolo[1,5-d][1,2,4]triazine;

3,7-bis(2-fluorophenyl)-2-(pyrimidin-4-ylmethoxy)pyrazolo[1,5-d][1,2,4]triazine;

3,7-bis(2-fluorophenyl)-2-(quinoxalin-2-ylmethoxy)pyrazolo[1,5-d][1,2,4]triazine;

3-(2-fluorophenyl)-7-(furan-3-yl)-2-(2-methyl-2H-[1,2,4]triazol-3-ylmethoxy)pyrazolo[1,5-d][1,2,4]triazine;

3,7-bis(2-fluorophenyl)-2-(1-methyl-1H-benzimidazol-2-ylmethoxy)pyrazolo[1,5-d][1,2,4]triazine;

3,7-bis(2-fluorophenyl)-2-([1,2,4]triazolo[1,5-a]pyridin-2-ylmethoxy)pyrazolo[1,5-d][1,2,4]triazine;

3,7-bis(2-fluorophenyl)-2-(5,6,7,8-tetrahydro[1,2,4]triazolo[1,5-a]pyridin-2-ylmethoxy)pyrazolo[1,5-d][1,2,4]triazine;

2-[3,7-bis(2-fluorophenyl)pyrazolo[1,5-d][1,2,4]triazin-2-yloxymethyl]-5,6,7,8-tetrahydro-[1,2,4]triazolo[1,5-a]pyrazine;

2-[2-(2,2-difluoroethyl)-2H-[1,2,4]triazol-3-ylmethoxy]-3,7-bis(2-fluorophenyl)pyrazolo[1,5-d][1,2,4]triazine;

2-[2-(2-fluoroethyl)-2H-[1,2,4]triazol-3-ylmethoxy]-3,7-bis(2-fluorophenyl)pyrazolo[1,5-d][1,2,4]triazine;

7-(2,5-difluorophenyl)-3-(2-fluorophenyl)-2-(2-methyl-2H-[1,2,4]triazol-3-ylmethoxy)pyrazolo[1,5-d][1,2,4]triazine;

7-(2-chlorophenyl)-3-(2-fluorophenyl)-2-(2-methyl-2H-[1,2,4]triazol-3-ylmethoxy)pyrazolo[1,5-d][1,2,4]triazine;

7-cyclopropyl-3-(2-fluorophenyl)-2-(2-methyl-2H-[1,2,4]triazol-3-ylmethoxy)pyrazolo[1,5-d][1,2,4]triazine;

3,7-bis(2-fluorophenyl)-2-(1,5-dimethyl-1H-pyrazol-3-ylmethoxy)pyrazolo[1,5-d][1,2,4]triazine;

2-(2-ethyl-2H-[1,2,4]triazol-3-ylmethoxy)-7-(2-fluorophenyl)-3-(furan-2-yl)pyrazolo[1,5-d][1,2,4]triazine;

2-(2-ethyl-2H-[1,2,4]triazol-3-ylmethoxy)-7-(2-fluorophenyl)-3-(thien-2-yl)pyrazolo[1,5-d][1,2,4]triazine;

2-(2-ethyl-2H-[1,2,4]triazol-3-ylmethoxy)-7-(2-fluorophenyl)-3-(thien-3-yl)pyrazolo[1,5-d][1,2,4]triazine;

3-(3-aminophenyl)-7-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-[3-(pyridin-3-yl)phenyl]pyrazolo[1,5-d][1,2,4]triazine;

7-(2-fluorophenyl)-3-iodo-2-(2-methyl-2H-[1,2,4]triazol-3-ylmethoxy)pyrazolo[1,5-d][1,2,4]triazine;

3-(3-cyanophenyl)-7-(2-fluorophenyl)-2-(2-methyl-2H-[1,2,4]triazol-3-ylmethoxy)pyrazolo[1,5-d][1,2,4]triazine;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk-fibroblast cells.

The compounds according to the present invention exhibit anxiolytic activity, as may be demonstrated by a positive response in the elevated plus maze and conditioned suppression of drinking tests (cf Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow, et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be: capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises cyclising a compound of formula III:

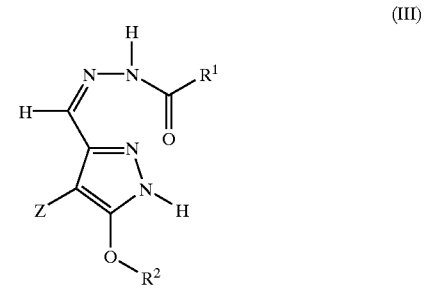

(III)

wherein Z, $R^1$ and $R^2$ are as defined above.

The cyclisation of compound III may conveniently be effected by heating compound III to an elevated temperature, e.g. (i) a temperature in the region of 180–200° C., in the presence of a high-boiling medium such as Dowtherm A; or (ii) at the reflux temperature of an inert solvent such as xylene, optionally in the presence of a proton source such as triethylamine hydrochloride.

The intermediates of formula III above may be prepared by reacting a compound of formula IV with a hydrazide derivative of formula V:

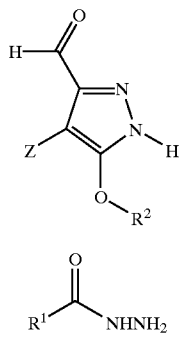

(IV)

(V)

wherein Z, R¹ and R² are as defined above.

The reaction between compounds IV and V is conveniently effected by heating the reactants, optionally in the presence of a proton source such as triethylamine hydrochloride, typically at reflux in an inert solvent such as xylene.

In another procedure, the compounds of formula I as defined above may be prepared by a process which comprises reacting a compound of formula VI with a compound of formula VII:

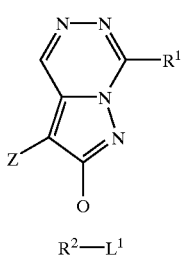

(VI)

R²—L¹ (VII)

wherein Z, R¹ and R² are as defined above, and L¹ represents a suitable leaving group.

The leaving group L¹ is suitably a halogen atom, typically chloro.

The reaction between compounds VI and VII is conveniently effected by stirring the reactants in a suitable solvent, typically N,N-dimethylformamide, in the presence of a base such as cesium carbonate or potassium carbonate.

Similarly, the intermediates of formula IV may be prepared by reacting a compound of formula VII as defined above with a compound of formula VIII:

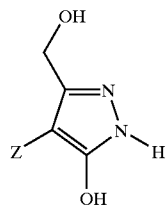

(VIII)

wherein Z is as defined above; under conditions analogous to those described above for the reaction between compounds VI and VII; followed by oxidation.

Oxidation of the CH₂OH side-chain in the intermediate resulting from the reaction between compounds VII and VIII to the aldehyde CHO side-chain in the corresponding intermediate of formula IV is suitably effected by treatment with manganese dioxide, in which case the reaction is conveniently carried out in chloroform at an elevated temperature in the region of 70° C.

In a further procedure, the compounds of formula I as defined above may be prepared by a process which comprises reacting a compound of formula IX with a compound of formula X:

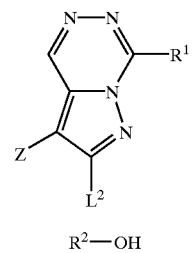

(IX)

R²—OH (X)

wherein Z, R¹ and R² are as defined above, and L² represents a suitable leaving group.

The leaving group L² is typically an arylsulfonyloxy moiety, e.g. p-toluenesulfonyloxy (tosyloxy).

The reaction between compounds IX and X is conveniently effected by stirring the reactants in a suitable solvent, typically N,N-dimethylformamide, in the presence of a base such as sodium hydride.

The intermediates of formula IX above may be prepared by reacting a compound of formula V as defined above with a compound of formula XI:

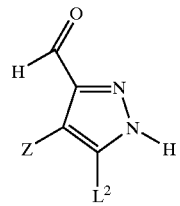

(XI)

wherein Z and L² are as defined above.

The reaction between compounds V and XI is conveniently effected by heating the reactants, optionally in the presence of a proton source such as triethylamine hydrochloride, typically at reflux in an inert solvent such as xylene.

In a still further procedure, the compounds of formula I as defined above may be prepared by a process which comprises reacting a compound of formula XII with a compound of formula XIII:

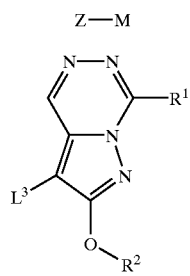

(XII)

(XIII)

wherein Z, $R^1$ and $R^2$ are as defined above, $L^3$ represents a suitable leaving group, and M represents —$B(OH)_2$ or a cyclic ester thereof formed with an organic diol, e.g. 1,3-propanediol, or M represents —$Sn(Alk)_3$ in which Alk represents a $C_{1-6}$ alkyl group, typically n-butyl; in the presence of a transition metal catalyst.

The leaving group $L^3$ is typically a halogen atom, e.g. bromo.

Where M represents —$B(OH)_2$ or a cyclic ester thereof, the transition metal catalyst is suitably tris(dibenzylideneacetone)palladium(0), in which case the reaction between compounds XII and XIII is conveniently effected at an elevated temperature in a solvent such as 1,4-dioxane, typically in the presence of tri-tert-butylphosphine and cesium carbonate.

Where M represents —$Sn(Alk)_3$, the transition metal catalyst is suitably tetrakis(triphenylphosphine)palladium (0), in which case the reaction between compounds XII and XIII is conveniently effected at an elevated temperature in a solvent such as 1,4-dioxane, typically in the presence of copper(I) iodide.

The compounds of formula XIII above may be prepared by reacting a compound of formula VII as defined above with a compound of formula XIV:

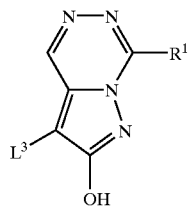

(XIV)

wherein $R^1$ and $L^3$ are as defined above; under conditions analogous to those described above for the reaction between compounds VI and VII.

The intermediates of formula XIV in which the leaving group $L^3$ represents bromo may be prepared by bromination of a compound of formula XV:

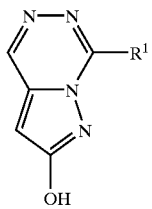

(XV)

wherein $R^1$ is as defined above.

The bromination reaction is conveniently effected by treating the appropriate compound of formula XV with bromine, typically in glacial acetic acid.

The intermediates of formula VII and X above may be prepared by the procedures described in WO 98/04559, or by methods analogous thereto.

Where they are not commercially available, the starting materials of formula V, VI, VIII, XI, XII and XV may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. Indeed, as will be appreciated, the compounds of formula XIII in which $L^3$ is halogen are compounds according to the invention in their own right. By way of example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic*

*Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml),

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which: the inhibition constant K$_i$ can be calculated for each test compound.

The compounds of the accompanying Examples were tested in the above assay, and all were found to possess a K$_i$ value for displacement of [$^3$H]-flumazenil from the α2 and/or α3 subunit of the human GABA$_A$ receptor of 100 nM or less.

EXAMPLE 1

7-(2-Fluorophenyl)-2-(2-methyl-2H-[1,2,4]triazol-3-ylmethoxy)-3-phenylpyrazolo[1,5-d][1,2,4]triazine a) 5-Hydroxymethyl-4-phenylpyrazol-3-one 4-Hydroxy-3-phenyl-2-furanone (3 g, 0.017 mol) was dissolved in ethanol (17 ml) with hydrazine hydrate (0.83 ml, 0.017 mol) and heated at reflux for 10 days (over this time the solvent evaporated). The residue was redissolved in ethanol (17 ml) and heated at reflux then allowed to cool and the solid that crystallised out was collected by filtration (2.2 g, mp=173° C.). Data for the title compound: $^1$H NMR (360 MHz, d$_6$-DMSO) δ 4.45 (1H, s), 5.31 (1H, s), 7.14 (1H, t, J=7.3 Hz), 7.34 (2H, t, J=7.3 Hz), 7.55 (2H, d, J=7.3 Hz); MS (ES$^+$) m/e 191 [MH]$^+$.

b) 3-Chloromethyl-2-methyl-2H-[1,2,4]triazole Hydrochloride (2-Methyl-2H-[1,2,4]triazol-3-yl)methanol (1 g) was added in portions to thionyl chloride (20 ml) and the solution was stirred at room temperature for 30 mins. The reaction mixture was concentrated under vacuum and the residue was azeotroped with toluene (2×30 ml) and dried under high vacuum to leave a crude product (1.3 g) which was used in the next step without characterisation or further purification.

c) 5-Hydroxymethyl-3-(2-methyl-2H-[1,2,4]triazol-3-ylmethoxy)-4-phenylpyrazole

The product from Example 1 Step a) (1.4 g, 0.0074 mol) in DMF (20 ml) had finely ground potassium carbonate (6.1 g, 6 mol. eq.) added followed by the product from Example 1 Step b) (1.24 g, 1.24 mol. eq.) and the reaction mixture was stirred at room temperature for 16 h. The reaction mixture was filtered and concentrated in vacuo to leave a residue which was purified by silica gel chromatography with 0–10% methanol/dichloromethane as eluent to give the required product (0.89 g, mp=139° C.). Data for the title compound: $^1$H NMR (360 MHz, CDCl$_3$) δ 3.89 (3H, s), 4.88 (2H, s), 5.51 (2H, s), 7.21–7.41 (5H, m), 7.79 (1H, s) (ES$^+$) m/e 286 [MH]$^+$.

d) 5-Formyl-3-(2-methyl-2H-[1,2,4]triazol-3-ylmethoxy)-4-phenylprazole

The product from Example 1 Step c) (0.64 g) was dissolved in chloroform (30 ml) and manganese dioxide (0.77 g) was added. The reaction mixture was heated at 70° C. for 14 h then cooled and filtered through a small plug of silica and after washing the silica with 5% methanol in dichloromethane the filtrate. was concentrated in vacuo to leave a residue (0.57 g, mp=190° C., dec.). The NMR peaks were broad suggesting the existence of 2 tautomers. Data for the title compound: $^1$H NMR (360 MHz, CDCl$_3$) δ 3.93 (3H, br, s), 5.54 (2H, br, s), 7.40–7.89 (6H, m), 9.80 (1H, br, s); MS (ES$^+$) m/e 284 [MH]$^+$.

e) 5-(2-Fluorophenyl)carbonylaminoimino-3-(2-methyl-2H-[1,2,4]triazol-3-ylmethoxy)-4-phenylpyrazole The product from Example 1 Step d) (0.56 g, 0.00198 mol) was suspended in xylene (20 ml) with 2-fluorobenzoic hydrazide (0.33 g, 1.1 mol. eq.) and triethylamine hydrochloride (0.24 g, 1 mol. eq.) and heated under reflux for 3 h. After cooling, the reaction mixture was filtered and the solid produced was washed in the sinter funnel several times with dichloromethane (0.67 g, mp=215° C.). The product existed as a 1:1 mixture of 2 tautomers. Data for the title compound: $^1$H NMR (360 MHz, CDCl$_3$) δ 3.93 (3H, s), 5.51 (2H, s), 7.14–7.55 (8H, m), 7.86 (1H, s), 8.17 (2H, m), 9.77 (0.5H, s), 9.81 (0.5H, s), 11.04 (1H, br, s); MS (ES$^+$) m/e 420 [MH]$^+$.

f) 7-(2-Fluorophenyl)-2-(2-methyl-2H-[1,2,4]triazol-3-ylmethoxy)-3-phenylpyrazolo[1,5-d][1,24]triazine The product from Example 1 Step e) (0.3 g, 0.0007 mol) was suspended in Dowtherm (20 ml) and heated at 200° C. for 3 h. After cooling, isohexane (100 ml) was added and the solid produced was collected by filtration. The crude product was dissolved in dichloromethane (100 ml) and washed with 1N sodium hydroxide solution (2×50 ml) and brine (1×50 ml). The organic layer was dried (MgSO$_4$), filtered, concentrated in vacuo and the residue that was obtained was recrystallised from ethyl acetate to give the required product (0.098 g, mp=176° C.). Data for the title compound: $^1$H NMR (400 MHz, CDCl$_3$) δ 3.77 (3H, s), 5.56 (2H, s), 7.30

(1H, t, J=9 Hz), 7.40 (2H, m), 7.52 (2H, m), 7.65 (3H, m), 7.80 (1H, t, J=7.8 Hz), 7.86 (1H, s), 9.43 (1H, s); MS (ES$^+$) m/e 402 [MH]$^+$. Anal. Found C, 62.81; H, 4.10; N, 24.71%. $C_{21}H_{16}FN_7O$ requires C, 62.84; H, 4.02; N, 24.43%.

A more efficient work up procedure for this reaction is to pour the crude reaction mixture on to a silica column and elute with dichloromethane until all the Dowtherm A has been removed. Then elution with 5% methanol in dichloromethane and recrystallisation from toluene yields the pure final product. Using this procedure, 1.56 g of 1e) was converted to 0.64 g of 1f) (43%).

EXAMPLE 2

3-(2-Fluorophenyl)-7-(2-fluorophenyl)-2-(2-methyl-2H-[1,2,4]triazol-3-ylmethoxy)pyrazolo[1,5-d][1,2,4]triazine This compound was prepared in the same way as described for Example 1 except 4-hydroxy-3-(2-fluorophenyl)-2-furanone (prepared using the conditions of Thuring, *J. Chem. Soc., Perkin Trans.* 1, 1997, 767–774, starting from 2-fluorophenylacetic acid) was used instead of 4-hydroxy-3-phenyl-2-furanone in step 1a). Data for final compound: mp=169° C. $^1$H NMR (400 MHz, CDCl$_3$) δ 3.77 (3H, s), 5.54 (2H, s), 7.22–7.33 (4H, m), 7.40 (2H, m), 7.63 (2H, m), 7.82 (1H, m), 9.28 (1H, s); MS (ES$^+$) m/e 420 [MH]$^+$. Anal. Found C, 60.13; H, 3.75; N, 23.12%. $C_{21}H_{15}F_2N_7O$ requires C, 60.14; H, 3.61; N, 23.38%.

EXAMPLE 3

3-(3-Fluorophenyl)-7-(2-fluorophenyl)-2-(2-methyl-2H-[1,2,4]triazol-3-ylmethoxy)pyrazolo[1,5-d][1,2,4]triazine This compound was prepared in the same way as described for Example 1 except 4-hydroxy-3-(3-fluorophenyl)-2-furanone (prepared using the conditions of Thuring, *J. Chem. Soc., Perkin Trans.* 1, 1997, 767–774, starting from 3-fluorophenylacetic acid) was used instead of 4-hydroxy-3-phenyl-2-furanone in step 1a). Data for final compound: mp=176° C. $^1$H NMR (400 MHz, CDCl$_3$) δ 3.77 (3H, s), 5:56 (2H, s), 7.08 (1H, m), 7.30 (1H, s); m), 7.39–7.48 (4H, m), 7.68 (1H, m), 7.79 (1H, m), 7.86 (1H, s), 9.44 (1H, s); MS (ES$^+$) m/e 420 [MH]$^+$. Anal. Found C, 60.33; H, 3.70; N, 23.26%. $C_{21}H_{15}F_2N_7O$ requires C, 60.14; H, 3.61; N, 23.38%.

EXAMPLE 4

3-(4-Fluorophenyl)-7-(2-fluorophenyl)-2-(2-methyl-2H-[1,2,4]triazol-3-ylmethoxy)pyrazolo[1,5-d][1,2,4]triazine This compound was prepared in the same way as described for Example 1 except 4-hydroxy-3-(4-fluorophenyl)-2-furanone (prepared using the conditions of Thuring, *J. Chem. Soc., Perkin Trans.* 1, 1997, 767–774, starting from 4-fluorophenylacetic acid) was used instead of 4-hydroxy-3-phenyl-2-furanone in step 1a). Data for final compound: mp=192° C. $^1$H NMR (400 MHz, CDCl$_3$) δ 3.75 (3H, s), 5.55 (2H, s), 7.21 (2H, m), 7.28 (1H, m), 7.40 (1H, m), 7.61–7.67 (3H, m), 7.79 (1H, m), 7.86 (1H, s), 9.38 (1H, s); MS (ES$^+$) m/e 420 [MH]$^+$. Anal. Found C, 60.24; H, 3.66; N, 23.18%. $C_{21}H_{15}F_2N_7O$ requires C, 60.14; H, 3.61; N, 23.38%.

EXAMPLE 5

2-(2-Ethyl-2H-[1,2,4]triazol-3-ylmethoxy)-7-(2-fluorophenyl)-3-phenylpyrazolo[1,5-d][1,2,4]triazine This compound was prepared using the procedure described in Example 1, using 3-chloromethyl-2-ethyl-2H-[1,2,4]triazole hydrochloride instead of 3-chloromethyl-2-methyl-2H-[1,2,4]triazole hydrochloride in step c). Data for the title compound: mp=171–173° C.; $^1$H NMR (400 MHz, CDCl$_3$) δ 1.34 (3H, t), 4.12 (2H, q), 5.57 (.2H, s), 7.26–7.50 (5H, m), 7.66 (3H, m), 7.82 (1H, m), 7.88 (1H, s), 9.42 (1H, s); MS (ES$^+$) m/e 416 [MH]$^+$; Anal. Found: C, 63.93; H, 4.32; N, 23.44%. $C_{22}H_{18}FN_7O$ requires: C, 63.61; H, 4.37; N, 23.60%.

EXAMPLE 6

7-(2-Fluorophenyl)-2-(1-methyl-1H-[1,2,4]triazol-3-ylmethoxy)-3-phenylpyrazolo[15-d][1,2,4]triazine This compound was prepared using the procedure described in Example 1, using 3-chloromethyl-1-methyl-1H-[1,2,4]triazole hydrochloride instead of 3-chloromethyl-2-methyl-2H-[1,2,4]triazole hydrochloride in step c). Data for the title compound: mp=187–189° C.; $^1$H NMR (400 MHz, CDCl$_3$) δ 3.92 (3H, s), 5.50 (2H, s), 7.27 (2H, m), 7.36 (1H, m), 7.46 (2H, m), 7.59–7.64 (1H, m), 7.71 (2H, d), 7.83–7.87 (1H, m), 8.01 (1H, s), 9.41 (1H, s); MS (ES$^+$) m/e 402 [MH]$^+$; Anal. Found: C, 62.70; H, 3.73; N, 24.26%. $C_{21}H_{16}FN_7O$ requires: C, 62.84; H, 4.02; N, 24.43%.

EXAMPLE 7

7-(3-Fluorophenyl)-2-(2-methyl-2H-[1,2,4]triazol-3-ylmethoxy)-3-phenylpyrazolo[1,5-d][1,2,4]triazine This compound was prepared using the procedure described in Example 1, using 3-fluorobenzoic hydrazide instead of 2-fluorobenzoic hydrazide in step e). Data for the title compound: mp=198° C.; $^1$H NMR (400 MHz, CDCl$_3$) δ 3.92 (3H, s), 5.69 (2H, s), 7.35 (1H, m), 7.41 (1H, m), 7.51 (2H, m), 7.55–7.61 (1H, m), 7.65 (2H; m), 7.92 (1H, s), 8.22–8.29 (2H, m), 9.39 (1H, s); MS (ES$^+$) m/e 402 [MH]$^+$; Anal. Found: C, 62.98; H, 3.93; N, 23.96%. $C_{21}H_{16}FN_7O.0.0.05C_7H_8$ requires: C, 63.16; H, 4.07; N, 24.15%.

EXAMPLE 8

7-(2-Fluorophenyl)-3-phenyl-2-(pyridin-2-ylmethoxy)pyrazolo[1,5-d][1,2,4]triazine This compound was prepared using the procedure described in Example 1, using 2-picolyl chloride hydrochloride instead of 3-chloromethyl-2-methyl-2H-[1,2,4]triazole hydrochloride in step c). Data for the title compound: mp=182–183° C.; $^1$H NMR (400 MHz, CDCl$_3$) δ 5.57 (2H, s), 7.22–7.28 (2H, m), 7.34–7.42 (2H, m), 7.47 (1H, d, J=7.8 Hz), 7.53 (2H, t, J=7.5 Hz), 7.60–7.65 (1H, m), 7.69 (1H, t, J=7.7 Hz), 7.75–7.82 (3H, m), 8.59 (1H, d, J=4.4 Hz), 9.43 (1H, s); MS (ES$^+$) m/e 398 [MH]$^+$; Anal. Found: C, 69.75; H, 3.86; N, 17.41%. $C_{23}H_{16}FN_7O$ requires: C, 69.51; H, 4.06; N, 17.62%.

EXAMPLE 9

7-(4-Fluorophenyl)-2-(2-methyl-2H-[1,2,4]triazol-3-ylmethoxy)-3-phenylpyrazolo[1,5-d][1,2,4triazine This compound was prepared using the procedure described in Example 1, using 4-fluorobenzoic hydrazide instead of 2-fluorobenzoic hydrazide in step e). Data for the title compound: mp=198° C.; $^1$H NMR (400 MHz, CDCl$_3$) δ 3.92 (3H, s), 5.68 (2H, s), 7.29 (2H, m), 7.41 (1H, m), 7.51 (2H, m), 7.65 (2H, d), 7.91 (1H, s), 8.50–8.54 (2H, m), 9.38 (1H, s); MS (ES$^+$) m/e 402 [MH]$^+$; Anal. Found: C, 62.78;

H, 3.83; N, 24.22%. $C_{21}H_{16}FN_7O$ requires: C, 62.84; H, 4.02; N, 24.43%.

EXAMPLE 10

7-(2,6-Difluorophenyl)-2-(2-methyl-2H-[1,2,4]triazol-3-ylmethoxy)-3-phenylpyrazolo[1,5-d][1,2,4]triazine This compound was prepared using the procedure described in Example 1, using 2,6-difluorobenzoic hydrazide instead of 2-fluorobenzoic hydrazide in step e). Data for the title compound: mp=179° C.; $^1$H NMR (400 MHz, CDCl$_3$) δ 3.78 (3H, s), 5.53 (2H, s), 7.15 (2H, m), 7.40 (1H, m), 7.50 (2H, m), 7.60–7.67 (3H, m), 7.86 (1H, s), 9.45 (1H, s); MS (ES$^+$) m/e 420 MH]$^+$; Anal. Found: C, 59.10; H, 3.46; N, 22.78%. $C_{21}H_{15}F_2N_7O \cdot 0.25H_2O$ requires: C, 59.50; H, 3.69; N, 23.13%.

EXAMPLE 11

2-(2-Methyl-2H-[1,2,4]triazol-3-ylmethoxy)-3-phenyl-7-(thien-2-yl) pyrazolo[1,5-d][1,2,4]triazine This compound was prepared using the procedure described in Example 1, using 2-thiophene carboxylic acid hydrazide instead of 2-fluorobenzoic hydrazide in step e). Data for the title compound: mp=209° C.; $^1$H NMR (400 MHz, CDCl$_3$) δ 3.99 (3H, s), 5.82 (2H, s), 7.32 (1H, m), 7.40 (1H, m), 7.50 (2H, m), 7.65 (2H, d), 7.76 (1H, d), 7.93 (1H, s), 8.82 (1H, s), 9.34 (1H, s); MS (ES$^+$) m/e 390 [MH]$^+$; Anal. Found: C, 58.18; H, 3.66; N, 24.67%. $C_{19}H_{15}N_7OS \cdot 0.05\ C_7H_8 \cdot 0.25H_2O$ requires: C, 58.31; H, 4.02; N, 24.60%.

EXAMPLE 12

3,7-Diphenyl-2-(2-methyl-2H-[1,2,4]triazol-3-ylmethoxy)pyrazolo[1,5-d][1,2,4]triazine This compound was prepared using the procedure described in Example 1, using benzoic hydrazide instead of 2-fluorobenzoic hydrazide in step e). Data for the title compound: mp=185° C.; $^1$H NMR (400 MHz, CDCl$_3$) δ 3.88 (3H, s), 5.66 (2H, s), 7.40 (1H, m), 7.51 (2H, m), 7.58–7.67 (5H, m), 7.91 (1H, s), 8.40 (2H, d), 9.38 (1H, s); MS (ES$^+$) m/e 384 [MH]$^+$; Anal. Found: C, 66.10; H, 4.39; N, 25.08%. $C_{21}H_{17}N_7O \cdot 0.05\ C_7H_8$ requires: C, 66.09; H, 4.52; N, 25.27%.

EXAMPLE 13

7-(2,5-Difluorophenyl)-2-(2-methyl-2H-[1,2,4]triazol-3-ylmethoxy)-3-phenylpyrazolo[1,5-d][1,2,4]triazine This compound was prepared using the procedure described in Example 1, using 2,5-difluorobenzoic hydrazide instead of 2-fluorobenzoic hydrazide in step e). Data for the title compound: mp=199° C.; $^1$H NMR (400 MHz, CDCl$_3$) δ 3.83 (3H, s), 5.57 (2H, s), 7.24–7.37 (1H, m), 7.40 (2H, m), 7.48–7.56 (3H, m), 7.65 (2H, d), 7.87 (1H, s), 9.43 (1H, s); MS (ES$^+$) m/e 420 [MH]$^+$; Anal. Found: C, 60.35; H, 3.48; N, 23.22%. $C_{21}H_{15}F_2N_7O$ requires: C, 60.14; H, 3.61; N, 23.38%.

EXAMPLE 14

3-(2,5-Difluorophenyl)-7-(2-fluorophenyl)-2-(2-methyl-2H-[1,2,4]triazol-3-ylmethoxy)Pyrazolo[1,5-d][1,2,4]triazine This compound was prepared using the procedure described in Example 1, using 3-(2,5-difluorophenyl)-4-hydroxy-2-furanone instead of 4-hydroxy-3-phenyl-2-furanone in step a). Data for the title compound: mp=164–165° C.; $^1$H NMR (400 MHz, CDCl$_3$) δ 3.78 (3H, s), 5.55 (2H, s), 7.09 (1H, m), 7.21 (1H, m), 7.28–7.43 (3H, m), 7.66 (1H, m), 7.80 (1H, t, J=7.1 Hz), 7.86 (1H, s), 9.30 (1H, s); MS (ES$^+$) m/e 438 [MH]$^+$; Anal. Found: C, 57.85; H, 3.05; N, 21.89%. $C_{21}H_{14}F_3N_7O$ requires: C, 57.67; H, 3.23; N, 22.42%.

EXAMPLE 15

3-(2,6-Difluorophenyl)-7-(2-fluorophenyl)-2-(2-methyl-2H-[1,2,4]triazol-3-ylmethoxy)pyrazolo[1,5-d][1,2,4]triazine This compound was prepared in the same way as described for Example 1 except 3-(2,6-difluorophenyl)-4-hydroxy-2-furanone (prepared using the conditions of Thuring, *J. Chem. Soc., Perkin Trans.* 1, 1997, 767–774, starting from 2,6-difluorophenylacetic acid) was used instead of 4-hydroxy-3-phenyl-2-furanone in step 1a). Data for final compound: mp=196° C. $^1$H NMR (400 MHz, CDCl$_3$) δ 3.83 (3H, s), 5.53 (2H, s), 7.07 (2H, m), 7.31 (1H, m), 7.41 (2H, m), 7.66 (1H, m), 7.82 (2H, m), 9.16 (1H, s); MS (ES$^+$) m/e 438 [MH]$^+$. Anal. Found C, 57.57; H, 3.19; N, 22.77%. $C_{21}H_{14}F_3N_7O$ requires C, 57.67; H, 3.23; N, 22.42%.

EXAMPLE 16

3-(2,3-Difluorophenyl)-7-(2-fluorophenyl)2-(2-methyl-2H-[1,2,4]triazol-3-ylmethoxy)pyrazolo[1,5-d][1,2,4]triazine This compound was prepared in the same way as described for Example 1 except 3-(2,3-difluorophenyl)-4-hydroxy-2-furanone (prepared using the conditions of Thuring, *J. Chem. Soc., Perkin Trans.* 1, 1997, 767–774, starting from 2,3-difluorophenylacetic acid) was used instead of 4-hydroxy-3-phenyl-2-furanone in step 1a). Data for final compound: mp=176° C. $^1$H NMR (400 MHz, CDCl$_3$) δ 3.78 (3H, s), 5.54 (2H, s), 7.19–7.43 (5H, m), 7.65 (1H, m), 7.80 (1H, m), 7.85 (1H, s), 9.29 (1H, s); MS (ES$^+$) m/e 438 [MH]$^+$. Anal. Found C, 57.50; H, 3.17; N, 22.22%. $C_{21}H_{14}F_3N_7O$ requires C, 57.67; H, 3.23; N, 22.42%.

EXAMPLE 17

3-Bromo-7-(2-fluorophenyl)-2-(2-methyl-2H-[1,2,4]triazol-3-ylmethoxy)pyrazolo[1,5-d][1,2,4]triazine a) Toluene-4-sulfonic Acid 5-Hydroxymethyl-1H-pyrazol-3-yl Ester To a stirred suspension of 5-hydroxymethyl-1H-pyrazol-3-ol (*J. Heterocycl. Chem.*, 1979, 16, 505–508) (1.0245 g, 8.98 mmol) in anhydrous dichloromethane (50 ml), under nitrogen, was added p-toluenesulfonyl chloride (1.8825 g, 9.87 mmol), then, dropwise over 5 min, anhydrous triethylamine (1.50 ml, 10.8 mmol). The mixture was stirred at room temperature for 16.5 h under nitrogen, then washed with brine (50 ml). The aqueous layer was further extracted with dichloromethane, and the combined organic extracts were dried (Na$_2$SO$_4$) and evaporated in vacuo. The residue was purified by flash chromatography (silica gel, 5–7% MeOH/CH$_2$Cl$_2$) to afford 1.3067 g (54%) of the title compound as a pale green solid; $^1$H NMR (360 MHz, d$_6$-DMSO) δ 2.42 (3H, s), 4.38 (2H, d, J=5.7 Hz), 5.32 (1H, t, J=5.7 Hz), 5.82 (1H, d, J=2.2 Hz), 7.47 (2H, d, J=8.3 Hz), 7.77 (2H, d, J=8.3 Hz), 12.55 (1H, s).

b) Toluene-4-sulfonic Acid 7-(2-Fluorophenyl)pyrazolo[1,5-d][1,2,4]triazin-2-yl Ester To a solution of toluene-4-sulfonic acid 5-hydroxymethyl-1H-pyrazol-3-yl ester (25 g, 93 mmol) in chloroform (800 ml) was added manganese dioxide (40.3 g, 465 mmol) and the suspension was heated at 70° C. for 14 h. The reaction mixture was filtered through sand/silica and the plug of silica was then washed several times with 10% methanol/dichloromethane. The combined filtrates were concentrated under vacuum to give crude aldehyde (25 g). Some of the crude aldehyde (2 g, 7.6 mmol) and 2-fluorobenzoic hydrazide (1.16 g, 7.6 mmol) were suspended in xylene (60 ml) and heated together at reflux for 3 h. After cooling, the solid formed was collected by filtration and dried under vacuum at 80° C. to afford 2.7 g (94%) of the condensation product as a light brown solid. Some of this condensation product, which existed in nmr solution as a mixture of isomers (1 g, 2.5 mmol), was dissolved in Dowtherm A (100 ml) and heated at 180° C. for 72 h. The whole reaction solution was cooled and eluted through a silica gel column using 0 to 15% ethyl acetate/dichloromethane to give the title compound as a light tan solid (0.614 g, 64%); $^1$H NMR (360 MHz, CDCl$_3$) δ 2.46 (3H, s), 6.73 (1H, s), 7.18–7.35 (4H, m), 7.61 (1H, m), 7.71 (1H, m), 7.82 (2H, d, J 8.3 Hz), 9.33 (1H, s).

c) 7-(2-Fluorophenyl)pyrazolo[1,5-d][1,2,4]triazin-2-ol

To a stirred solution of toluene-4-sulfonic acid 7-(2-fluorophenyl)pyrazolo[1,5-d][1,2,4]triazin-2-yl ester (82.0 mg, 0.213 mmol) in 1,4-dioxane (4 ml) and water (0.8 ml) was added aqueous 4 N NaOH solution (0.270 ml, 1.08 mmol). The solution was heated at 60° C. for 3 h, then the solvents were removed in vacuo. The residue was dissolved in water (10 ml) and washed with ethyl acetate (10 ml). The aqueous layer was acidified to pH<3 and extracted with dichloromethane (6×25 ml). The combined organic extracts were dried (Na$_2$SO$_4$) and evaporated in vacuo to leave 40.7 mg (83%) of the title compound; $^1$H NMR (360 MHz, d$_6$-DMSO) δ 6.34 (1H, s), 7.42–7.48 (2H, m), 7.71 (1H, m), 7.79 (1H, td, J 7.2 and 1.7 Hz), 9.40 (1H, s), 11.74 (1H, s).

d) 3-Bromo-7-(2-Fluorophenyl)pyrazolo[1,5-d][1,2,4]triazin-2-ol

To a stirred mixture of 7-(2-fluorophenyl)pyrazolo[1,5-d][1,2,4]triazin-2-ol (0.2508 g, 1.09 mmol) in glacial acetic acid (5 ml) was added dropwise bromine (62 μl, 1.20 mmol) and the mixture was stirred at room temperature for 2.25 h. Water (20 ml) was then added and the resulting solid was collected by filtration, washed with water, and dried under vacuum at 50° C. to yield 0.3054 g (91%) of the title compound as a buff solid; $^1$H NMR (360 MHz, d$_6$-DMSO) δ 7.43–7.50 (2H, m), 7.72 (1H, m), 7.80 (1H, m), 9.40 (1H, s), 12.67 (1H, s).

e) 3-Bromo-7-(2-Fluorophenyl)-2-(2-methyl-2H-[1,2,4]triazol-3-ylmethoxypyrazolo[1,5-d][1,2,4]triazine To a stirred solution of 3-bromo-7-(2-fluorophenyl)pyrazolo[1,5-d][1,2,4]triazin-2-ol (0.2073 g, 0.671 mmol) in anhydrous DMF (10 ml) under nitrogen was added cesium carbonate (0.8731 g, 2.680 mmol), then solid 3-chloromethyl-2-methyl-2H-[1,2,4]triazole hydrochloride (0.1703 g, 1.014 mmol). The mixture was stirred at room temperature for 22.5 h, then at 60° C. for 2.33 h. This was then partitioned between water (40 ml) and ethyl acetate (40 ml). The aqueous layer was further extracted with ethyl acetate (2×40 ml), and the combined organic extracts were dried (Na$_2$SO$_4$) and evaporated in vacuo. The residue was purified by flash chromatography (silica gel, EtOAc) to give 0.2299 g (85%) of the title compound as a white solid: mp=215–219° C. (CH$_2$Cl$_2$-EtOAc-isohexane); $^1$H NMR (360 MHz, CDCl$_3$) δ 3.87 (3H, s), 5.52 (2H, s), 7.28 (1H, m), 7.39 (1H, t, J=7.5 Hz), 7.65 (1H, m), 7.77 (1H, t, J=7.5 Hz), 7.87 (1H, s), 9.22 (1H, s); MS (ES$^+$) m/e 404/406 [MH]$^+$. Anal. Found C, 44.41; H, 2.53; N, 24.04%. C$_{15}$H$_{11}$BrFN$_7$O requires C, 44.57; H, 2.74; N, 24.26%.

EXAMPLE 18

7-(2-Fluorophenyl)-2-(2-methyl-2H-[1,2,4]triazol-3-ylmethoxy)-3-[3-(trifluoromethyl)phenyl]pyrazolo[1,5-d][1,2,4]triazine A mixture of 3-bromo-7-(2-fluorophenyl)-2-(2-methyl-2H-[1,2,4]triazol-3-ylmethoxy)pyrazolo[1,5-d][1,2,4]triazine (60.2 mg, 0.149 mmol), 3-trifluoromethylbenzeneboronic acid (42.3 mg, 0.223 mmol) and cesium carbonate (96.9 mg, 0.297 mmol) in anhydrous 1,4-dioxane (5 ml) was degassed using three freeze-pump-thaw cycles. Tris(dibenzylideneacetone)palladium(0) (13.8 mg, 0.0151 mmol) and a 0.1 M solution of tri-tert-butylphosphine in 1,4-dioxane (0.357 ml, 0.357 mmol) was added, and the mixture was further degassed with two more freeze-pump-thaw cycles before heating at 90° C. under nitrogen for 17 h. The mixture was filtered through glass fibre paper, washing well with ethyl acetate (25 ml). The filtrate was washed with saturated aqueous NaCl (10 ml), and the aqueous layer was further extracted with ethyl acetate (25 ml). The combined organic extracts were dried (Na$_2$SO$_4$) and evaporated in vacuo. The residue was purified by flash chromatography (silica gel, 2% MeOH/CH$_2$Cl$_2$) to give 56.3 mg (81%) of the title compound as a yellow solid: mp=152–155° C. (EtOAc-isohexane); $^1$H NMR (360 MHz, CDCl$_3$) δ 3.79 (3H, s), 5.58 (2H, s), 7.31 (1H, m), 7.41 (1H, td, J=7.6 and 0.9 Hz), 7.63–7.68 (3H, m), 7.80 (1H, m), 7.85–7.86 (2H, m), 7.93 (1H, s), 9.44 (1H, s); MS (ES$^+$) m/e 470 [MH]$^+$. Anal. Found C, 56.22; H, 3.35; N, 20.59%. C$_{22}$H$_{15}$F$_4$N$_7$O requires C, 56.29; H, 3.22; N, 20.89%.

EXAMPLE 19

7-(2-Fluorophenyl)-2-(2-methyl-2H-[1,2,4]triazol-3-ylmethoxy)-3-(thien-3-l)pyrazolo[1,5-d][1,2,4]triazine This was prepared in 91% yield using a similar procedure to that described in Example 18 except using thiophene-3-boronic acid instead of 3-trifluoromethylbenzeneboronic acid. Data for title compound: mp=208–209° C. (CH$_2$Cl$_2$-EtOAc); $^1$H NMR (360 MHz, CDCl$_3$) δ 3.79 (3H, s), 5.57 (2H, s), 7.29 (1H, m), 7.40 (1H, t, J=7.6 Hz), 7.49 (1H, s), 7.50 (1H, s), 7.64–7.67 (2H, m), 7.79 (1H, m), 7.87 (1H, s), 9.46 (1H, s); MS (ES$^+$) m/e 408 [MH]$^+$. Anal. Found C, 55.44; H, 3.22; N, 23.68%. C$_{19}$H$_{14}$FN$_7$OS.0.04CH$_2$Cl$_2$ requires C, 55.67; H, 3.45; N, 23.87%.

EXAMPLE 20

3-(3,5-Difluorophenyl)-7-(2-fluorophenyl)-2-(2-methyl-2H-[1,2,4]triazol-3-ylmethoxy)pyrazolo[1,5-d][1,2,4]triazine This compound was prepared using the procedure described in Example 1, using 3-(3,5-difluorophenyl)-4-hydroxy-2-furanone instead of 4-hydroxy-3-phenyl-2-furanone in step a). Data for the title compound: mp=171–173° C.; $^1$H NMR (400 MHz, CDCl$_3$) δ 3.77 (3H, s), 5.57 (2H, s), 6.85 (1H, m), 7.22 (2H, dd, J=8.1, 2.1 Hz), 7.31 (1H, t, J=9.1 Hz), 7.41 (1H, td, J=7.6, 0.6 Hz), 7.67 (1H, m), 7.79 (1H, td, J=7.2, 1.6 Hz), 7.87 (1H, s), 9.45 (1H, s); MS (ES$^+$) m/e 438 [MH]$^+$; Anal. Found: C, 57.53; H, 3.32; N, 21.88%. $C_{21}H_{14}F_3N_7O$ requires: C, 57.67; H, 3.23; N, 22.42%.

EXAMPLE 21

7-(2,5-Difluorophenyl)-3-(1,1-dimethylethyl)-2-(2-methyl-2H-[1,2,4]triazol-3-ylmethoxy)pyrazolo[1,5-d][1,2,4]triazine a) 3-tert-Butyl-4-hydroxy-2-furanone To 4-hydroxy-2-furanone (50 g, 0.5 mol) in tert-butanol (50 ml, 0.53 mol) was added concentrated sulfuric acid (25 ml). The mixture was heated at 40° C. for 20 h then allowed to cool. Water (250 ml) was added and the mixture was extracted with diethyl ether (3×250 ml), the diethyl ether layers were combined, washed with brine (250 ml), dried ($Na_2SO_4$), filtered and concentrated in vacuo to give a brown solid. The solid was purified by silica gel chromatography with 0%→100% ethyl acetate/isohexane as eluent followed by two recrystallisations from ethyl acetate/isohexane (1:1) to afford the required product (5.75 g). Data for the title compound: $^1$H NMR (400 MHz, DMSO) δ 1.21 (9H, s), 4.48 (2H, s), 11.40 (1H, s); MS (ES$^+$) m/e 156 [MH]$^+$.

b) 4-tert-Butyl-5-hydroxymethylpyrazol-3-one 3-tert-Butyl-4-hydroxy-2-furanone, (5.75 g, 0.037 mol) was dissolved in ethanol (50 ml) with hydazine monohydrate (8.93 ml, 0.184 mol) and heated at reflux for 2 days. The solution was allowed to cool and the solvent was removed in vacuo. The residue was azeotroped successively with toluene, methanol, dichloromethane and finally isohexane to give the title compound as a solid (6.25 g). Data for the title compound: $^1$H NMR (360 MHz, DMSO) δ 1.26 (9H, s), 4.41 (2H, s), 5.00 (1H, bs), 10.90 (1H, bs); MS (ES$^+$) m/e 171 [MH]$^+$.

c) 4-tert-Butyl-5-hydroxymethyl-3-(p-toluenesulfonyloxy) pyrazole

To a suspension of 4-tert-butyl-5-hydroxymethylpyrazol-3-one (6.25 g, 0.037 mol) in dry dichloromethane (200 ml) was added p-toluene sulfonyl chloride (9.8 g, 0.051 mol) followed by triethylamine (6.14 ml, 0.044 mol) dropwise. The solution was stirred at room temperature for 3 days. Dichloromethane (250 ml) was then added to dilute and the solution was washed with brine (250 ml), dried ($MgSO_4$), filtered and concentrated in vacuo. The residue was purified by silica gel chromatography with 0%→30% ethyl acetate/dichloromethane as eluent to give the title compound (7.5 g). Data for the title compound: $^1$H NMR (400 MHz, DMSO) δ 1.28 (9H, s), 2.43 (3H, s), 4.49 (2H, m), 5.32 (1H, m), 7.47 (2H, m), 7.86 (2H, m), 12.28 (1H, s); MS (ES$^+$) m/e 325 [MH]$^+$.

d) 4-tert-Butyl-5-formyl-3-(p-toluenesulfonyloxy)pyrazole

This compound was prepared by the procedure described in Example 1, step d) using the product from Example 21, step c) instead of 5-hydroxymethyl-3-(2-methyl-2H-[1,2,4]triazol-3-ylmethoxy)-4-phenylpyrazole. Data for the title compound: $^1$H NMR (400 MHz, DMSO) δ 1.33+1.39 (9H, s+s) (tautomers present), 2.44 (3H, m), 6.55 (0.6H, m) (proton due to presence of aldehyde hydrate), 7.49–7.53 (2H, m), 7.79–7.98 (2H, m), 10.03 (0.2H, s) (tautomers present), 13.68 (0.2H, s); MS (ES$^+$) m/e 323 [MH]$^+$.

e) 3-tert-Butyl-7-(2,5-difluorophenyl)-2-(p-toluenesulfonyloxy)pyrazolo[1,5-d][1,2,4]triazine The product from Example 21, step d) (2 g, 0.062 mol) was suspended in xylene (60 ml) and 2,5-difluorobenzoic hydrazide (1.18 g, 0.068 mol) and triethylamine hydrochloride (0.85 g, 0.062 mol) were added. The suspension was heated at reflux for 3 days. Solvent was removed in vacuo and the residue was purified using silica gel chromatography with 0%→5% ethyl acetate/dichloromethane as eluent to give the required product (2.34 g). Data for the title compound: $^1$H NMR (360 MHz, CDCl$_3$) δ 1.58 (9H, s), 2.44 (3H, s), 7.20–7.23 (3H, m), 7.28–7.42 (2H, m), 7.85 (2H, d), 9.49 (1H, s); MS (ES$^+$) m/e 459 [MH]$^+$.

f) 7-(2,5-Difluorophenyl)-3-(1,1-dimethylethyl)-2-(2-methyl-2H-[1,2,4]triazol-3-ylmethoxy)pyrazolo[1,5-d][1,2,4]triazine The product from Example 21, step e) (0.4 g, 0.0009 mol) and (2-methyl-2H-[1,2,4]triazol-3-yl)methanol (0.12 g, 0.0011 mol) were dissolved in dry N,N-dimethylformamide (10 ml) under nitrogen and sodium hydride (60% wt in oil) (0.035 g, 0.0009 mol) was added. The solution was stirred at room temperature for 3 h after which solvent was removed in vacuo and the residue was purified using silica gel chromatography with 0%→60% ethyl acetate/dichloromethane as eluent. Trituration with isohexane and recrystallisation from ethyl acetate/isohexane gave the required product (0.137 g, mp=144° C.). Data for the title compound: $^1$H NMR (400 MHz, CDCl$_3$) δ 1.50 (9H, s), 3.84 (3H, s), 5.48 (2H, s), 7.18–7.26 (1H, m), 7.27–7.35 (1H, m), 7.47 (1H, m), 7.87 (1H, s), 9.41 (1H, s); MS (ES$^+$) m/e 400 [MH]$^+$; Anal. Found: C, 57.30; H, 4.64; N, 24.64%. $C_{19}H_{19}F_2N_7O$ requires: C, 57.14; H, 4.79; N, 24.55%.

EXAMPLE 22

7-(2,5-Difluorophenyl)-3-(1,1-dimethylethyl)-2-(2-ethyl-2H-[1,2,4]triazol-3-ylmethoxy)pyrazolo[1,5-d][1,2,4]triazine This compound was prepared using the procedure described in Example 21, using (2-ethyl-2H-[1,2,4]triazol-3-yl)methanol instead of (2-methyl-2H-[1,2,4]triazol-3-yl)methanol in step f). Data for the title compound: mp=108° C.; $^1$H NMR (360 MHz, CDCl$_3$) δ 1.42 (3H, m), 1.49 (9H, s), 4.18 (2H, m), 5.48 (2H, s), 7.18–7.35 (2H, m), 7.48 (1H, m), 7.90 (1H, s), 9.41 (1H, s); MS (ES$^+$) m/e 414 [MH]$^+$; Anal. Found: C, 57.88; H, 5.06; N, 23.47%. $C_{20}H_{21}F_2N_7O$ requires: C, 58.10; H, 5.12; N, 23.72%.

EXAMPLE 23

7-(2 5-Difluorophenyl)-3-(1,1-dimethylethyl)-2-(2-propyl-2H-[1,2,4]triazol-3-ylmethoxy)pyrazolo[1,5-d][1,2,4]triazine This compound was prepared using the procedure described in Example 21, using (2-propyl-2H-[1,2,4]triazol-3-yl)methanol instead of (2-methyl-2H-[1,2,4]triazol-3-yl)methanol in step f). Data for the title compound: mp=92° C.; $^1$H NMR (400 MHz, CDCl$_3$) δ 0.87 (3H, t), 1.49 (9H, s), 1.86 (2H, m), 4.08 (2H, t), 5.47 (2H, s), 7.17–7.34 (2H, m), 7.48 (1H, m), 7.90 (1H, s), 9.41 (1H, s); MS (ES$^+$) m/e 428 [MH]$^+$; Anal. Found: C, 55.36; H, 5.14; N, 21.08%. $C_{21}H_{23}F_2N_7O.0.0.5CH_2Cl_2$ requires: C, 54.95; H, 5.15; N, 20.86%.

EXAMPLE 24

3-(1,1-Dimethylethyl)-7-(2-fluorophenyl)-2-(2-methyl-2H-[1,2,4]triazol-3-ylmethoxy)pyrazolo[1,5-d][1,2,4]triazine This compound was prepared using the procedure described in Example 21, using 2-fluorobenzoic hydrazide instead of 2,5-difluorobenzoic hydrazide in step e). Data for the title compound: mp=128° C.; $^1$H NMR (400 MHz, CDCl$_3$) δ 1.50 (9H, s), 3.76 (3H, s), 5.46 (2H, s), 7.26 (1H, m), 7.36 (1H, m), 7.61 (1H, m), 7.73 (1H, m),:7.86 (1H, s), 9.40 (1H, s); MS (ES$^+$) m/e 382 [MH]$^+$; Anal. Found: C, 60.03; H, 5.23; N, 25.35%. C$_{19}$H$_{20}$FN$_7$O requires: C, 59.83; H, 5.29; N, 25.71%.

EXAMPLE 25

3-(1,1-Dimethylethyl)-2-(2-ethyl-2H-[1,2,4]triazol-3-ylmethoxy)-7-(2-fluorophenyl)pyrazolo[1,5-d][1,2,4]triazine This compound was prepared using the procedure described in Example 21, using 2-fluorobenzoic hydrazide instead of 2,5-difluorobenzoic hydrazide in step e) and (2-ethyl-2H-[1,2,4]triazol-3-yl)methanol instead of (2-methyl-2H-[1,2,4]triazol-3-yl)methanol in step f). Data for the title compound: mp=105° C.; $^1$H NMR (360 MHz, CDCl$_3$) δ 1.38 (3H, t), 1.49 (9H, s), 4.13 (2H, q), 5.47 (2H, s), 7.26 (1H, dt), 7.36 (1H, dt), 7.61 (1H, m), 7.73 (1H, dt), 7.88 (1H, s), 9.41 (1H, s); MS (ES$^+$) m/e 396 [MH]$^+$; Anal. Found: C, 60.82; H, 5.46; N, 24.59%. C$_{20}$H$_{22}$FN$_7$O requires: C, 60.75; H, 5.61; N, 24.79%.

EXAMPLE 26

3-(1,1-Dimethylethyl)-7-(2-fluorophenyl)-2-(2-propyl-2H-[1,2,4]triazol-3-ylmethoxy)pyrazolo[1,5-d][1,2,4]triazine This compound was prepared using the procedure described in Example 21, using 2-fluorobenzoic hydrazide instead of 2,5-difluorobenzoic hydrazide in step e) and (2-propyl-2H-[1,2,4]triazol-3-ylmethanol instead of (2-methyl-2H-[1,2,4]triazol-3-yl)methanol in step f). Data for the title compound: mp=93° C.; $^1$H NMR (360 MHz, CDCl$_3$) δ 0.85 (3H, m), 1.49 (9H,s), 1.82 (2H, m), 4.02 (2H, m), 5.46 (2H, s), 7.26 (1H, m), 7.36 (1H, m), 7.61 (1H, m), 7.73 (1H, m), 7.88 (1H, s), 9.40 (1H, s); MS (ES$^+$) m/e 410 [MH]$^+$; Anal. Found: C, 61.35; H, 5.81; N. 23.88%. C$_{21}$H$_{24}$FN$_7$O requires: C, 61.60; H, 5.91; N, 23.95%.

EXAMPLE 27

7-(2,5-Difluorophenyl)-3-(1,1-dimethylpronyl)-2-(2-methyl-2H-[1,2,4]triazol-3-ylmethoxy)pyrazolo[1,5-d][1,2,4]triazine This compound was prepared using the procedure described in Example 21, using tert-amyl alcohol instead of tert-butanol in step a). Data for the title compound: mp=130–131° C.; $^1$H NMR (400 MHz, CDCl$_3$) δ 0.77 (3H, t, J=7.2 Hz), 1.48 (6H, s), 1.79 (2H, q, J=7.4 Hz), 3.83 (3H, s), 5.46 (2H, s), 7.23–7.31 (2H, m), 7.49 (1H, m), 7.87 (1H, s), 9.37 (1H, s,); MS (ES$^+$) m/e 414 [MH]$^+$.

EXAMPLE 28

3-(1,1-Dimethylethyl)-2-(2-methyl-2H-[1,2,4] triazol-3-ylmethoxy)-7-(2,3,6-trifluorolphenyl) pyazolo[1,5-d][1,2,4]triazine This compound was prepared using the procedure described in Example 21, using 2,3,6-trifluorobenzoic hydrazide (prepared as described in Example 43, step a)) instead of 2,5-difluorobenzoic hydrazide in step e). Data for the title compound: mp=159° C.; $^1$H NMR (500 MHz, CDCl$_3$) δ 1.51 (9H, s), 3.85 (3H, s), 5.45 (2H, s), 7.06 (1H, m), 7.42 (1H, m), 7.87 (1H, s), 9.44 (1H, s); MS (ES$^+$) m/e 418 [MH]$^+$; Anal. Found: C, 54.77; H, 4.34; N, 23.38%. C$_{19}$H$_{18}$F$_3$N$_7$O requires: C, 54.67; H, 4.35; N, 23.49%.

EXAMPLE 29

3-(1,1-Dimethylethyl)-2-(2-ethyl-2H-[1,2,4]triazol-3-ylmethoxy)-7-(2,3,6-trifluorophenyl)pyrazolo[1,5-d][1,2,4]triazine This compound was prepared using the procedure described in Example 21, using 2,3,6-trifluorobenzoic hydrazide (prepared as described in Example 43, step a)) instead of 2,5-difluorobenzoic hydrazide in step e) and (2-ethyl-2H-[1,2,4]triazol-3-yl)methanol instead of (2-methyl-2H-[1,2,4]triazol-3-yl)methanol in step f). Data for the title compound: mp=42° C.; $^1$H NMR (400 MHz, CDCl$_3$) δ 1.43 (3H, t, J=7.2 Hz), 1.50 (9H, s), 4.18 (2H, q, J=7.2 Hz), 5.45 (2H, s), 7.16 (1H, m), 7.41 (1H, m), 7.89 (1H, s), 9.44 (1H, s); MS (ES$^+$) m/e 432 [MH]$^+$.

EXAMPLE 30

7-(2,5-Difluorophenyl)-3-(1,1-dimethylethyl)-2-(2-isopropyl-2H-[1,2,4]triazol-3-ylmethoxy)pyrazolo[1,5-d][1,2,4]triazine This compound was prepared using the procedure described in Example 21, using (2-isopropyl-2H-[1,2,4]triazol-3-yl)methanol instead of (2-methyl-2H-[1,2,4]triazol-3-yl)methanol in step f). Data for the title compound: mp=163° C.; $^1$H NMR (400 MHz, CDCl$_3$) δ 1.46 (6H, m), 1.48 (9H, s), 4.68 (1H, m), 5.49 (2H, s), 7.19–7.33 (2H, m), 7.50 (1H, m), 7.92 (1H, s), 9.42 (1H, s); MS (ES$^+$) m/e 428 [MH]$^+$; Anal. Found: C, 58.85; H, 5.31; N, 22.94%. C$_{21}$H$_{23}$F$_2$N$_7$O requires: C, 59.01; H, 5.42; N, 22.94%.

EXAMPLE 31

3-(2-Fluorophenyl)-2-(2-methyl-2H-[1,2,4]triazol-3-ylmethoxy)-7-(pyrazin-2-yl)pyrazolo[1,5-d][1,2,4]triazine Data for the title compound: mp 179–180° C.; $^1$H NMR (360 MHz, CDCl$_3$) δ 3.91 (3H, s), 5.64 (2H, s), 7.28 (2H, m), 7.41 (1H, mn), 7.59 (1H, m), 7.88 (2H, s), 8.89 (1H, s), 9.31 (1H, s), 9.54 (1H, s); MS (ES$^+$) m/e 404 [MH]$^+$; Anal. Found: C, 56.35; H, 3.28; N, 30.58%. C$_{19}$H$_{14}$FN$_9$O.0.1EtOAc requires: C, 56.53; H, 3.62; N, 30.58%.

EXAMPLE 32

3-(2-Chlorophenyl)-7-(2-fluorophenyl)-2-(2-methyl-2H-[1,2,4]triazol-3-ylmethoxy)pyrazolo[1,5-d][1,2,4]triazine This was prepared using a similar procedure to that described in Example 18 except using 2-chlorobenzeneboronic acid instead of 3-trifluoromethylbenzeneboronic acid. Data for title compound: $^1$H NMR (360 MHz, DMSO-d$_6$) δ 3.66 (3H, s), 5.48 (2H, s), 7.48–7.55 (4H, mn), 7.62–7.68 (2H, m), 7.79 (1H, m), 7.85–7.90 (2H, m), 9.38 (1H, s); MS (ES$^+$) m/e 436/438 [MH]$^+$.

EXAMPLE 33

7-(2,5-Difluorophenyl)-3-(1,1-dimethylpropyl)-2-(2-ethyl-2H-[1,2,4]triazol-3-ylmethoxy)pyrazolo[1,5-d][1,2,4]triazine This compound was prepared using the procedure described in Example 27, using (2-ethyl-2H-[1,2,4]triazol- 3-yl)methanol instead of (2-methyl-2H-[1,2,4]triazol-3-yl) methanol. Data for the title compound: mp=85–86° C.; $^1$H NMR (400 MHz, CDCl$_3$) δ 0.77 (3H, t, J=7.5 Hz), 1.42 (3H, t, J=7.3 Hz), 1.48 (6H, s), 1.79 (2H, q, J=7.5 Hz), 4.17 (2H, q, J=7.3 Hz), 5.53 (2H, s), 7.23 (1H, m), 7.32 (1H, m), 7.47 (1H, m), 7.98 (1H, s), 9.43 (1H, s); MS (ES$^+$) m/e 428 [MH]$^+$.

EXAMPLE 34

3-(1,1-Dimethylpropyl)-7-(2-fluorophenyl)-2-(2-methyl-2H-[1,2,4]triazol-3-ylmethoxy)pyrazolo[1,5-d][1,2,4]triazine This compound was prepared using the procedure described in Example 27, using 2-fluorobenzoic hydrazide instead of 2,5-difluorobenzoic hydrazide. Data for the title compound: mp=89–91° C.; $^1$H NMR (400 MHz, CDCl$_3$) δ 0.77 (3H, t, J=7.5 Hz), 1.48 (6H, s), 1.80 (2H, q, J=7.5 Hz), 3.75 (3H, s), 5.47 (2H, s), 7.26 (1H,:m), 7.37 (1H, t, J=7.5 Hz), 7.62 (1H, m), 7.74 (1H, m), 7.89 (1H, s), 9.39 (1H, s); MS (ES$^+$) m/e 396 [MH]$^+$.

EXAMPLE 35

7-(2-Fluorophenyl)-2-(2-methyl-2H-[1,2,4]triazol-3-ylmethoxy)-3-(pyridin-3-yl)pyrazolo[1,5-d][1,2,4]triazine This was prepared in 31% yield using a similar procedure to that described in Example 18 except using pyridine-3-boronic acid, 1,3-propanediol cyclic ester instead of 3-trifluoromethylbenzeneboronic acid. Data for title compound: mp=181–183° C.; $^1$H NMR (400 MHz, CDCl$_3$) δ 3.77 (3H, s), 5.57 (2H, s), 7.31 (1H, m), 7.40–7.46 (2H, m), 7.67 (1H, m), 7.80 (1H, m), 7.86 (1H, s), 8.01 (1H, dt, J=7.9 and 1.8 Hz), 8.63 (1H, m), 8.95 (1H, s), 9.49 (1H, s); MS (ES$^+$) m/e 403 [MH]$^+$.

EXAMPLE 36

3-(2-Fluorophenyl)-7-(furan-2-yl)-2-(2-methyl-2H-[1,2,4]triazol-3-ylmethoxy)pyrazolo[1,5-d][1,2,4]triazine Data for the title compound: mp=204–206° C.; $^1$H NMR (400 MHz, CDCl$_3$) δ 3.98 (3H, s), 5.77 (2H, s), 6.71 (1H, d, J=3.4 Hz), 7.27 (2H, m), 7.42 (1H, m), 7.56 (1H, s), 7.84 (1H, d, J=3.4 Hz), 7.91 (1H, s), 8.25 (1H, s), 9.19 (1H, s); MS (ES$^+$) m/e 392 [MH]$^+$; Anal. Found: C, 57.97; H, 3.25; N, 24.97%. C$_{19}$H$_{14}$FN$_7$O$_2$ requires: C, 58.31; H, 3.61; N, 25.05%.

EXAMPLE 37

3-(1,1-Dimethylethyl)-7-(4-fluorophenyl)-2-(2-methyl-2H-[1,2,4]triazol-3-ylmethoxy)pyrazolo[1,5-d][1,2,4]triazine This compound was prepared using the procedure described in Example 21, using 4-fluorobenzoic hydrazide instead of 2,5-difluorobenzoic hydrazide in step e). Data for the title compound: mp=197° C.; $^1$H NMR (400 MHz, CDCl$_3$) δ 1.51 (9H, s), 3.94 (3H, s), 5.58 (2H, s), 7.25 (2H, m), 7.92 (1H, s), 8.41 (2H, m), 9.37 (1H, s); MS (ES$^+$) m/e 382 [MH]$^+$; Anal. Found: C, 59.51; H, 5.23; N, 25.35%. C$_{19}$H$_{20}$FN$_7$O requires: C, 59.83; H, 5.29; N, 25.71%.

EXAMPLE 38

3-(1,1-Dimethylethyl)-2-(2-ethyl-2H-[1,2,4]triazol-3-ylmethoxy)-7-(4-fluorophenyl)pyrazolo[1,5-d][1,2,4]triazine This compound was prepared using the procedure described in Example 21, using 4-fluorobenzoic hydrazide instead of 2,5-difluorobenzoic hydrazide in step e) and (2-ethyl-2H-[1,2,4]triazol-3-yl)methanol instead of (2-methyl-2H-[1,2,4]triazol-3-yl)methanol in step f). Data for the title compound: mp=190° C.; $^1$H NMR (400 MHz, CDCl$_3$) δ 1.47 (3H, t, J=7.5 Hz), 1.50 (9H, s), 4.26 (2H, q, J=7.5 Hz), 5.58 (2H, s), 7.25 (2H, m), 7.94 (1H, s), 8.44 (2H, m), 9.37 (1H, s); MS (ES$^+$) m/e 396 [MH]$^+$; Anal. Found: C, 60.52; H, 5.59; N, 24.79%. C$_{20}$H$_{22}$FN$_7$O requires: C, 60.75; H, 5.61; N, 24.79%.

EXAMPLE 39

3-(1,1-Dimethylethyl)-7-(4-fluorophenyl)-2-(2-propyl-2H-[1,2,4]triazol-3-ylmethoxy)pyrazolo[1,5-d][1,2,4]triazine This compound was prepared using the procedure described in Example 21, using 4-fluorobenzoic hydrazide instead of 2,5-difluorobenzoic hydrazide in step e) and (2-propyl-2H-[1,2,4]triazol-3-yl)methanol instead of (2-methyl-2H-[1,2,4]triazol-3-yl)methanol in step f). Data for the title compound: mp=154° C.; $^1$H NMR (400 MHz, CDCl$_3$) δ 0.91 (3H, t, J=7.5 Hz), 1.50 (9H, s), 1.91 (2H, m), 4.15 (2H,:m), 5.57 (2H, s), 7.25 (2H, m), 7.94 (1H, s), 8.44 (2H, m), 9.37 (1H, s); MS (ES$^+$) m/e 410 [MH]$^+$; Anal. Found: C, 61.48; H, 5.88; N, 23.87%. C$_{21}$H$_{24}$FN$_7$O requires: C, 61.60; H, 5.91; N, 23.95%.

EXAMPLE 40

3-(1,1-Dimethylpropyl)-2-(2-ethyl-2H-[1,2,4]triazol-3-ylmethoxy)-7-(2-fluorophenyl)pyrazolo[1,5-d][1,2,4]triazine This compound was prepared using the procedure described in Example 34, using (2-ethyl-2H-[1,2,4]triazol-3-yl)methanol instead of (2-methyl-2H-[1,2,4]triazol-3-yl) methanol. Data for the title compound: mp=89–92° C.; $^1$H NMR (400 MHz, CDCl$_3$) δ 0.77 (3H, t, J=7.0 Hz), 1.37 (3H, t, J=6.8 Hz), 1.48 (6H, s), 1.79 (2H, q, J=7.2 Hz), 4.10 (2H, q, J=6.8 Hz), 5.51 (2H, s), 7.26 (1H, m), 7.37 (1H, m),: 7.63 (1H, mn), 7.75 (1H, mn), 7.96 (1H, s), 9.43 (1H, s); MS (ES$^+$) m/e 410 [MH]$^+$.

EXAMPLE 41

3-(2-Fluorophenyl)-7-(4-fluorophenyl)-2-(2-methyl-2H-[1,2,4]-triazol-3-ylmethoxy)pyrazolo[1,5-d][1,2,4]triazine This compound was prepared using the procedure described in Example 21, steps b) to f), using 3-(2-fluorophenyl)-4-hydroxy-2-furanone (cf. Example 2) instead of 3-tert-butyl-4-hydroxy-2-furanone and 4-fluorobenzoic hydrazide instead of 2,5-difluorobenzoic hydrazide in step e). Data for the title compound: mp=191° C.; $^1$H NMR (400 MHz, CDCl$_3$) δ 3.92 (3H, s), 5.66 (2H, s), 7.22–7.32 (4H, m), 7.39–7.44 (1H, m), 7.58 (1H, m), 7.90 (1H, s), 8.51–8.55 (2H, m), 9.21 (1H, s); MS (ES$^+$) m/e 420 [MH]$^+$; Anal. Found: C, 60.11; H, 3.52; N, 23.37%. C$_{21}$H$_{15}$F$_2$N$_7$O requires: C, 60.14; H, 3.61; N, 23.38%.

EXAMPLE 42

3-(3-Chlorophenyl)-7-(2-fluorophenyl)-2-(2-methyl-2H-[1,2,4]triazol-3-ylmethoxy)pyrazolo[1,5-d][1,2,4]triazine This was prepared using a similar procedure to that described in Example 18 except using 3-chloroboronic acid instead of 3-trifluoromethylbenzeneboronic acid. Data for title compound: MS (ES$^+$) m/e 436/438 [MH]$^+$.

EXAMPLE 43

3-(1,1-Dimethylpropyl)-2-(2-methyl-2H-[1,2,4] triazol-3-ylmethoxy)-7-(2,3,6-trifluorophenyl) pyrazolo[1,5-d][1,2,4]triazine a) 2,3,6-Trifluorobenzoic Hydrazide To 2,3,6-trifluorobenzoyl chloride, (29 g, 0.15 mol) in dichloromethane (200 ml) was added methanol (30 ml) dropwise at 5° C. The solution was allowed to warm to room temperature and was stirred under nitrogen for 2 h. The solvent was removed in uacuo and the residual oil was stirred with hydrazine monohydrate (19 ml, 0.40 mol) in ethanol (120 ml) at reflux for 3 h. The solvent was removed in vacuo, and the residue was partitioned between dichloromethane (400 ml) and water (200 ml). The biphasic mixture was filtered to remove insoluble material, then the aqueous layer was washed with dichloromethane (2×300 ml). The combined organic layers were dried over magnesium sulfate, and were concentrated in vacuo to yield 2,3,6-trifluorobenzoic hydrazide as a white solid (6.0 g). Data for the title compound: $^1$H NMR (400 MHz, CDCl$_3$) δ 4.18 (2H, br s), 6.93 (1H, m), 7.25 (2H, m); MS (ES$^+$) m/e 191 [MH]$^+$.

b) 3-(1,1-Dimethylpropyl)-2-(2-methyl-2H-[1,2,4]triazol-3-ylmethoxy)-7-(2,3,6-trifluorophenyl)pyrazolo[1,5-d][1,2,4]triazine This compound was prepared using the procedure described in Example 27, using 2,3,6-trifluorobenzoic hydrazide instead of 2,5-difluorobenzoic hydrazide. Data for the title compound: mp=122–125° C.; $^1$H NMR (360 MHz, CDCl$_3$) δ 0.78 (3H, t, J=7.5 Hz), 1.48 (6H, s), 1.79 (2H, q, J=7.5 Hz), 3.84 (3H, s), 5.46 (2H, s), 7.07 (1H, m), 7.43 (1H, m), 7.89 (1H, s), 9.42 (1H, s); MS (ES$^+$) m/e 432 [MH]$^+$.

EXAMPLE 44

3-(1,1-Dimethylpropyl)-2-(2-ethyl-2H-[1,2,4]triazol-3-ylmethoxy)-7-(2,3,6-trifluorophenyl)pyrazolo[5-d][1,2,4]triazine This compound was prepared using the procedure described in Example 27, using 2,3,6-trifluorobenzoic hydrazide (prepared as described in Example 43, step a)) instead of 2,5-difluorobenzoic hydrazide and using (2-ethyl-2H-[1,2,4]triazol-3-yl)methanol instead of (2-methyl-2H-[1,2,4]triazol-3-yl)methanol. Data for the title compound: mp=80–83° C.; $^1$H NMR (400 MHz. CDCl$_3$) δ 0.78 (3H, t, J=7.5 Hz), 1.42 (3H, t, J=7.3 Hz), 1.48 (6H, s), 1.79 (2H, q, J=7.5 Hz), 4.17 (2H, q, J=7.1 Hz), 5.50 (2H, s), 7.07 (1H, m), 7.44 (1H, m), 7.97 (1H, s), 9.44 (1H, s); MS (ES$^+$) m/e 446 [MH]$^+$.

EXAMPLE 45

3-(2-Fluorophenyl)-2-(2-methyl-2H-[1,2,4]triazol-3-ylmethoxy)-7-(pyridin-3-yl)pyrazolo[1,5-d][1,2,4]triazine This compound was prepared using the procedure described in Example 21, using nicotinic hydrazide instead of 2,5-difluorobenzoic hydrazide in step e). Data for the title compound: mp=164–166° C.; $^1$H NMR (400 MHz, CDCl$_3$) δ 3.99 (3H, s), 5.67 (2H, s), 7.27 (2H, m), 7.40 (1H, m), 7.59 (2H, m), 7.90 (1H, s), 8.75 (2H, mn), 9.25 (1H, s), 9.75 (1H, s); MS (ES$^+$) m/e 403 [MH]$^+$; Anal. Found: C, 59.90; H, 3.30; N, 27.40%. C$_{20}$H$_{15}$FN$_8$O requires: C, 59.70; H, 3.76; N, 27.85%.

EXAMPLE 46

2-(2-Ethyl-2H-[1,2,4]triazol-3-ylmethoxy)-7-(2-fluorophenyl)-3-(pyridin-4-yl)pyrazolo[1,5-d][1,2,4]triazine a) 3-Bromo-2-(2-ethyl-2H-[1,2,4]triazol-3-ylmethoxy)-7-(2-fluorophenyl)pyrazolo[1,5-d][1,2,4]triazine This was prepared in 76% yield using a similar procedure to that described in Example 17, step e), except using 3-chloromethyl-2-ethyl-2H-[1,2,4]triazole hydrochloride instead of 3-chloromethyl-2-methyl-2H-[1,2,4]triazole hydrochloride. Data for title compound: $^1$H NMR (360 MHz, CDCl$_3$) δ 1.46 (3H, t, J=7.2 Hz), 4.21 (2H, q, J=7.2 Hz), 5.53 (2H, s), 7.28 (1H, m), 7.39 (1H, t, J=7.6 Hz), 7.65 (1H, m), 7.79 (1H, m), 7.89 (1H, s), 9.23 (1H, s); MS (ES$^+$) m/e 418/420 [MH]$^+$.

b) 2-(2-Ethyl-2H-[1,2,4]triazol-3-ylmethoxy)-7-(2-fluorophenyl)-3-(pyridin-4-yl)pyrazolo[1,5-d][1,2,4]triazine This was prepared in 21% yield using a similar procedure to that described in Example 18 except using pyridine-4-boronic acid instead of 3-trifluoromethylbenzeneboronic acid and 3-bromo-2-(2-ethyl-2H-[1,2,4]triazol-3-ylmethoxy)-7-(2-fluorophenyl)pyrazolo[1,5-d][1,2,4]triazine instead of 3-bromo-7-(2-fluorophenyl)-2-(2-methyl-2H-[1,2,4]triazol-3-ylmethoxy)pyrazolo[1,5-d][1,2,4]triazine. Data for title compound: mp=214–217° C.; $^1$H NMR (360 MHz, CDCl$_3$) δ 1.35 (3H, t, J=7.2 Hz), 4.12 (2H, q, J=7.2 Hz), 5.60 (2H, s), 7.31 (1H, t, J=9.2 Hz), 7.42 (1H, t, J=7.6 Hz), 7.62 (2H, d, J=6.0 Hz), 7.68 (1H, m), 7.82 (1H, m), 7.90 (1H, s), 8.72 (2H, d, J=5.6 Hz), 9.53 (1H, s); MS (ES$^+$) m/e 417 [MH]$^+$.

EXAMPLE 47

2-(2-Ethyl-2H-[1,2,4]triazol-3-ylmethoxy)-3-(2-fluorophenyl)-7-(4-fluorophenyl)pyrazolo[1,5-d][1,2,4]triazine This compound was prepared using the procedure described in Example 21, steps b) to f), using 3-(2-fluorophenyl)-4-hydroxy-2-furanone (cf Example 2) instead of 3-tert-butyl-4-hydroxy-2-furanone, 4-fluorobenzoic hydrazide instead of 2,5-difluorobenzoic hydrazide in step e) and (2-ethyl-2H-[1,2,4]triazol-3-yl)methanol instead of (2-methyl-2H-[1,2,4]triazol-3-yl)methanol in step f). Data for the title compound: mp=179° C.; $^1$H NMR (400 MHz, CDCl$_3$) δ 1.38 (3H, t, J=7.4 Hz), 4.23 (2H, m), 5.67 (2H, s), 7.22–7.32 (4H, m), 7.39–7.44 (1H, m), 7.57 (1H, m), 7.92 (1H, s), 8.54–8.58 (2H, m), 9.21 (1H, s); MS (ES$^+$) m/e 434 [MH]$^+$; Anal. Found: C, 60.86; H, 3.83; N, 22.30%. C$_{22}$H$_{17}$F$_2$N$_7$O requires: C, 60.97; H, 3.95; N, 22.62%.

EXAMPLE 48

3-(2-Fluorophenyl)-7-(4-fluorophenyl)-2-(2-propyl-2H-[1,2,4]triazol-3-ylmethoxy)pyrazolo[1,5-d][1,2,4]triazine This compound was prepared using the procedure described in Example 47, using (2-propyl-2H-[1,2,4]triazol-3-yl)methanol instead of (2-ethyl2H-[1,2,4]triazol-3-yl) methanol. Data for the title compound: mp=148° C.; $^1$H NMR (400 MHz, CDCl$_3$) δ 0.79 (3H, t, J=7.4 Hz), 1.81 (2H, m), 4.11 (2H, m), 5.67 (2H, s), 7.22–7.32 (4H, m), 7.40–7.43 (1H, m), 7.57 (1H, m), 7.92 (1H, s), 8.54–8.58 (2H, m), 9.21 (1H, s); MS (ES$^+$) m/e 448 [MH]$^+$; Anal. Found: C, 61.74; H, 4.11; N, 21.75%. C$_{23}$H$_{19}$F$_2$N$_7$O requires: C, 61.74; H, 4.28; N, 21.91%.

EXAMPLE 49

7-(2,6-Difluorophenyl)-3-(2-fluorophenyl)-2-(2-methyl-2H-[1,2,4]triazol-3-ylmethoxy)pyrazolo[1,5-d][1,2,4]triazine This compound was prepared using the procedure described in Example 21, steps b) to f), using 3-(2-fluorophenyl)-4-hydroxy-2-furanone (cf Example 2) instead of 3-tert-butyl-4-hydroxy-2-furanone and 2,6-difluorobenzoic hydrazide instead of 2,5-difluorobenzoic hydrazide in step e). Data for the title compound: mp=163° C.; $^1$H NMR (360 MHz, CDCl$_3$) δ 3.78 (3H, s), 5.52 (2H, s), 7.16 (2H, m), 7.24–7.29 (2H, m), 7.38–7.44 (1H, m), 7.60–7.65 (2H, m), 7.85 (1H, s), 9.31 (1H, s); MS (ES$^+$) m/e 438 [MH]$^+$.

EXAMPLE 50

7-(2,6-Difluorophenyl)-2-(2-ethyl-2H-[1,2,4]triazol-3-ylmethoxy)-3-(2-fluorophenylpyrazolo[1,5-d][1,2,4]triazine This compound was prepared using the procedure described in Example 21, steps b) to f), using 3-(2-fluorophenyl)-4-hydroxy-2-furanone (cf. Example 2) instead of 3-tert-butyl-4-hydroxy-2-furanone, 2,6-difluorobenzoic hydrazide instead of 2,5-difluorobenzoic hydrazide in step e) and (2-ethyl-2H-[1,2,4]triazol-3-yl) methanol instead of (2-methyl-2H-[1,2,4]triazol-3-yl) methanol in step f). Data for the title compound: mp=196° C.; $^1$H NMR (400 MHz, CDCl$_3$) δ 1.33 (3H, t, J=7.5 Hz), 4.13 (2H, m), 5.53 (2H, s), 7.15 (2H, m), 7.22–7.27 (2H, m), 7.38–7.44 (1H, m), 7.58–7.66 (2H, m), 7.88 (1H, s), 9.31 (1H, s); MS (ES$^+$) m/e 452 [MH]$^+$.

EXAMPLE 51

3-(2-Fluorophenyl)-7-(3-fluorophenyl)-2-(2-methyl-2H-[1,2,4]triazol-3-ylmethoxy)pyrazolo[1,5-d][1,2,4]triazine This compound was prepared using the procedure described in Example 21, steps b) to f), using 3-(2-fluorophenyl)-4-hydroxy-2-furanone instead of 3-tert-butyl-4-hydroxy-2-furanone, and 3-fluorobenzoic hydrazide instead of 2,5-difluorobenzoic hydrazide in step e). Data for the title compound: mp=169–170° C.; $^1$H NMR (400 MHz, CDCl$_3$) δ 3.92 (3H, s), 5.67 (2H, s), 7.23–7.43 (4H, m), 7.57 (2H, m), 7.90 (1H, s), 8.25 (2H, m), 9.23 (1H, s); MS (ES$^+$) m/e 420 [MH]$^+$; Anal. Found: C, 60.16; H, 3.53; N, 23.52%. C$_{21}$H$_{15}$F$_2$N$_7$O requires: C, 60.14; H, 3.61; N, 23.38%.

EXAMPLE 52

7-(2,4-Difluorophenyl)-3-(2-fluorophenyl)-2-(2-methyl-2H-[1,2,4]triazol-3-ylmethoxy)pyrazolo[1,5-d][1,2,4]triazine This compound was prepared using the procedure described in Example 21, steps b) to f), using 3-(2-fluorophenyl)-4-hydroxy-2-furanone instead of 3-tert-butyl-4-hydroxy-2-furanone, and 2,4-difluorobenzoic hydrazide instead of 2,5-difluorobenzoic hydrazide in step e). Data for the title compound: mp=164–166° C.; $^1$H NMR (400 MHz, CDCl$_3$) δ 3.83 (3H, s), 5.56 (2H, s), 7.03–7.16 (2H, m), 7.26 (2H, m), 7.40 (1H, m), 7.61 (1H, m), 7.84 (2H, m), 9.27 (1H, s); MS (ES$^+$) m/e 420 [MH]$^+$; Anal. Found: C, 57.44; H, 3.29; N, 22.43%. C$_{21}$H$_{14}$F$_3$N$_7$O requires: C, 57.67; H, 3.23; N, 22.42%.

EXAMPLE 53

7-(2-Fluorophenyl)-2-(2-methyl-2H-[1,2,4]triazol-3-ylmethoxy)-3-(pyridin-2-yl)pyrazolo[1,5-d][1,2,4]triazine A mixture of 3-bromo-7-(2-fluorophenyl)-2-(2-methyl-2H-[1,2,4]triazol-3-ylmethoxy)pyrazolo[1,5-d][1,2,4]triazine (81.8 mg, 0.202 mmol) and 2-(tributylstannyl)pyridine (0.1520 g, 0.413 mmol) in anhydrous 1,4-dioxane (8 ml) was degassed using three freeze-pump-thaw cycles. Tetrakis(triphenylphosphine)palladium(0) (32.5 mg, 0.0281 mmol) and copper(I) iodide (4.5 mg, 0.024 mmol) were added and the mixture was further degassed with one freeze-pump-thaw cycle before heating at 100° C. under nitrogen for 18 h. The mixture was filtered through glass fibre paper, washing well with ethyl acetate (25 ml). The filtrate was washed with saturated aqueous NaCl (10 ml), and the aqueous layer was further extracted with ethyl acetate (25 ml). The combined organic extracts were dried (Na$_2$SO$_4$) and evaporated in vacuo. The residue was purified bar flash chromatography (silica gel, 4% MeOH/CH$_2$Cl$_2$ and silica gel, 0–4% MeOH/EtOAc) to give 62.4 mg (77%) of the title compound as a white solid, mp=186–187° C. (CH$_2$Cl$_2$-EtOAc); $^1$H NMR (400 MHz, CDCl$_3$) δ 3.79 (3H, s), 5.61 (2H, s), 7.20 (1H, m), 7.29 (1H, t, J=9.4 Hz), 7.40 (1H, td, J=7.6 and 0.8 Hz), 7.64 (1H, mn), 7.73 (1H, td, J=7.8 and 1.8 Hz), 7.80 (1H, m), 7.89 (1H, s), 7.94 (1H, d, J=8.0 Hz), 8.70 (1H, m), 10.30 (1H, s); MS (ES$^+$) m/e 403 [MH]$^+$. Anal. Found C, 59.76; H, 3.65; N, 27.65%. C$_{20}$H$_{15}$FN$_8$O requires C, 59.70; H, 3.76; N, 27.85%.

EXAMPLE 54

7-(2-Fluorophenyl)-2-(2-methyl-2H-[1,2,4]triazol-3-ylmethoxy)-3-(thien-2-yl)pyrazolo[1,5-d][1,2,4]triazine This was prepared in 30% yield using a similar procedure to that described in Example 53 except using 2-(tributylstannyl)thiophene instead of 2-(tributylstannyl)pyridine. Data for title compound: mp=196–197° C. (CH$_2$Cl$_2$-EtOAc); $^1$H NMR (360 MHz, CDCl$_3$) δ 3.84 (3H, s), 5.59 (2H, s), 7.16 (1H, dd, J=5.1 and 3.6 Hz), 7.29 (1H, t, J=9.5 Hz), 7.38–7.42 (2H, m), 7.48 (1H, dd, J=3.6 and 1.0 Hz), 7.65 (1H, m), 7.80 (1H, m), 7.88 (1H, s), 9.56 (1H, s); MS (ES$^+$) m/e 408 [MH]$^+$.

EXAMPLE 55

7-(2-Fluorophenyl)-3-(furan-2-yl)-2-(2-methyl-2H-[1,2,4]triazol-3-ylmethoxy)pyrazolo[1,5-d][1,2,4]triazine This was prepared in 20% yield using a similar procedure to that described in Example 53 except using 2-(tributylstannyl)furan instead of 2-(tributylstannyl)pyridine. Data for title compound: mp=188–190° C. (CH$_2$Cl$_2$-EtOAc); $^1$H NMR (400 MHz, CDCl$_3$) δ 3.82 (3H, s), 5.58 (2H, s), 6.52 (1H, m), 6.72 (1H, d, J=3.3 Hz), 7.28 (1H, m), 7.39 (1H, t, J=7.6 Hz), 7.56 (1H, s), 7.64 (1H, m), 7.79 (1H, mn), 7.88 (1H, s), 9.69 (1H, s); MS (ES$^+$) m/e 392 [MH]$^+$.

EXAMPLE 56

7-(2,4-Difluorophenyl)-3-(1,1-dimethylethyl)-2-(2-methyl-2H-[1,2,4]triazol-3-ylmethoxy)pyrazolo[1,5-d][1,2,4]triazine This compound was prepared using the procedure described in Example 21, using 2,4-difluorobenzoic hydrazide instead of 2,5-difluorobenzoic hydrazide in step e). Data for the title compound: mp=118° C.; $^1$H NMR (400 MHz, CDCl$_3$) δ 1.50 (9H, s), 3.84 (3H, s), 5.47 (2H, s), 7.02 (1H, m), 7.10 (1H, m), 7.76 (1H, m), 7.87 (1H, m), 9.40 (1H, s); MS (ES$^+$) m/e 400 [MH]$^+$; Anal. Found: C, 57.72; H, 4.70; N, 24.39%. C$_{19}$CH$_{19}$F$_2$N$_7$O.0.1 isohexane requires: C, 57.70; H, 5.04; N, 24.03%.

EXAMPLE 57

7-(2,4-Difluorophenyl)-3-(1,1-dimethylethyl)-2-(2-ethyl-2H-[1,2,4]triazol-3-ylmethoxy)pyrazolo[1,5-d][1,2,4]triazine This compound was prepared using the procedure described in Example 21, using 2,4-difluorobenzoic hydrazide instead of 2,5-difluorobenzoic hydrazide in step e) and (2-ethyl-2H-[1,2,4]triazol-3-yl)methanol instead of (2-methyl-2H-[1,2,4]triazol-3-yl)methanol in step f). Data for the title compound: mp=145° C.; $^1$H NMR (400 MHz, CDCl$_3$) δ 1.42 (3H, t), 1.49 (9H, s), 4.17 (2H, m), 5.48 (2H, s), 7.02 (1H, m), 7.11 (1H, m), 7.78 (1H, m), 7.90 (1H, m), 9.40 (1H, s); MS (ES$^+$) m/e 414 [MH]$^+$; Anal. Found: C, 57.67; H, 5.09; N, 23.14%. C$^{19}$H$_{21}$F$_2$N$_7$O.0.25H$_2$O requires: C, 57.48; H, 5.19; N, 23.46%.

EXAMPLE 58

2-(2-Ethyl-2H-[1,2,4]triazol-3-ylmethoxy)-3,7-bis(2-fluorophenyl)-pyrazolo[1,5-d][1,2,4]triazine a) 4-(2-Fluorophenyl)-5-(hydroxymethyl)pyrazol-3-one This compound was prepared in the same way as described for Example 1, step a) except 4-hydroxy-3-(2-fluorophenyl)-2-furanone (prepared using the conditions of Thuring, *J. Chem. Soc., Perkin Trans.* 1, 1997, 767–774, starting from 2-fluorophenylacetic acid) was used instead of 4-hydroxy-3-phenyl-2-furanone. Data for title compound: $^1$H NMR (360 MHz, CDCl$_3$) δ 4.34 (2H, s), 7.18 (2H, m), 7.23–7.30 (1H, m), 7.41 (1H, m); MS (ES$^+$) m/e 409 [MH]$^+$.

b) 4-(2-Fluorophenyl)-5-hydroxymethyl-3-(p-toluenesulfonyloxy)pyrazole

To a suspension of 4-(2-fluorophenyl)-5-(hydroxymethyl) pyrazol-3-one (28.7 g, 0.138 mol) in dry dichloromethane (300 ml) was added p-toluenesulfonyl chloride (28.9 g, 0.152 mol) followed by triethylamine (21.2 ml, 0.152 mol) dropwise. The solution was stirred at room temperature for 2 days. Dichloromethane (300 ml) was then added to dilute and the solution was washed with brine (300 ml), dried (Na$_2$SO$_4$), filtered and concentrated in vacuo. The residue was purified by silica gel chromatography with 0%→40% ethyl acetate/dichloromethane as eluent to give the title compound (23.7 g). Data for the title compound: $^1$H NMR (360 MHz, DMSO) δ 2.34 (3H, s), 4.66 (2H, s), 6.94 (1H, t), 7.06 (3H, m), 7.17–7.25 (2H, m), 7.51 (2H, d); MS (ES$^+$) m/e 362 [MH]$^+$.

c) 4-(2-Fluorophenyl)-5-formyl-3-(p-toluenesulfonyloxy) pyrazole

The product from step b) (13.7 g, 0.038 mol) was dissolved in chloroform (500 ml) and manganese dioxide (13.1 g, 0.151 mol) was added. The reaction mixture was heated at 70° C. for 24 h then cooled and filtered through a very large plug of silica and sand. After washing the silica with 10% methanol in dichloromethane (4 l), the filtrate was concentrated in uacuo to leave a solid (13.4 g). Data for the title compound: $^1$H NMR (360 MHz, CDCl$_3$) δ 2.34–2.40 (3H, m), 6.98–7.63 (8H, m), 9.64 (1H, s); MS (ES$^+$) m/e 360 [MH]$^+$. The NMR peaks were broad suggesting the existence of 2 tautomers.

d) 4-(2-Fluorophenyl)-5-(2-fluorophenyl)carbonylaminoimino-3-(p-toluenesulfonyloxy)pyrazole The product from step c) (10 g, 0.028 mol) was suspended in xylene (250 ml) with 2-fluorobenzoic hydrazide (4.7 g, 0.0231 mol) and heated under reflux for 3 h. After cooling, the reaction mixture was filtered and the solid produced was washed in the sinter funnel several times with dichloromethane then concentrated under vacuum to leave a solid (10.53 g). The product existed as a 1:1 mixture of 2 tautomers. $^1$H NMR (400 MHz, CDCl$_3$) δ 2.37 (3H, s), 7.18–7.66 (12H, m), 8.06 (1H, s), 11.90 (0.5H, s), 13.78 (0.5H, s); MS (ES$^+$) m/e 497 [MH]$^+$.

e) 3,7-bis(2-Fluorophenyl)-2-(P-toluenesulfonyloxy) pyrazolo[1,5-d][1,2,4]triazine and 3,7-bis(2-Fluorophenyl)pyrazolo[1,5-d][1,2,4]triazin-2-ol The product from step d) (10.53 g, 0.021 mol) was suspended in Dowtherm A (500 ml) and heated at 180° C. for 22 h. After cooling, the solution was purified by silica gel chromatography eluting with dichloromethane to remove all Dowtherm A, then with 0%→20% ethyl acetate/ dichloromethane to give the title compounds (7.49 g and 1.55 g). Data for 3,7-bis(2-fluorophenyl)-2-(p-toluenesulfonyloxy)pyrazolo[1,5-d][1,2,4]triazine: $^1$H NMR (400 MHz, CDCl$_3$) δ 2.41 (3H, s), 7.14 (2H, d), 7.20–7.31 (3H, m), 7.35–7.47 (2H, m), 7.59 (1H, m), 7.64–7.70 (1H, m), 7.72 (2H, m), 7.75–7.80 (1H, m), 9.30 (1H, s); MS (ES$^+$) m/e 478 [MH]$^+$. Data for 3,7-bis(2-fluorophenyl)pyrazolo[1,5-d][1,2,4]triazin-2-ol: $^1$H NMR (400 MHz, CDCl$_3$) δ 7.32–7.42 (2H, m), 7.45–7.51 (3H, m), 7.69–7.74 (2H, m), 7.85 (1H, m), 9.35 (1H, s), 12.39 (1H, s); MS (ES$^+$) m/e 325 [MH]$^+$.

f) 2-(2-Ethyl-2H-[1,2,4]triazol-3-ylmethoxy)-3,7-bis(2-fluorophenyl)-pyrazolo[1,5-d][1,2,4]triazine The title compound was prepared as part of a rapid analogue library using the following methodology. To a solution of (2-ethyl-2H-[1,2,4]triazol-3-yl)methanol (32 mg, 0.25 mmol) in dry N,N-dimethylformamide (5 ml) in a RADLEYS reaction carousel under nitrogen was added sodium hydride (60% wt in oil) (10 mg, 0.25 mmol) and the suspension was stirred for 30 min. A solution of 3,7-bis(2-fluorophenyl)-2-(p-toluenesulfonyloxy)pyrazolo[1,5-d][1,2,4]triazine (100 mg, 0.21 mmol) in dry N,N-dimethylformamide (2 ml) was then added and the solution was stirred under nitrogen for 1 h. A further amount (4 mg, 0.10 mmol) of sodium hydride (60% wt in oil) was added and the solution was stirred for 18 h. Water (25 ml) was added to quench the reaction and the solid which was precipitated was collected by filtration and washed with water. The solid was dissolved in dichloromethane, filtered and the filtrate was concentrated in vacuo to give a white solid (40 mg). Data for the title compound: mp=164° C.; $^1$H NMR (360 MHz, CDCl$_3$) δ 1.31 (3H, t), 4.09–4.16 (2H, m), 5.56 (2H, s), 7.21–7.33, (3H, m), 7.37–7.43 (2H, m), 7.58–7.68 (2H, m), 7.82 (1H, m), 7.87 (1H, s), 9.28 (1H, s); MS (ES$^+$) m/e 434 [MH]$^+$; HPLC>97% purity (run on an HP1100, using a Hichrom KR100-5C18, 25 cm column, flow rate of 1 ml/min and 50% acetonitrile/pH 3 phosphate buffer as the mobile phase).

EXAMPLE 59

3,7-bis(2-Fluorophenyl)-2-(1-methyl-1H-[1,2,4]triazol-3-ylmethoxy)pyrazolo[1,5-d][1,2,4]triazine The title compound was prepared as part of a rapid analogue library using the procedure described in Example 58, step f) using (1-methyl-1H-[1,2,4]triazol-3-yl)methanol (prepared as described in WO 98/04559) instead of (2-ethyl- 2H-[1,2,4]triazol-3-yl)methanol. Data for the title compound: mp=184° C.; $^1$H NMR (400 MHz, CDCl$_3$) δ 3.91 (3H, s), 5.49 (2H, s), 7.22–7.39 (5H, m), 7.62 (1H, m);, 7.74 (1H, m), 7.85 (1H, m), 8.01 (1H, s), 9.27 (1H, s); MS (ES$^+$) m/e 420 [MH]$^+$; HPLC>98% purity (run on an HP1100, using a Hichrom KR100-5C18, 25 cm column, flow rate of 1 ml/min and 50% acetonitrile/pH 3 phosphate buffer as the mobile phase).

EXAMPLE 60

3,7-bis(2-Fluorophenyl)-2-(3-methyl-3H-[1,2,3]triazol-4-ylmethoxy)pyrazolo[1,5-d][1,2,4]triazine The title compound was prepared as part of a rapid analogue library using the procedure described in Example 58, step f) using (1-methyl-1H-[1,2,3]triazol-5-yl)methanol (prepared as described in WO 98/04559) instead of (2-ethyl-2H-[1,2,4]triazol-3-yl)methanol. Data for the title compound: mp=188° C.; $^1$H NMR (360 MHz, CDCl$_3$) δ 4.00 (3H, s), 5.49 (2H, s), 7.23–7.29 (2H, m), 7.34 (1H, m), 7.39–7.45 (2H, m), 7.54 (1H, m), 7.65–7.71 (2H, m), 7.81 (1H, m), 9.27 (1H, s); MS (ES$^+$) m/e 420 [MH]$^+$; HPLC>98% purity (run on an HP1100, using a Hichrom KR100-5C18, 25 cm column, flow rate of 1 m/min and 50% acetonitrile/pH 3 phosphate buffer as the mobile phase).

EXAMPLE 61

3,7-bis(2-Fluorophenyl)-2-(1-methyl-1H-[1,2,3]triazol-4-ylmethoxy)pyrazolo[1,5-d][1,2,4]triazine The title compound was prepared as part of a rapid analogue library using the procedure described in Example 58, step f) using (1-methyl-1H-[1,2,3]triazol-4-yl)methanol (prepared as described in Khim. Geterotsikl. Soedin., 1980, 12, 1688–9) instead of (2-ethyl-2H-[1,2,4]triazol-3-yl)methanol. Data for the title compound: mp=175° C.; $^1$H NMR (360 MHz, CDCl$_3$) δ 4.06 (3H, s), 5.54 (2H, s), 7.20–7.26 (2H, m), 7.29–7.44 (3H, m), 7.52 (1H, s), 7.62–7.69 (2H, m), 7.84 (1H, dt), 9.27 (1H, s); MS (ES$^+$) m/e 420 [MH]$^+$; HPLC>96% purity (run on an HP1100, using a Hichrom KR100-5C18, 25 cm column, flow rate of 1 ml/min and 50% acetonitrile/pH 3 phosphate buffer as the mobile phase).

EXAMPLE 62

3,7-bis(2-Fluorophenyl)-2-(6-methylpyridin-2-ylmethoxy)pyrazolo[1,5-d][1,2,4]triazine The title compound was prepared as part of a rapid analogue library using the procedure described in Example 58, step f) using 6-methyl-2-pyridinemethanol instead of (2-ethyl-2H-[1,2,4]triazol-3-yl)methanol. Data for the title compound: mp=197° C.; $^1$H NMR (360 MHz, CDCl$_3$) δ 2.54 (3H, s), 5.51 (2H, s), 7.08 (1H, d), 7.23–7.34 (4H, m), 7.35–7.43 (2H, m), 7.55–7.66 (2H, m), 7.73–7.82 (2H, m), 9.28 (1H, s); MS (ES$^+$) m/e 430 [MH]$^+$; HPLC>98% purity (run on an HP1100, using a Hichrom KR100-5C18, 25 cm column, flow rate of 1 ml/min and 50% acetonitrile/pH 3 phosphate buffer as the mobile phase).

EXAMPLE 63

3,7-bis(2-Fluorophenyl)-2-(pyridin-3-ylmethoxy)pyrazolo[1,5-d][1,2,4]triazine

The title compound was prepared as part of a rapid analogue library using the procedure described in Example 58, step f) using 3-pyridinemethanol instead of (2-ethyl-2H-[1,2,4]triazol-3-yl)methanol. Data for the title compound: mp=146° C.; $^1$H NMR (360 MHz, CDCl$_3$) δ 5.44 (2H, s), 7.23–7.29 (3H, m), 7.33 (1H, m), 7.37–7.43 (2H, m), 7.61–7.69 (2H, m), 7.74 (1H, m), 7.81 (1H, m), 8.57 (1H, m), 8.66 (1H, s), 9.26 (1H, s); MS (ES$^+$) m/e 416 [MH]$^+$; HPLC>98% purity (run on an HP1100, using a Hichrom KR100-5C18, 25 cm column, flow rate of 1 ml/min and 40% acetonitrile/pH 3 phosphate buffer as the mobile phase).

EXAMPLE 64

3,7-bis(2-Fluorophenyl)-2-(pyridin-4-ylmethoxy)pyrazolo[1,5-d][1,2,4]triazine

The title compound was prepared as part of a rapid analogue library using the procedure described in Example 58, step f) using 4-pyridinemethanol instead of (2-ethyl-2H-[1,2,4]triazol-3-yl)methanol. Data for the title compound: mp=143° C.; $^1$H NMR (400 MHz, CDCl$_3$) δ 5.43 (2H, s), 7.27–7.33 (5H, m), 7.35–7.47 (2H, m), 7.61–7.71 (2H, m), 7.79 (1H, m), 8.58 (2H, m), 9.28 (1H, s); MS (ES$^+$) m/e 416 [MH]$^+$; HPLC>98% purity (run on an HP1100, using a Hichrom KR100-5C18, 25 cm column, flow rate of 1 ml/min and 45% acetonitrile/pH 3 phosphate buffer as the mobile phase).

EXAMPLE 65

2-(3-Cyclobutyloxypyridin-2-ylmethoxy)-3,7-bis(2-fluorophenyl)-pyrazolo[1,5-d][1,2,4]triazine a) 3-Cyclobutyloxy-2-pyridinemethanol 3-Hydroxy-2-(hydroxymethyl)pyridine hydrochloride (1.57 g, 0.009 mol), potassium carbonate (8.09 g, 0.058 mol) and cyclobutyl bromide (5.0 g, 0.037 mol) were stirred together under nitrogen in N,N-dimethylformamide (20 ml) at 50° C. overnight. Water (40 ml) was added, and the resultant solution was acidified to pH 1 with hydrochloric acid (5 N). The solution was washed with dichloromethane (3×100 ml), basified to pH 14 with sodium hydroxide solution (4 N), and extracted with dichloromethane (3×100 ml). The organic layers from the extraction were combined, washed with water (1×100 ml), dried over magnesium sulfate and concentrated in uacuo to give a dark brown solid which was recrystallised from hexane to give the title compound (0.44 g). $^1$H NMR (250 MHz, CDCl$_3$) δ 1.61–1.81 (1H, m), 1.86–1.91 (1H, m), 2.09–2.22 (2H, m), 2.39–2.51 (2H, m), 4.31 (1H, br s), 4.66 (1H, m), 4.74 (1H, s), 6.97 (1H, m), 7.07–7.17 (1H, m), 8.13 (1H, m); MS (ES$^+$) m/e 180 [MH]$^+$.

b) 2-(3-Cyclobutyloxypyridin-2-ylmethoxy)-3,7-bis(2-fluorophenyl)-pyrazolo[1,5-d][1,2,4]triazine The title compound was prepared as part of a rapid analogue library using the procedure described in Example 58, step f) using the product from above in step a) instead of (2-ethyl-2H-[1,2,4]triazol-3-yl)methanol. Data for the title compound: mp=66° C.; $^1$H NMR (400 MHz, CDCl$_3$) δ 1.60–1.70 (1H, m), 1.74–1.82 (1H, m), 1.95–2.08 (2H, m), 2.31–2.39 (2H, m), 4.55–4.62 (1H, m), 5.60 (2H, s), 7.02 (1H, d), 7.16–7.28 (4H, m), 7.31–7.37 (2H, m), 7.58–7.64 (1H, m), 7.76–7.84 (2H, m), 8.15 (2H, m), 9.26 (1H, s); MS (ES$^+$) m/e 486 [MH]$^+$; HPLC>89% purity (run on an HP1100, using a Hichrom KR100-5C18, 25 cm column, flow rate of 1 ml/min and 65% acetonitrile/pH 3 phosphate buffer as the mobile phase).

EXAMPLE 66

2-[3,7-bis(2-Fluorophenyl)pyrazolo[1,5-d][1,2,4]
triazin-2-yloxymethyl]-pyridin-3-yloxyacetonitrile a) (2-Hydroxymethylpyridin-3-yloxy)acetonitrile Potassium carbonate (8.57 g, 0.062 mol) was stirred in DMSO (30 ml) under nitrogen at room temperature for 20 min. The mixture was cooled to 0° C. and 3-hydroxy-2-(hydroxymethyl)pyridine hydrochloride (5.0 g, 0.031 mol) was added. The slurry was stirred at 0° C. for 1.5 h before the addition of chloroacetonitrile (1.96 ml, 2.34 g, 0.031 mol). The mixture was allowed to warm to room temperature and stirred under nitrogen for 72 h. Water (100 ml) was added, and the resultant solution was extracted with dichloromethane (3×100 ml), the organic layers were combined, washed with water (1×100 ml) and saturated sodium chloride solution (1×100 ml), dried over magnesium sulfate and concentrated in vacuo to give the title compound as a dark brown solid (3.04 g). $^1$H NMR (250 MHz, CDCl$_3$) δ 4.77 (2H, s), 4.85 (2H, s), 7.26–7.30 (2H, m), 8.32 (1H, m); MS (ES$^+$) m/e, 165 [MH]$^+$.

b) 2-[3,7-bis(2-Fluorophenyl)pyrazolo[1,5-d][1,2,4]triazin-2-yloxymethyl]-pyridin-3-yloxyacetonitrile The title compound was prepared as part of a rapid analogue library using the procedure described in Example 58, step f) using the product from above in step a) instead of (2-ethyl-2H-[1,2,4]triazol-3-yl)methanol. Data for the title compound: $^1$H NMR (400 MHz, CDCl$_3$) δ 4.67 (2H, s), 5.59 (2H, s), 7.20–7.29 (3H, m), 7.31–7.39 (4H, m), 7.59–7.65 (1H, m), 7.73 (1H, m), 7.81 (1H, m), 8.33–8.35 (1H, m), 9.26 (1H, s); MS (ES$^+$) m/e 471 [MH]$^+$; HPLC>90% purity (run on an HP1100, using a Hichrom KR100-5C18, 25 cm column, flow rate of 1 ml/min and 55% acetonitrile/pH 3 phosphate buffer as the mobile phase).

EXAMPLE 67

3,7-bis(2-Fluorophenyl)-2-(3-methoxypyridin-2-ylmethoxy)pyrazolo[1,5-d][1,2,4]triazine The title compound was prepared as part of a rapid analogue library using the procedure described in Example 58, step i) using 3-methoxy-2-pyridinemethanol (prepared as described in WO 98/50385) instead of (2-ethyl-2H-[1,2,4]triazol-3-yl)methanol. Data for the title compound: mp=143° C.; $^1$H NMR (400 MHz, CDCl$_3$) δ 3,78 (3H, s), 5.58 (2H, s), 7.18–7.27 (5H, m), 7.31–7.37 (2H, m), 7.58–7.62 (1H, m), 7.75–7.83 (2H, m), 8.17–8.19 (1H, m), 9.26 (1H, s); MS (ES$^+$) m/e 446 [MH]$^+$: HPLC>99% purity (run on an HP1100, using a Hichrom KR100-5C18, 25 cm column, flow rate of 1 ml/min and 65% acetonitrile/pH 3 phosphate buffer as the mobile phase).

EXAMPLE 68

2-(3-Ethoxypyridin-2-ylmethoxy)-3,7-bis(2-fluorophenyl)pyrazolo[1,5-d][1,2,4]triazine The title compound was prepared as part of a rapid analogue library using the procedure described in Example 58, step f) using 3-ethoxy-2-pyridinemethanol (prepared as described in WO 98/04559) instead of (2-ethyl-2H-[1,2,4]triazol-3-yl)methanol. Data for the title compound: mp=77° C.; $^1$H NMR (400 MHz, CDCl$_3$) δ 1.28 (3H, m), 4.00 (2H, m), 5.61 (2H, s), 7.16–7.27 (5H, m), 7.31–7.37 (2H, m), 7.58–7.63 (1H, m), 7.75–7.83 (2H, m), 8.16 (1H, m), 9.26 (1H, s); MS (ES$^+$) m/e 460 [MH]$^+$; HPLC>95% purity (run on an HP1100, using a Hichrom KR100-5C18, 25 cm column, flow rate of 1 ml/min and 65% acetonitrile/pH 3 phosphate buffer as the mobile phase).

EXAMPLE 69

3,7-bis(2-Fluorophenyl)-2-(3-methylpyridin-2-ylmethoxy)pyrazolo[1,5-d][1,2,4]triazine The title compound was prepared as part of a rapid analogue library using the procedure described in Example 58, step f) using 3-methyl-2-pyridinemethanol (prepared as described in J. Med. Chem., 1998, 41(11), 1827–1837) instead of (2-ethyl-2H-[1,2,4]triazol-3-yl)methanol. Data for the title compound: mp=69° C.; $^1$H NMR (400 MHz, CDCl$_3$) δ 2.31 (3H, s), 5.55 (2H, s), 7.16–7.29 (3H, m), 7.33–7.39 (3H, m), 7.48 (1H, m), 7.60–7.65 (1H, m), 7.67–7.72 (1H, m), 7.80 (1H, m), 8.42 (1H, m), 9.25 (1H, s); MS (ES$^+$) m/e 430 [MH]$^+$; HPLC>97% purity (run on an HP1100, using a Hichrom KR100-5C18, 25 cm column, flow rate of 1 ml/min and 65% acetonitrile/pH 3 phosphate buffer as the mobile phase).

EXAMPLE 70

N-[3-[3,7-bis(2-Fluorophenyl)pyrazolo[1,5-d][1,2,4]
triazin-2-yloxymethyl]benzyl]-N,N-dimethylamine The title compound was prepared as part of a rapid analogue library using the procedure described in Example 58, step f) using 3-(N,N-dimethylaminomethyl)benzenemethanol (prepared as described in JP-A-55053247) instead of (2-ethyl-2H-[1,2,4]triazol-3-yl)methanol. Data for the title compound as a liquid: $^1$H NMR (400 MHz, CDCl$_3$) δ 2.23 (6H, s), 3.41 (2H, s), 5.41 (2H, s), 7.22–7.41 (9H, m), 7.63–7.71 (2H, m), 7.82 (1H, m), 9.26 (1H, s); MS (ES$^+$) m/e 472 [MH]$^+$; HPLC>93% purity (run on an HP1100, using a Hichrom KR100-5C18, 25 cm column, flow rate of 1 ml/min and 35% acetonitrile/pH 3 phosphate buffer as the mobile phase).

EXAMPLE 71

3,7-bis(2-Fluorophenyl)-2-(4-methylthiazol-2-ylmethoxy)pyrazolo[1,5-d][1,2,4]triazine The title compound was prepared as part of a rapid analogue library using the procedure described in Example 58, step f) using 4-methyl-2-thiazolemethanol (prepared as described in Acta Chem. Scand., 1966, 20(10), 2649–57) instead of (2-ethyl-2H-[1,2,4]triazol-3-yl)methanol. Data for the title compound: mp=176° C.; $^1$H NMR (400 MHz, CDCl$_3$) δ 2.45 (3H, s), 5.63 (2H, s), 7.23–7.32 (3H, m), 7.36–7.42 (3H, m), 7.62–7.65 (1H, m), 7.71 (1H, m), 7.83 (1H, m), 9.29 (1H, s); MS (ES$^+$) m/e 436 [MH]$^+$; HPLC>98% purity (run on an HP1100, using a Hichrom KR100-5C18, 25 cm column, flow rate of 1 ml/min and 60% acetonitrile/pH 3 phosphate buffer as the mobile phase).

EXAMPLE 72

3,7-bis(2-Fluorophenyl)-2-(5-methylthiazol-2-ylmethoxy)pyrazolo[1,5-d][1,2,4]triazine The title compound was prepared as part of a rapid analogue library using the procedure described in Example 58, step f) using 5-methyl-2-thiazolemethanol prepared as described in WO 98/04559) instead of (2-ethyl-2H-[1,2,4]triazol-3-yl)methanol. Data for the title compound: mp=154° C.; $^1$H NMR (400 MHz, CDCl$_3$) δ 2.44 (3H, s), 5.67 (2H, s), 6.89 (1H, s), 7.23–7.31 (3H, m), 7.35–7.41 (2H, m), 7.61–7.65 (1H, m), 7.73 (1H, m), 7.83 (1H, m), 9.30 (1H, s); MS (ES$^+$) m/e 436 [MH]$^+$; HPLC>98% purity (run on an HP1100, using a Hichrom KR100-5C18, 25 cm column, flow rate of 1 ml/min and 60% acetonitrile/pH 3 phosphate buffer as the mobile phase).

EXAMPLE 73

3,7-bis(2-Fluorophenyl)-2-(thiazol-4-ylmethoxy) pyrazolo[1,5-d][1,2,4]triazine

The title compound was prepared as part of a rapid analogue library using the procedure described in Example 58, step f) using 4-thiazolemethanol (prepared as described in WO 98/04559) instead of (2-ethyl-2H-[1,2,4]triazol-3-yl) methanol. Data for the title compound: mp=212° C.; $^1$H NMR (400 MHz, CDCl$_3$) δ 5.61 (2H, s), 7.23–7.33 (3H, m), 7.36–7.41 (3H, m), 7.62–7.67 (1H, m), 7.71 (1H, m), 7.83 (1H, m), 8.80 (1H, s), 9.28 (1H, s); MS (ES$^+$) m/e 422 [MH]$^+$; HPLC>97% purity (run on an HP1100, using a Hichrom KR100-5C18, 25 cm column, flow rate of 1 ml/min and 55% acetonitrile/pH 3 phosphate buffer as the mobile phase).

EXAMPLE 74

3,7-bis(2-Fluorophenyl)-2-(2-isopropyl-2H-[1,2,4] triazol-3-ylmethoxy)-pyrazolo[1,5-d][1,2,4]triazine The title compound was prepared as part of a rapid analogue library using the procedure described in Example 58, step f) using (2-isopropyl-2H-[1,2,4]triazol-3-yl) methanol (prepared as described in Chem.-Ztg., 1986, 110 (7–8), 275–81) instead of (2-ethyl-2H-[1,2,4]triazol-3-yl) methanol. Data for the title compound: mp=179° C.; $^1$H NMR (400 MHz, CDCl$_3$) δ 1.36 (3H, s), 1.38 (3H, s), 4.64–4.67 (1H, m), 5.58 (2H, s), 7.21–7.26 (2H, m), 7.30 (1H, m), 7.38–7.42 (2H, m), 7.58 (1H, m), 7.62–7.68 (1H, m), 7.85 (1H, m), 7.89 (1H, s), 9.28 (1H, s); MS (ES$^+$) m/e 448 [MH]$^+$; HPLC>97% purity (run on an HP100, using a Hichrom KR$^{100}$-5C18, 25 cm column, flow rate of 1 ml/min and 55% acetonitrile/pH 3 phosphate buffer as the mobile phase).

EXAMPLE 75

6-[3,7-bis(2-Fluorophenyl)pyrazolo[1,5-d][1,2,4] triazin-2-yloxymethyl-nicotinonitrile To a solution of 6-(chloromethyl)nicotinonitrile (56 mg, 0.37 mmol), (prepared as described in Chem. Lett., 1984, 5, 769–72) and 3,7-bis(2-fluorophenyl)pyrazolo[1,5-d][1,2,4]triazin-2-ol (100 mg, 0.31 mmol) (prepared as described in Example 58, step e)) in dry N,N-dimethylformamide (8 ml) under nitrogen was added potassium carbonate (ground to a fine powder) (256 mg, 1.85 mmol) and the suspension was stirred for 18 h. Water (20 ml) was added to quench the reaction, a solid was precipitated and this was collected by filtration and washed with water. The solid was dissolved in dichloromethane, filtered and the filtrate was concentrated in uacuo to give a white solid. Recrystallisation from ethyl acetate/isohexane gave the required product (40 mg, mp=186° C.). Data for the title compound: $^1$H NMR (400 MHz, CDCl$_3$) δ 5.60 (2H, s), 7.21–7.39 (4H, m), 7.42–7.48 (1H, m), 7.57 (1H, m), 7.61–7.66 (1H, m), 7.70 (1H, m), 7.79 (1H, m), 7.95 (1H, m), 8.85 (1H, s), 9.29 (1H, s); MS (ES$^+$) m/e 441 [MH]$^+$; Anal. Found: C, 64.30; H, 3.09; N, 18.59%. C$_{24}$H$_{14}$F$_2$N$_6$O.0.0.1C$_3$H$_7$NO.0.25H$_2$O requires: C, 64.54; H, 3.39; N, 18.89%.

EXAMPLE 76

3,7-bis(2-Fluorophenyl)-2-(pyridazin-3-ylmethoxy) pyrazolo[1,5-d][1,2,4]triazine a) 3-(Chloromethyl)pyridazine To a solution of 3-methylpyridazine (0.97 ml, 1 g, 0.0106 mol) at reflux in chloroform (50 ml) under nitrogen was added (with care) trichloroisocyanuric acid (1.037 g, 0.0045 mol) over 5 min and the suspension was stirred under reflux for, 18 h. Once cooled, the solution was filtered and washed with 1 N sodium hydroxide solution (25 ml), brine (25 ml) then dried (MgSO$_4$) and concentrated in uacuo. The brown oil obtained was kept under nitrogen in the freezer as it decomposes very quickly at room temperature. Data for, the title compound: $^1$H NMR (400 MHz, CDCl$_3$) δ 4.91 (2H, s), 7.52–7.56 (1H, m), 7.71–7.74 (1H, m), 9.16 (1H, s); MS (ES$^+$) m/e 129 [MH]$^+$.

b) 3,7-bis(2-Fluorophenyl)-2-(pyridazin-3-ylmethoxy) pyrazolo[1,5-d][1,2,4]triazine The title compound was prepared using the procedure described in Example 75, using 3-(chloromethyl)pyridazine instead of 6-(chloromethyl)nicotinonitrile. Data for the title compound: mp=210° C.; $^1$H NMR (400 MHz, CDCl$_3$) δ 5.79 (2H, s), 7.23–7.32 (3H, m), 7.35–7.50 (3H, m), 7.61–7.73 (3H, m), 7.81 (1H, m), 9.16 (1H, s), 9.29 (1H, s); MS (ES$^+$) m/e 417 [MH]$^+$; HPLC>99% purity (run on an HP1100. using a Hichrom KR100-5C18, 15 cm column, flow rate of 1 ml/min and 40% acetonitrile/pH 3 phosphate buffer as the mobile phase).

EXAMPLE 77

3,7-bis(2-Fluorophenyl)-2-(pyrazin-2-ylmethoxy) pyrazolor[1,5-d][1,2,4]triazine

The title compound was prepared using the procedure described in Example 76, using 2-methylpyrazine instead of 3-methylpyridazine in step a). Data for the title compound: mp=189° C.; $^1$H NMR (400 MHz, CDCl$_3$) δ 5.58 (2H, s), 7.25–7.32 (3H, m), 7.36–7.45 (2H, m), 7.62–7.68 (1H, m), 7.73 (1H, m), 7.80 (1H, m), 8.55 (2H, m), 8.73 (1H, s), 9.29 (1H, s); MS (ES$^+$) m/e 417 [MH]$^+$; Anal. Found: C, 62.89; H, 3.24; N, 19.92%. C$_{22}$H$_{14}$F$_2$N$_6$O.0.0.25 H$_2$O requires: C, 62.78; H, 3.47; N, 19.97%.

EXAMPLE 78

3,7-bis(2-Fluorophenyl)-2-(pyrimidin-4-ylmethoxy) pyrazolo[1,5-d][1,2,4]triazine The title compound was prepared using the procedure described in Example 76, using 4-methylpyrimidine instead of 3-methylpyridazine in step a). Data for the title compound: mp 189° C.; $^1$H NMR (400 MHz, CDCl$_3$) δ 5.52 (2H, s), 7.21–7.38 (4H, m), 7.43–7.48 (2H, m), 7.60–7.66 (1H, m), 7.72 (1H, m), 7.78 (1H, m), 8.73 (1H, m), 9.17 (1H, s), 9.30 (1H, s); MS (ES$^+$) m/e 417 [MH]$^+$; HPLC>99% purity (run on an HP1100, using a Hichrom KR100-5C18, 15 cm column, flow rate of 1 ml/min and 40% acetonitrile/pH 3 phosphate buffer as the mobile phase).

EXAMPLE 79

3,7-bis(2-Fluorophenyl)-2-(quinoxalin-2-ylmethoxy) pyrazolo[1,5-d][1,2,4]triazine The title compound was prepared using the procedure described in Example 76, using 2-methylquinoxaline instead of 3-methylpyridazine in step a). Data for the title compound: mp=209° C.; $^1$H NMR (400 MHz, CDCl$_3$) δ 5.76 (2H, s), 7.16 (1H, m), 7.26–7.36 (3H, m), 7.39–7.45 (1H, m), 7.58–7.64 (1H, m), 7.73–7.84 (4H, m), 8.05–8.09 (1H, m), 8.12–8.17 (1H, m), 9.02 (1H, s), 9.29 (1H, s); MS (ES$^+$) m/e 467 [MH]$^+$; Anal. Found: C, 66.52; H, 3.32; N, 17.80%. C$_b$ $_{26}$H$_{16}$F$_2$N$_6$O.0.0.25 H$_2$O requires: C, 66.31; H, 3.53; N, 17.84%.

EXAMPLE 80

3-(2-Fluorophenyl)-7-(furan-3-yl)-2-(2-methyl-2H-[1,2,4]triazol-3-ylmethoxy)pyrazolo[1,5-d][1,2,4]triazine This compound was prepared using; the procedure described in Example 21, steps e) and f), using 4-(2-fluorophenyl)-5-formyl-3-(p-toluenesulfonyloxy)pyrazole (prepared as described in Example 58, steps a), b) and c)) and 3-furancarboxylic acid hydrazide (prepared as described in WO 99/06407), instead of 4-tert-butyl-5-formyl-3-(p-toluenesulfonyloxy)pyrazole and 2,5-difluorobenzoic hydrazide respectively, in step e). Data for the title compound: mp=148° C.; $^1$H NMR (400 MHz, CDCl$_3$) δ 3.98 (3H, s), 5.75 (2H, s), 7.22–7.30 (2H, m), 7.39–7.43 (1H, m), 7.47 (1H, m), 7.57 (1H, m), 7.63 (1H, m), 7.92 (1H, s), 9.12 (1H, s), 9.19 (1H, s); MS (ES$^+$) m/e 392 [MH]$^+$; Anal. Found: C, 58.11; H, 3.41; N, 24.93%. C$_{19}$H$_{14}$FN$_7$O$_2$ requires: C, 58.31; H, 3.61; N, 25.05%.

EXAMPLE 81

3,7-bis(2-Fluorophenyl)-2-(1-methyl-1H-benzimidazol-2-ylmethoxy)pyrazolo[1,5-d][1,2,4]triazine a) (1-Methyl-1H-benzimidazol-2-yl)methanol 1-Methylbenzimidazole (5.0 g, 0.038 mol) was stirred at reflux in 37 wt % aqueous formaldehyde (50 ml) for 24 h. The solution was allowed to cool to room temperature then basified with saturated sodium hydrogen carbonate solution and then extracted with. dichloromethane (3×50 ml). The combined organic layers were dried over magnesium sulfate and were concentrated in vacuo. The residue was purified by flash chromatography on silica gel, eluting with 2.5 to 10% methanol in dichloromethane. The resultant semi-solid was triturated with isohexane to yield a solid, which was then recrystallised from ethyl acetate/isohexane, yielding (1-methyl-1H-benzimidazol-2-yl)methanol as a white solid (0.71 g). Data for the title compound: $^1$H NMR (400 MHz, CDCl$_3$) δ 3.81 (3H, s), 4.89 (2H, s), 7.26 (3H, m), 7.69 (1H, m); MS (ES$^+$) m/e 163 [MH]$^+$.

b) 3,7-bis(2-Fluorophenyl)-2-(1-methyl-1H-benzimidazol-2-ylmethoxy)pyrazolo[1,5-d][1,2,4]triazine This compound was prepared using the procedure described in Example 58, using (1-methyl-1H-benzimidazol-2-yl)methanol instead of (2-ethyl-2H-[1,2,4]triazol-3-yl)methanol in step f). Data for the title compound: mp=218–220° C.; $^1$H NMR (400 MHz, CDCl$_3$) δ 3.75 (3H, s), 5.71 (2H, s), 7.20–7.41 (8H, m), 7.60–7.67 (2H, m), 7.77 (1H, dd, J=7.6, 1.2 Hz), 7.83 (1H, m), 9.28 (1H, s); MS (ES$^+$) m/e 469 [MH]$^+$; Anal. Found: C, 66.31; H, 3.69: N, 17.88%. C$_{26}$H$_{18}$F$_2$N$_6$O requires: C, 66.66; H, 3.87; N, 17.94%.

EXAMPLE 82

3,7-bis(2-Fluorophenyl)-2-([1,2,4]triazolo[1,5-a]pyridin-2-ylmethoxy)pyrazolo[1,5-d][1,2,4]triazine a) [1,2,4]Triazolo[1,5-a]pyridin-2-ylmethanol To ethyl [1,2,4]triazolo[1,5-a]pyridine-2-carboxylate (prepared as described in *J. Chem. Soc., Perkin Trans.* 1, 1976, 2166) (0.67 g, 3.5 mmol) in THF (10 ml) was added lithium borohydride (78 mg, 3.6 mmol) and the mixture was stirred at room temperature under nitrogen overnight. The solvent was removed in vacuo and the residue was purified by flash chromatography on silica gel, eluting with 2.5 to 5% methanol in dichloromethane. The resultant solid was recrystallised from ethyl acetate, yielding [1,2,4]triazolo[1,5-a]pyridin-2-ylmethanol as a white solid (0.054 g). Data for the title compound: $^1$H NMR (400 MHz, CDCl$_3$) δ 2.83 (1H, br s), 4.97 (2H, s), 7.03 (1H, t, J=6.9 Hz), 7.54 (1H, t, J=7.0 Hz), 7.72 (1H, d, J=9.0 Hz), 8.56 (1H, d, J=6.0 Hz); MS (ES$^+$) m/e 150 [MH]$^+$.

b) 3,7-bis(2-Fluorophenyl)-2-([1,2,4]triazolo[1,5a]pyridin-2-ylmethoxy)pyrazolo[1,5-d][1,2,4]triazine This compound was prepared using the procedure described in Example 58, using [1,2,4]triazolo[1,5-a]pyridin-2-ylmethanol instead of (2-ethyl-2H-[1,2,4]triazol-3-yl)methanol in step f). Data for the title compound: mp=208–209° C.; $^1$H NMR (400 MHz, CDCl$_3$) δ 5.71 (2H, s), 7.04 (1H, m), 7.22 (3H, m), 7.34 (2H, m), 7.54 (1H, m), 7.62 (1H, m), 7.73 (1H, m), 7.80 (2H, m), 8.55 (1H, d, J=7.0 Hz), 9.28 (1H, s); MS (ES$^+$) m/e 456 [NH]$^+$.

EXAMPLE 83

3,7-bis(2-Fluorophenyl)-2-(5,6,7,8-tetrahydro[1,2,4]triazolo[1,5-a]pyridin-2-ylmethoxy)pyrazolo[1,5-d][1,2,4]triazine a) (5,6,7,8-Tetrahydro[1,2,4]triazolo[1,5-a]pyridin-2-yl)methanol

[1,2,4]Triazolo[1,5-a]pyridin-2-ylmethanol (prepared as described in Example 82, step a)) (150 mg, 1.0 mmol) in ethanol (10 ml) was hydrogenated on a Parr apparatus at 50 psi over 10% palladium on carbon (150 mg) overnight. The catalyst was separated by filtration, then the filtrate was concentrated in vacuo to yield (5,6,7,8-tetrahydro-[1,2,4]triazolo[1,5-a]pyridin-2-yl)methanol as a white solid (153 mg). Data for the title compound: $^1$H NMR (360 MHz, CDCl$_3$) δ 1.97 (2H, m), 2.07 (2H, m), 2.90 (2H, t, J=6.3 Hz), 3.00 (1H, br s), 4.13 (2H, t, J=6.0 Hz), 4.70 (2H, s); MS (ES$^+$) m/e 154 [MH]$^+$.

b) 3,7-bis(2-Fluorophenyl)-2-(5,6,7,8-tetrahydro[1,2,4]triazolo[1,5-a]pyridin-2-ylmethoxy)pyrazolo[1,5-d][1,2,4]triazine This compound was prepared using. the procedure described in Example 58, using (5,6,7,8-tetrahydro[1,2,4]triazolo[1,5-a]pyridin-2-yl)methanol instead of (2-ethyl-2H-[1,2,4]triazol-3-yl)methanol in step f). Data for the title compound: mp=150–152° C.; $^1$H NMR (400 MHz, CDCl$_3$) δ 1.98 (2H, m), 2.07 (2H, m), 2.90 (2H, t, J=6.3 Hz), 4.13 (2H, t, J=6.0 Hz), 5.45 (2H, s), 7.19–7.29 (3H, m), 7.32–7.39 (2H, m), 7.62 (1H, m), 7.75 (1H, m), 7.85 (1H, m), 9.26 (1H, s); MS (ES$^+$) m/e 460 [MH]$^+$; Anal. Found: C, 61.93; H, 3.90; N, 21.02%. C$_{24}$H$_{19}$F$_2$N$_7$O.0.5H$_2$O requires: C, 61.53; H, 4.30; N, 20.93%.

EXAMPLE 84

2-[3,7-bis(2-Fluorophenyl)pyrazolo[1,5-d][1,24]triazin-2-yloxymethyl]-5,6,7,8-tetrahydro-[1,2,4]triazolo[1,5-a]pyrazine Hydrochloride a) [1,2,4]Triazolo[1,5-a]pyrazine-2-carboxylic Acid Ethyl Ester Ethyl 1,2,4-triazolo[1,5-a]pyrazine-2-carboxylate-3-oxide (prepared as described in *J. Chem. Soc., Perkin Trans.* 1, 1976, 2166) (2.0 g, 9.6 mmol) was stirred in triethyl phosphite (20 ml) at 100° C. for 1 h. The solvent was concentrated in vacuo, and the crude product was triturated with diethyl ether (50 ml). The precipitated solid was separated by filtration, and purified by flash chromatography on silica gel, eluting with 1:1 dichloromethane:ethyl acetate, yielding [1,2,4]triazolo[1,5-a]pyrazine-2-carboxylic acid ethyl ester as a pale orange solid (420 mg). Data for the title compound: $^1$H NMR (360 MHz, CDCl$_3$) δ 1.51 (3H, t, J=7.1

Hz), 4.59 (2H, q, J=7.1 Hz), 8.34 (1H, d, J=4.5 Hz), 8.63 (1H, d, J=4.5 Hz), 9.43 (1H, s); MS (ES$^+$) m/e 193 [MH]$^+$.

b) 5,6-Dihydro-8H-[1,2,4]triazolo[1,5-a]pyrazine-2,7-dicarboxylic Acid 7-tert-Butyl Ester 2-Ethyl Ester

[1,2,4]Triazolo[1,5-a]pyrazine-2-carboxylic acid ethyl ester (0.75 g, 3.9 mmol) was hydrogenated on a Parr apparatus at 45 psi in dioxane (50 ml) over 10% palladium on carbon (0.75 g) in the presence of di-tert-butyl dicarbonate (0.85 g, 3.9 mmol) for 3 days. The catalyst was separated by filtration, and the filtrate was concentrated in vacuo. The residue was purified by passing through a plug of silica, eluting with 25% ethyl acetate in dichloromethane, yielding 5,6-dihydro-8H-[1,2,4]triazolo[1,5-a]pyrazine-2,7-dicarboxylic acid 7-tert-butyl ester 2-ethyl ester as a colourless oil (1.0 g). Data for the title compound: $^1$H NMR (360 MHz, CDCl$_3$) δ 1.44 (3H, t, J=7.2 Hz), 1.50 (9H, s), 3.97 (2H, t, J=5.4 Hz), 4.29 (2H, t, J=5.5 Hz), 4.48 (2H, q, J=7.1 Hz), 4.80 (2H, s); MS (ES$^+$) m/e 297 [MH]$^+$.

c) 2-Hydroxymethyl-5,6-dihydro-8H-[1,2,4]triazolo 1,5-a] pyrazine-7-carboxylic Acid tert-Butyl Ester To 5,6-dihydro-8H-[1,2,4]triazolo[1,5-a]pyrazine-2,7-dicarboxylic acid 7-tert-butyl ester 2-ethyl ester (0.90 g, 3.0 mmol), in THF (20 ml) was added lithium borohydride (73 mg, 3.4 mmol), and the resultant mixture was stirred at room temperature overnight. Citric acid solution (10%, 25 ml) was added, then the mixture was washed with dichloromethane (2×50 ml). The combined organic layers were dried over magnesium sulfate and concentrated in vacuo. The residue was purified by flash chromatography on silica gel, eluting with ethyl acetate and then 5% methanol in ethyl acetate, yielding 2-hydroxymethyl-5,6-dihydro-8H-[1,2,4]triazolo [1,5-a]pyrazine-7-carboxylic acid tert-butyl ester as a colourless oil (330 mg). Data for the title compound: $^1$H NMR (400 MHz, CDCl$_3$) δ 1.50 (9H, s), 2.41 (1H, br s), 3.93 (2H, t, J=5.3 Hz), 4.18 (2H, t, J=5.4 Hz), 4.74 (4H, s); MS (ES$^+$) m/e 255 [MH]$^+$.

d) 2-[3,7-bis(2-Fluorophenyl)pyrazolo[1,5-d][1,2,4]triazin-2-yloxymethyl]-5,6-dihydro-8H-[1,2,4]triazolo[1,5-a] pyrazine-7-carboxylic Acid tert-Butyl Ester This compound was prepared as described in Example 58, but using 2-hydroxymethyl-5,6-dihydro-8H-[1,2,4]triazolo [1,5-a]pyrazine-7-carboxylic acid tert-butyl ester instead of (2-ethyl-2H-[1,2,4]triazol-3-yl)methanol in step f). Data for the title compound: $^1$H NMR (400 MHz, CDCl$_3$) δ 1.48 (9H, s), 3.93 (2H, t, J=5.3 Hz), 4.17 (2H, t, J=5.3 Hz), 4.73 (2H, s), 5.47 (2H, s), 7.22–7.27 (3H, m), 7.37 (2H, m), 7.62 (1H, m), 7.73 (1H, m), 7.83 (1H, mn), 9.27 (1H, s); MS (ES$^+$) m/e 561 [MH]$^+$.

e) 2-[3,7-bis(2-Fluorophenyl)pyrazolo[1,5-d][1,2,4]triazin-2-yloxymethyl]-5,6,7,8-tetrahydro-[1,2,4]triazolo[1,5-a] pyrazine Hydrochloride To 2-[3,7-bis(2-Fluorophenyl)pyrazolo[1,5-d][1,2,4] triazin-2-yloxymethyl]-5,6-dihydro-8H-[1,2,4]triazolo[1,5-a]pyrazine-7-carboxylic acid tert-butyl ester (100 mg, 0.18 mmol) in ethyl acetate (3 ml) was added a saturated solution of hydrogen chloride in: ethyl acetate (2 ml), and the resultant mixture was stirred at room temperature for 5.5 h. 2-[3,7-Bis(2-fluorophenyl)pyrazolo[1,5-d][1,2,4]triazin-2-yloxymethyl]-5,6,7,8-tetrahydro-[1,2,4]triazolo[1,5-a] pyrazine hydrochloride was precipitated as a pale yellow solid, and was separated by filtration, washed thoroughly with ethyl acetate and dried (71 mg). Data for the title compound: $^1$H NMR (360 MHz, DMSO) δ 3.67 (2H, m), 4.37 (2H, t, J=5.8 Hz), 4.48 (2H, s), 5.39 (2H, s), 7.33–7.55 (5H, m), 7.69 (1H, td, J=7.6, 1.7 Hz), 7.77 (1H, m), 7.92 (1H, td, J=7.3, 1.7 Hz), 9.44 (1H, s), 10.07 (2H, br s); MS (ES$^+$) m/e 461 [MH]$^+$.

EXAMPLE 85

2-[2-(2,2-Difluoroethyl)-2H-[1,2,4]triazol-3-ylmethoxy]-3,7-bis(2-fluorophenyl)pyrazolo[1,5-d] [1,2,4]triazine a) 1-(2,2-Difluoroethyl)-1H-[1,2,4]triazole To a solution of [1,2,4]triazole (7.3 g, 0.11 mol), triphenylphosphine (33 g, 0.13 mol) and 2,2-difluoroethanol (8.0 ml, 10 g, 0.13 mol) in THF (115 ml) was added diethyl azodicarboxylate (20 ml, 22 g, 0.13 mol) dropwise, maintaining the temperature of the mixture between −5 and 0° C. throughout the addition. The resultant solution was allowed to warm to room temperature and was stirred under nitrogen overnight. The solvent was removed it uacuo, and diethyl ether (220 ml) was added to the residue, precipitating a solid. This was separated by filtration, and the filtrate was concentrated in vacuo. The residual oil was purified by distillation under vacuum, yielding 1-(2,2-difluoroethyl)-1H-[1,2,4]triazole as a yellow oil (7.1 g). Data for the title compound: $^1$H NMR (250 MHz, CDCl$_3$) δ 4.56 (2H, td, J=13.5, 4.1 Hz), 6.13 (1H, tt, J=55.1, 4.2 Hz), 8.01 (1H, s), 8.18 (1H, s).

b) [2-(2,2-Difluoroethyl)-2H-[1,2,4]triazol-3-yl]methanol 1-(2,2-Difluoroethyl)-1H-[1,2,4]triazole (4.0 g, 0.030 mol) was heated at reflux in 37% aqueous formaldehyde for 2 days. The solution was allowed to cool to room temperature and was washed with dichloromethane (3×50 ml). The solution was then saturated with sodium chloride, and washed again with dichloromethane (3×50 ml). The combined organic washings were dried over magnesium sulfate and concentrated in vacuo. The residue was purified by flash chromatography on silica gel, eluting with 0 to 7.5% methanol in dichloromethane, yielding [2-(2,2-difluoroethyl)-2H-[1,2,4]triazol-3-yl]methanol as a solid (2.4 g). Data for the title compound: $^1$H NMR (250 MHz, CDCl$_3$) δ 4.65 (2H, td, J=13.2, 4.3 Hz), 4.83 (2H, s), 6.17 (1H, tt, J=55.2,4.3 Hz), 7.86 (1H, s).

c) 2-[2-(2,2-Difluoroethyl)-2H-[1,2,4]triazol-3-ylmethoxy]-3,7-bis(2-fluorophenyl)pyrazolo[1,5-d][1,2,4]triazine This compound was prepared as described in Example 58, but using [2-(2,2-difluoroethyl)-2H-[1,2,4]triazol-3-yl] methanol instead of (2-ethyl-2H-[1,2,4]triazol-3-yl) methanol in step f). Data for the title compound: mp=179–180° C.; $^1$H NMR (400 MHz, CDCl$_3$) δ 4.38 (2H, td, J=13.4, 4.3 Hz), 5.56 (2H, s), 5.97 (1H, tt, J=55.2, 4.2 Hz), 7.23–7.35 (3H, m), 7.42 (2H, m), 7.61–7.69 (2H, m), 7.80 (1H, m), 7.92 (1H, s), 9.28 (1H, s); MS (ES$^+$) m/e 470 [MH]$^+$; Anal. Found: C, 56.22; H, 3.00; N, 20.74%. C$_{22}$H$_{15}$F$_4$N$_7$O requires; C, 56.29; H, 3.22; N, 20.89%.

EXAMPLE 86

2-[2-(2-Fluoroethyl)-2H-[1,2,4]triazol-3-ylmethoxy]-3,7-bis(2-fluorophenyl)-pyrazolo[1,5-d] [1,2,4]triazine a) 1-(2-Fluoroethyl)-1H-[1,2,4]triazole This compound was prepared as described in Example 85 step a), but using 2-fluoroethanol instead of 2,2-difluoroethanol. Data for the title compound: $^1$H NMR (250 MHz, CDCl$_3$) δ 4.49 (2H, dt, J=26.6, 4.5 Hz), 4.78 (2H, dt, J=46.7, 4.6 Hz), 7.99 (1H, s), 8.16 (1H, s).

b) [2-(2-Fluoroethyl)-2H-[1,2,4]triazol-3-yl]methanol

This compound was prepared as described in Example 85 step b), but using 1-(2-fluoroethyl)-1H-[1,2,4]triazole instead of 1-(2,2-difluoroethyl)-1H-[1,2,4]triazole. Data for the title compound: $^1$H NMR (250 MHz, CDCl$_3$) δ 3.93 (1H, br s), 4.55 (2H, dt, J=25.7, 4.7 Hz), 4.80 (2H, s), 4.81 (2H, dt, J=46.7, 4.7 Hz), 7.84 (1H, s).

c) 2-[2-(2-Fluoroethyl)-2H-[1,2,4]triazol-3-ylmethoxy]-3,7-bis(2-fluorophenyl)pyrazolo[1,5-d][1,2,4]triazine This compound was prepared as described in Example 58, but using [2-(2-fluoroethyl)-2H-[1,2,4]triazol-3-yl]methanol instead of (2-ethyl-2H-[1,2,4]triazol-3-yl)methanol in step f). Data for the title compound: mp=172–173° C.; $^1$H NMR (400 MHz, CDCl$_3$) δ 4.34 (2H, dt, J=26.0, 4.7 Hz), 4.61 (2H, dt, J=46.8, 4.7 Hz), 5.56 (2H, s), 7.25–7.34 (3H, m), 7.40–7.43 (2H, m), 7.64–7.66 (2H, m), 7.81 (1H, m), 7.91 (1H, s), 9.28 (1H, s); MS (ES$^+$) m/e 452 [MH]$^+$; Anal. Found: C, 58.48; H, 3.37; N, 21.59%. C$_{22}$H$_{16}$F$_3$N$_7$O requires: C, 58.54; H, 3.57; N, 21.72%.

EXAMPLE 87

7-(2,5-Difluorophenyl)-3-(2-fluorophenyl)-2(2-methyl-2H-[1,2,4]triazol-3-ylmethoxy)pyrazolo[1,5-d][1,2,4]triazine This compound was prepared using the procedure described in Example 21, steps b) to f), using 3-(2-fluorophenyl)-4-hydroxy-2-furanone instead of 3-tert-butyl-4-hydroxy-2-furanone. Data for the title compound: mp=176–175° C.; $^1$H NMR (400 MHz, CDCl$_3$) δ 3.83 (3H, s), 5.56 (2H, s), 7.23–7.42 (5H, m), 7.53–7.63 (2H, m), 7.86 (1H, m), 9.28 (1H, s); MS (ES$^+$) m/e 438 [MH]$^+$; Anal. Found: C, 57.45; H, 3.17; N, 22.48%. C$_{21}$H$_{14}$F$_3$N$_7$O requires: C, 57.67; H, 3.23; N, 22.42%.

EXAMPLE 88

7-(2-Chlorophenyl)-3-(2-fluorophenyl)-2-(2-methyl-2H-[1,2,4]triazol-3-ylmethoxy)pyrazolo[1,5-d][1,2,4]triazine This compound was prepared using the procedure described in Example 21, steps b) to 1), using 3-(2-fluorophenyl)-4-hydroxy-2-furanone instead of 3-tert-butyl-4-hydroxy-2-furanone and 2-chlorobenzoic hydrazide instead of 2,5-difluorobenzoic hydrazide. Data for the title compound: mp=155–157° C.; $^1$H NMR (400 MHz, CDCl$_3$) δ 3.68 (3H, s), 5.49 (2H, s), 7.27 (2H, m), 7.38–7.86 (6H, m), 7.84 (1H, s), 9.30 (1H, s); MS (ES$^+$) m/e 436 [MH]$^+$; Anal. Found: C, 57.44; H, 3.14; N, 21.84%. C$_{21}$H$_{15}$ClFN$_7$O.0.1EtOAc requires: C, 57.81; H, 3.58; N, 22.05%.

EXAMPLE 89

7-Cyclopropyl-3-(2-fluorophenyl)-2-(2-methyl-2H-[1,2,4]triazol-3-ylmethoxy)pyrazolo[1,5-d][1,2,4]triazine This compound was prepared using the procedure described in Example 21, steps b) to f), using 3-(2-fluorophenyl)-4-hydroxy-2-furanone instead of 3-tert-butyl-4-hydroxy-2-furanone and cyclopropyl hydrazide instead of 2,5-difluorobenzoic hydrazide. Data for the title compound: mp=97–99° C.; $^1$H NMR (400 MHz, CDCl$_3$) δ 1.31 (2H, m), 1.59 (2H, m), 2.94 (1H, m), 3.98 (3H, s), 5.71 (2H, s), 7.23 (2H, m), 7.37 (1H, m), 7.56 (1H, m), 7.89 (1H, s), 9.06 (1H, s); MS (ES$^+$) m/e 366; [MH]$^+$.

EXAMPLE 90

3,7-bis(2-Fluorophenyl)-2-(1,5-dimethyl-1H-pyrazol-3-ylmethoxy)-pyrazolo[1,5-d][1,2,4]triazine This compound was prepared using the procedure described in Example 21, steps b) to f), using 3-(2-fluorophenyl)-4-hydroxy-2-furanone instead of 3-tert-butyl-4-hydroxy-2-furanone, 2-fluorobenzoic hydrazide instead of 2,5-difluorobenzoic hydrazide, and (1,5-dimethyl-1H-pyrazol-3-yl)methanol instead of (2-methyl-2H-[1,2,4]triazol-3-yl)methanol. Data for the title compound: mp=183° C.; $^1$H NMR (400 MHz, CDCl$_3$) δ 2.23 (3H, s), 3.73 (3H, s), 5.35 (2H, s), 6.05 (1H, s), 7.19–7.40 (5H, m), 7.61 (2H, m), 7.76 (1H, m), 9.24 (1H, s); MS (ES$^+$) m/e 433 [MH]$^+$; Anal. Found: C, 63.31; H, 3.97; N, 19.31%. C$_{23}$H$_{18}$F$_2$N$_6$O.0.1H$_2$O requires: C, 63.62; H, 4.23; N, 19.35%.

EXAMPLE 91

2-(2-Ethyl-2H-[1,2,4]triazol-3-ylmethoxy)-7-(2-fluorophenyl)-3-(furan-2-yl)pyrazolo[1,5-d][1,2,4]triazine This was prepared in 59% yield using a similar procedure to that described in Example 53 except using 2-(tributylstannyl)furan instead of 2-(tributylstannyl)pyridine and 3-bromo-2-(2-ethyl-2H-[1,2,4]triazol-3-ylmethoxy)-7-(2-fluorophenyl)pyrazolo[1,5-d][1,2,4]triazine instead of 3-bromo-7-(2-fluorophenyl)-2-(2-methyl-2H-[1,2,4]triazol-3-ylmethoxy)-pyrazolo[1,5-d][1,2,4]triazine. Data for title compound: mp=182–183° C. (CH$_2$Cl$_2$-EtOAc); $^1$H NMR (360 MHz, CDCl$_3$) δ 1.39 (3H, t, J=7.3 Hz), 4.17 (2H, q, J=7.3 Hz), 5.59 (2H, s), 6.51 (1H, m), 6.70 (1H, m), 7.28 (1H, m), 7.39 (1H, dt, J=7.6 and 0.9 Hz), 7.56 (1H, m), 7.65 (1H, m), 7.81 (1H, m), 7.90 (1H, s), 9.69 (1H, s); MS (ES$^+$) m/e 406 [MH]$^+$; Anal. Found C, 58.57; H, 4.08; N, 23.87%. C$_{20}$H$_{16}$FN$_7$O$_2$.0.3H$_2$O requires C, 58.48; H, 4.07; N, 23.87%.

EXAMPLE 92

2-(2-Ethyl-2H-[1,2,4]triazol-3-ylmethoxy)-7-(2-fluorophenyl)-3-(thien-2-yl)pyrazolo[1,5-d][1,2,4]triazine This was prepared in 59% yield using a similar procedure to that described in Example 53 except using 2-(tributylstannyl)thiophene instead of 2-(tributylstannyl)pyridine and 3-bromo-2-(2-ethyl-2H-[1,2,4]triazol-3-ylmethoxy)-7-(2-fluorophenyl)pyrazolo[1,5-d][1,2,4]triazine instead of 3-bromo-7-(2-fluorophenyl)-2-(2-methyl-2H-[1,2,4]triazol-3-ylmethoxy)-pyrazolo[1,5-d][1,2,4]triazine. Data for title compound: mp=190–192° C. (CH$_2$Cl$_2$-EtOAc); $^1$H NMR (360 MHz, CDCl$_3$) δ 1.39 (3H, t, J=7.3 Hz), 4.18 (2H, q, J=7.3 Hz), 5.60 (2H, s), 7.15 (1H, m), 7.29 (1H, t, J=9.4 Hz), 7.38–7.42 (2H, m), 7.46 (1H, d, J=3.6 Hz), 7.66 (1H, m), 7.81 (1H, m), 7.90 (1H, s), 9.56 (1H, s); MS (ES$^+$) m/e 422 [MH]$^+$; Anal. Found C, 57.30; H, 3,71; N, 23.35%. C$_{20}$H$_{16}$FN$_7$OS requires C, 57.00; H, 3.83; N, 23.26%.

EXAMPLE 93

2-(2-Ethyl-2H-[1,2,4]triazol-3-ylmethoxy)-7-(2-fluorophenyl)-3-(thien-3-yl)pyrazolo[1,5-d][1,2,4]triazine This was prepared in 86% yield using a similar procedure to that described in Example 18 except using thiophene-3-boronic acid instead of 3-trifluoromethylbenzeneboronic acid and 3-bromo-2-(2-ethyl-2H-[1,2,4]triazol-3-ylmethoxy)-7-(2-fluorophenyl)pyrazolo[1,5-d][1,2,4]triazine instead of 3-bromo-7-(2-fluorophenyl)-2-(2-methyl-2H-[1,2,4]triazol-3-ylmethoxy)pyrazolo[1,5-d][1,2,4]

triazine. Data for title compound: mp=187–193° C. (CH₂Cl₂-EtOAc); ¹H NMR (400 MHz, CDCl₃) δ 1.35 (3H, t, J=7.3 Hz), 4.14 (2H, q, J=7.3 Hz), 5.59 (2H, s), 7.29 (1H, m), 7.40 (1H, td, J=7.6 and 0.8 Hz), 7.48 (1H, s), 7.49 (1H, s), 7.64–7.66 (2H, m), 7.81 (1H, m), 7.90 (1H, s), 9.46 (1H, s); MS (ES⁺) m/e 422 [MH]⁺; Anal. Found C, 56.14; H, 3.84; N, 22.75%. $C_{20}H_{16}FN_7OS.0.3H_2O$ requires C, 56.28; H, 3.92; N, 22.97%.

EXAMPLE 94

3-(3-Aminophenyl)-7-(2-fluorophenyl)-2-(2-methyl-2H-[1,2,4]triazol-3-ylmethoxy)pyrazolo[1,5-d][1,2,4]triazine This was prepared in 43% yield using a similar procedure to that described in Example 18 except using 3-aminobenzeneboronic acid hemisulfate instead of 3-trifluoromethylbenzeneboronic acid. Data for title compound: mp=196–200° C. (CH₂Cl₂-EtOAc-isohexane); ¹H NMR (360 MHz, CDCl₃) δ 3.76 (3H, s), 3.82 (2H, br s), 5.54 (2H, s), 6.71 (1H, dd, J=7.8 and 1.8 Hz), 6.98 (1H, t, J=1.8 Hz), 7.02 (1H, d, J=7.7 Hz), 7.27 (1H, t, J=7.7 Hz), 7.29 (1H, m), 7.39 (1H, t, J=. 7.5 Hz), 7.65 (1H, m), 7.79 (1H, m), 7.86 (1H, s), 9.42 (1H, s); MS (ES⁺) m/e417 [MH]⁺; Anal. Found C, 59.42; H, 3.93; N, 26.06%. $C_{21}H_{17}FN_8O.0.08CH_2Cl_2.0.03C_4H_8O_2$ requires C, 59.79; H, 4.12; N, 26.31%.

EXAMPLE 95

7-(2-Fluorophenyl)-2-(2-methyl-2H-[1,2,4]triazol-3-ylmethoxy)-3-[3-(pyridin-3-yl)phenyl]pyrazolo[1,5-d][1,2,4]triazine This was prepared in 69% yield using a similar procedure to that described in Example 53 except using 3-[3-(tributylstannyl)phenyl]-pyridine instead of 2-(tributylstannyl)pyridine. Data for title compound: mp=157–163° C. (CH₂Cl₂-EtOAc-isohexane); ¹H NMR (400 MHz, CDCl₃) δ 3.76 (3H, s), 5.58 (2H, s), 7.31 (1H, t, J=8.8 Hz), 7.41 (2H, m), 7.61–7.72 (4H, m), 7.81 (1H, m), 7.86–7.91 (3H, m), 8.65 (1H, m), 8.89 (1H, s), 9.47 (1H, s); MS (ES⁺) m/e 479 [MH]⁺; Anal. Found C, 64.46; H, 3.88; N, 22.92%. $C_{26}H_{19}FN_8O.0.04CH_2Cl_2.0.03C_4H_8O_2$ requires C, 64.85; H, 4.02; N, 23.13%.

EXAMPLE 96

7-(2-Fluorophenyl)-3-iodo-2-(2-methyl-2H-[1,2,4]triazol-3-ylmethoxy)-pyrazolo[1,5-d][1,2,4]triazine a) 7-(2-Fluorophenyl)-3-iodopyrazolo[1,5-d][1,2,4]triazin-2-ol To a stirred mixture of 7-(2-fluorophenyl)pyrazolo[1,5-d][1,2,4]triazin-2-ol (0.5014 g, 2.18 mmol) in glacial acetic acid (10 ml) was added dropwise a 1.0 M solution of iodine monochloride in glacial acetic acid (3.26 ml, 3.26 mmol) and the mixture was stirred at room temperature for a total of 1.25 h. Water (40 ml) was then added and the resulting solid was collected by filtration, washed with water, and dried under vacuum at 60° C. to yield 0.7345 g (95%) of the title compound as a pale brown solid; ¹H NMR (360 MHz, d₆-DMSO) δ 7.42–7.49 (2H, m), 7.71 (1H, m), 7.79 (1H, m), 9.26 (1H, s), 12.48 (1H, s); MS (ES⁺) m/e 357 [MH]⁺.

b) 7-(2-Fluorophenyl)-3-iodo-2-(2-methyl-2H-[1,2,4]triazol-3-ylmethoxy)pyrazolo[1,5-d][1,2,4]triazine To a stirred solution of 7-(2-fluorophenyl)-3-iodopyrazolo[1,5-d][1,2,4]triazin-2-ol (0.4098 g, 1.15 mmol) in anhydrous DMF (16 ml) under nitrogen was added cesium carbonate (1.5009 g, 4.61 mmol), then solid 3-chloromethyl-2-methyl-2H-[1,2,4]triazole hydrochloride (0.2328 g, 1.39 mmol). The mixture was stirred at room temperature for 25 h, then partitioned between water (75 ml) and ethyl acetate (75 ml). The aqueous layer was further extracted with ethyl acetate (2×75 ml), and the combined organic extracts were dried (Na₂SO₄) and evaporated in vacuo. The residue was purified by flash chromatography (silica gel, 0–5% MeOH/EtOAc) to give 0.4212 g (81%) of the title compound as a white solid: mp=218–219° C. (CH₂Cl₂-EtOAc); ¹H NMR (360 MHz, CDCl₃) δ 3.88 (3H, s), 5.52 (2H, s), 7.28 (1H, m), 7.39 (1H, td, J=7.6 and 1.0 Hz), 7.65 (1H, m), 7.76 (1H, m), 7.87 (1H, s), 9.14 (1H;, s); MS (ES⁺) m/e 452 [MH]⁺; Anal. Found C, 39.66; H, 2.16; N, 21.34%. $C_{15}H_{11}FIN_7O$ requires C, 39.93; H, 2.46; N, 21.73%.

EXAMPLE 97

3-(3-Cyanophenyl)-7-(2-fluorophenyl)-2-(2-methyl-2H-[1,2,4]triazol-3-ylmethoxy)pyrazolo[1,5-d][1,2,4]triazine This was prepared in 43% yield using a similar procedure to that described in Example 18 except using 3-cyanobenzeneboronic acid instead of 3-trifluoromethylbenzeneboronic acid. Data for title compound: mp=194–196° C. (CH₂Cl₂-EtOAc-isohexane); ¹H NMR (400 MHz, CDCl₃) δ 3,75 (3H, s), 5.57 (2H, s), 7.31 (1H, m), 7.42 (1H,.td, J=7.7 and 1.0 Hz), 7.65–7.70 (3H, m), 7.79 (1H, m), 7.86 (1H, s), 7.91 (1H, dt, J=7.7 and 1.5 Hz), 7.98 (1H, m), 9.43 (1H, s); MS (ES⁺) m/e 427 [MH]⁺; Anal. Found C, 56.03; H, 3.17; N. 23.07%. $C_{22}H_{15}FN_8O.0.53CH_2Cl_2.0.45H_2O$ requires C, 56.43; H, 3.56; N, 23.37%.

What is claimed is:

1. A compound of formula I, or a salt thereof:

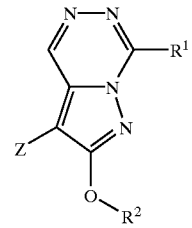

(I)

wherein

Z represents halogen; or $C_{1-6}$ alkyl, $C_{3-7}$ cycloalkyl, $C_{4-7}$ cycloalkenyl, $C_{6-8}$ bicycloalkyl, di($C_{1-6}$)alkylamino, phenyl, azetidinyl, pyrrolidinyl, piperidinyl, piperazinyl, morpholinyl, thiomorpholinyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl or tetrazolyl, which may be optionally substituted with a substitutent selected from $C_{1-6}$ alkyl, phenyl$C_{1-6}$ alkyl, halogen, cyano, hydroxy, hydroxymethyl, $C_{1-6}$ alkoxy and $C_{3-7}$ cycloalkyl$C_{1-6}$ alkyl;

$R^1$ represents $C_{3-7}$ cycloalkyl, phenyl, furyl, thienyl, pyridinyl or pyrazinyl, which may be optionally substituted with a substitutent selected from $C_{1-6}$ alkyl, phenyl$C_{1-6}$ alkyl, halogen, cyano, hydroxy, hydroxymethyl, $C_{1-6}$ alkoxy and $C_{3-7}$ cycloalkyl$C_{1-6}$ alkyl; and $R^2$ represents $C_{3-7}$ cycloalkyl($C_{1-6}$)alkyl, phenyl($C_{1-6}$ alkyl), azetidinyl($C_{1-6}$ alkyl), pyrrolidinyl($C_{1-6}$ alkyl), piperidinyl($C_{1-6}$ alkyl), piperazinyl($C_{1-6}$ alkyl), morpholinyl($C_{1-6}$ alkyl), thiomorpholinyl($C_{1-6}$ alkyl), pyridinyl($C_{1-6}$ alkyl), quinolinyl($C_{1-6}$ alkyl), isoquinolinyl($C_{1-6}$ alkyl), pyridazinyl($C_{1-6}$ alkyl), pyrimidinyl($C_{1-6}$ alkyl), pyrazinyl($C_{1-6}$ alkyl), quinoxalinyl($C_{1-6}$ alkyl), furyl($C_{1-6}$ alkyl), benzofuryl($C_{1-6}$ alkyl), dibenzofuryl($C_{1-6}$ alkyl), thienyl($C_{1-6}$ alkyl), benzthienyl($C_{1-6}$ alkyl), pyrrolyl($C_{1-6}$ alkyl), indolyl($C_{1-6}$ alkyl), pyrazolyl($C_{1-6}$ alkyl), indazolyl ($C_{1-6}$ alkyl), oxazolyl($C_{1-6}$ alkyl), isoxazolyl($C_{1-6}$ alkyl), thiazolyl($C_{1-6}$ alkyl), isothiazolyl($C_{1-6}$ alkyl), imidazolyl($C_{1-6}$ alkyl), benzimidazolyl($C_{1-6}$ alkyl), oxadiazolyl($C_{1-6}$ alkyl), thiadiazolyl($C_{1-6}$ alkyl), triazolyl($C_{1-6}$ alkyl) or tetrazolyl($C_{1-6}$ alkyl), which may be optionally substituted with a substituent selected from $C_{1-6}$ alkyl, phenyl$C_{1-6}$ alkyl, halogen, cyano, hydroxy, hydroxymethyl, $C_{1-6}$ alkoxy and $C_{3-7}$ cycloalkyl$C_{1-6}$ alkyl.

2. A compound as claimed in claim 1 wherein
Z represents $C_{1-6}$ alkyl, $C_{3-7}$ cycloalkyl, $C_{4-7}$ cycloalkenyl, $C_{6-8}$ bicycloalkyl, di($C_{1-6}$)alkylamino, phenyl, azetidinyl, pyrrolidinyl, piperidinyl, piperazinyl, morpholinyl, thiomorpholinyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl or tetrazolyl, which may be optionally substituted with a substituent selected from $C_{1-6}$ alkyl, phenyl$C_{1-6}$ alkyl, halogen, cyano, hydroxy, hydroxymethyl, $C_{1-6}$ alkoxy and $C_{3-7}$ cycloalkyl$C_{1-6}$ alkyl;

$R^1$ represents $C_{3-7}$ cycloalkyl, phenyl, furyl, thienyl or pyridinyl, which may be optionally substituted with a substituent selected from $C_{1-6}$ alkyl, phenyl$C_{1-6}$ alkyl, halogen, cyano, hydroxy, hydroxymethyl, $C_{1-6}$ alkoxy and $C_{3-7}$ cycloalkyl$C_{1-6}$ alkyl.

3. A compound as claimed in claim 1 represented by formula IIA, and salts thereof:

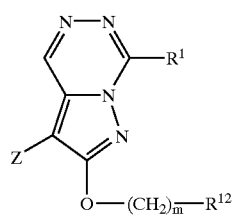

(IIA)

wherein
m is 1 or 2; and
$R^{12}$ represents phenyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl,; isoxazolyl, thiazolyl, isothiazolyl, imidazolyl, benzimidazolyl, oxadiazolyl, thiadiazolyl, triazolyl or tetrazolyl, which may be optionally substituted with a substituent selected from $C_{1-6}$ alkyl, phenyl$C_{1-6}$ alkyl, halogen, cyano, hydroxy, hydroxymethyl, $C_{1-6}$ alkoxy and $C_{3-7}$ cycloalkyl$C_{1-6}$ alkyl.

4. A compound represented by formula IIB, and pharmaceutically acceptable salts thereof:

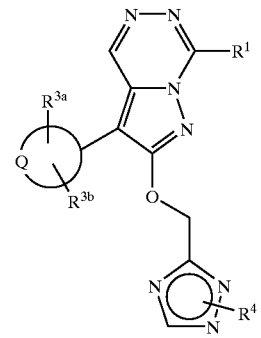

(IIB)

wherein
Q represents the residue of a cyclopropyl, cyclobutyl, cyclopentyl, cyclohexyl, phenyl, pyridinyl, furyl or thienyl ring;

$R^{3a}$ represents hydrogen, methyl, fluoro, chloro, trifluoromethyl, cyano or amino;

$R^{3b}$ represents hydrogen or fluoro; and $R^4$ represents hydrogen, methyl, ethyl, n-propyl, isopropyl, fluoroethyl or difluoroethyl.

5. A compound selected from:
7-(2-fluorophenyl)-2-(2-methyl-2H-[1,2,4]triazol-3-ylmethoxy)-3-phenyl-pyrazolo[1,5-d][1,2,4]triazine;
and salts thereof.

6. The compound of claim 1 which is selected from the group consisting of:
3-(2-fluorophenyl)-7-(2-fluorophenyl)-2-(2-methyl-2H-[1,2,4]triazol-3-ylmethoxy)pyrazolo[1,5-d][1,2,4]triazine;

3-(3-fluorophenyl)-7-(2-fluorophenyl)-2-(2-methyl-2H-[1,2,4]triazol-3-ylmethoxy)pyrazolo[1,5-d][1,2,4]triazine;

3-(4-fluorophenyl)-7-(2-fluorophenyl)-2-(2-methyl-2H-[1,2,4]triazol-3-ylmethoxy)pyrazolo[1,5-d][1,2,4]triazine;

2-(2-ethyl-2H-[1,2,4]triazol-3-ylmethoxy)-7-(2-fluorophenyl)-3-phenyl-pyrazolo[1,5-d][1,2,4]triazine;

7-(2-fluorophenyl)-2-(1-methyl-1H-[1,2,4]triazol-3-ylmethoxy)-3-phenyl-pyrazolo[1,5-d][1,2,4]triazine;

7-(3-fluorophenyl)-2-(2-methyl-2H-[1,2,4]triazol-3-ylmethoxy)-3-phenyl-pyrazolo[1,5-d][1,2,4]triazine;

7-(2-fluorophenyl)-3-phenyl-2-(pyridin-2-ylmethoxy)pyrazolo[1,5-d][1,2,4]triazine;

7-(4-fluorophenyl)-2-(2-methyl-2H-[1,2,4]triazol-3-ylmethoxy)-3-phenyl-pyrazolo[1,5-d][1,2,4]triazine;

7-(2,6-difluorophenyl)-2-(2-methyl-2H-[1,2,4]triazol-3-ylmethoxy)-3-phenyl-pyrazolo[1,5-d][1,2,4]triazine;

2-(2-methyl-2H-[1,2,4]triazol-3-ylmethoxy)-3-phenyl-7-(thien-2-yl)-pyrazolo[1,5-d][1,2,4]triazine;

3,7-diphenyl-2-(2-methyl-2H-[1,2,4]triazol-3-ylmethoxy)pyrazolo[1,5-d][1,2,4]triazine;

7-(2,5-difluorophenyl)-2-(2-methyl-2H-[1,2,4]triazol-3-ylmethoxy)-3-phenyl-pyrazolo[1,5-d][1,2,4]triazine;

3-(2,5-difluorophenyl)-7-(2-fluorophenyl)-2-(2-methyl-2H-[1,2,4]triazol-3-ylmethoxy)pyrazolo[1,5-d][1,2,4]triazine;

3-(2,6-difluorophenyl)-7-(2-fluorophenyl)-2-(2-methyl-2H-[1,2,4]triazol-3-ylmethoxy)pyrazolo[1,5-d][1,2,4]triazine;

3-(2,3-difluorophenyl)-7-(2-fluorophenyl)-2-(2-methyl-2H-[1,2,4]triazol-3-ylmethoxy)pyrazolo[1,5-d][1,2,4]triazine;

3-bromo-7-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-[3-(trifluoromethyl)phenyl]pyrazolo[1,5-d][1,2,4]triazine;

7-(2-fluorophenyl)-2-(2-methyl-2H-[1,2,4]triazol-3-ylmethoxy)-3-(thien-3-yl)pyrazolo[1,5-d][1,2,4]triazine;

3-(3,5-difluorophenyl)-7-(2-fluorophenyl)-2-(2-methyl-2H-[1,2,4]triazol-3-ylmethoxy)pyrazolo[1,5-d][1,2,4]triazine;

7-(2,5-difluorophenyl)-3-(1,1-dimethylethyl)-2-(2-methyl-2H-[1,2,4]triazol-3-ylmethoxy)pyrazolo[1,5-d][1,2,4]triazine;

7-(2,5-difluorophenyl)-3-(1,1-dimethylethyl)-2-(2-ethyl-2H-[1,2,4]triazol-3-ylmethoxy)pyrazolo[1,5-d][1,2,4]triazine;

7-(2,5-difluorophenyl)-3-(1,1-dimethylethyl)-2-(2-propyl-2H-[1,2,4]triazol-3-ylmethoxy)pyrazolo[1,5-d][1,2,4]triazine;

3-(1,1-dimethylethyl)-7-(2-fluorophenyl)-2-(2-methyl-2H-[1,2,4]triazol-3-ylmethoxy)pyrazolo[1,5-d][1,2,4]triazine;

3-(1,1-dimethylethyl)-2-(2-ethyl-2H-[1,2,4]triazol-3-ylmethoxy)-7-(2-fluorophenyl)pyrazolo[1,5-d][1,2,4]triazine;

3-(1,1-dimethylethyl)-7-(2-fluorophenyl)-2-(2-propyl-2H-[1,2,4]triazol-3-ylmethoxy)pyrazolo[1,5-d][1,2,4]triazine;

7-(2,5-difluorophenyl)-3-(1,1-dimethylpropyl)-2-(2-methyl-2H-[1,2,4]triazol-3-ylmethoxy)pyrazolo[1,5-d][1,2,4]triazine;

3-(1,1-dimethylethyl)-2-(2-methyl-2H-[1,2,4]triazol-3-ylmethoxy)-7-(2,3,6-trifluorophenyl)pyrazolo[1,5-d][1,2,4]triazine;

3-(1,1-dimethylethyl)-2-(2-ethyl-2H-[1,2,4]triazol-3-ylmethoxy)-7-(2,3,6-trifluorophenyl)pyrazolo[1,5-d][1,2,4]triazine;

7-(2,5-difluorophenyl)-3-(1,1-dimethylethyl)-2-(2-isopropyl-2H-[1,2,4]triazol-3-ylmethoxy)pyrazolo[1,5-d][1,2,4]triazine;

3-(2-fluorophenyl)-2-(2-methyl-2H-[1,2,4]triazol-3-ylmethoxy)-7-(pyrazin-2-yl)pyrazolo[1,5-d][1,2,4]triazine;

3-(2-chlorophenyl)-7-(2-fluorophenyl)-2-(2-methyl-2H-[1,2,4]triazol-3-ylmethoxy)pyrazolo[1,5-d][1,2,4]triazine;

7-(2,5-difluorophenyl)-3-(1,1-dimethylpropyl)-2-(2-ethyl-2H-[1,2,4]triazol-3-ylmethoxy)pyrazolo[1,5-d][1,2,4]triazine;

3-(1,1-dimethylpropyl)-7-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-(pyridin-3-yl)pyrazolo[1,5-d][1,2,4]triazine;

3-(2-fluorophenyl)-7-(furan-2-yl)-2-(2-methyl-2H-[1,2,4]triazol-3-ylmethoxy)pyrazolo[1,5-d][1,2,4]triazine;

3-(1,1-dimethylethyl)-7-(4-fluorophenyl)-2-(2-methyl-2H-[1,2,4]triazol-3-ylmethoxy)pyrazolo[1,5-d][1,2,4]triazine;

3-(1,1-dimethylethyl)-2-(2-ethyl-2H-[1,2,4]triazol-3-ylmethoxy)-7-(4-fluorophenyl)pyrazolo[1,5-d][1,2,4]triazine;

3-(1,1-dimethylethyl)-7-(4-fluorophenyl)-2-(2-propyl-2H-[1,2,4]triazol-3-ylmethoxy)pyrazolo[1,5-d][1,2,4]triazine;

3-(1,1-dimethylpropyl)-2-(2-ethyl-2H-[1,2,4]triazol-3-ylmethoxy)-7-(2-fluorophenyl)pyrazolo[1,5-d][1,2,4]triazine;

3-(2-fluorophenyl)-7-(4-fluorophenyl)-2-(2-methyl-2H-[1,2,4]-triazol-3-ylmethoxy)pyrazolo[1,5-d][1,2,4]triazine;

3-(3-chlorophenyl)-7-(2-fluorophenyl)-2-(2-methyl-2H-[1,2,4]triazol-3-ylmethoxy)pyrazolo[1,5-d][1,2,4]triazine;

3-(1,1-dimethylpropyl)-2-(2-methyl-2H-[1,2,4]triazol-3-ylmethoxy)-7-(2,3,6-trifluorophenyl)pyrazolo[1,5-d][1,2,4]triazine;

3-(1,1-dimethylpropyl)-2-(2-ethyl-2H-[1,2,4]triazol-3-ylmethoxy)-7-(2,3,6-trifluorophenyl)pyrazolo[1,5-d][1,2,4]triazine;

3-(2-fluorophenyl)-2-(2-methyl-2H-[1,2,4]triazol-3-ylmethoxy)-7-(pyridin-3-yl)pyrazolo[1,5-d][1,2,4]triazine;

2-(2-ethyl-2H-[1,2,4]triazol-3-ylmethoxy)-7-(2-fluorophenyl)-3-(pyridin-4-yl)pyrazolo[1,5-d][1,2,4]triazine;

2-(2-ethyl-2H-[1,2,4]triazol-3-ylmethoxy)-3-(2-fluorophenyl)-7-(4-fluorophenyl)pyrazolo[1,5-d][1,2,4]triazine;

3-(2-fluorophenyl)-7-(4-fluorophenyl)-2-(2-propyl-2H-[1,2,4]triazol-3-ylmethoxy)pyrazolo[1,5-d][1,2,4]triazine;

7-(2,6-difluorophenyl)-3-(2-fluorophenyl)-2-(2-methyl-2H-[1,2,4]triazol-3-ylmethoxy)pyrazolo[1,5-d][1,2,4]triazine;

7-(2,6-difluorophenyl)-2-(2-ethyl-2H-[1,2,4]triazol-3-ylmethoxy)-3-(2-fluorophenyl)pyrazolo[1,5-d][1,2,4]triazine;

3-(2-fluorophenyl)-7-(3-fluorophenyl)-2-(2-methyl-2H-[1,2,4]triazol-3-ylmethoxy)pyrazolo[1,5-d][1,2,4]triazine;

7-(2,4-difluorophenyl)-3-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-(pyridin-2-yl)pyrazolo[1,5-d][1,2,4]triazine;

7-(2-fluorophenyl)-2-(2-methyl-2H-[1,2,4]triazol-3-ylmethoxy)-3-(thien-2-yl)pyrazolo[1,5-d][1,2,4]triazine;

7-(2-fluorophenyl)-3-(furan-2-yl)-2-(2-methyl-2H-[1,2,4]triazol-3-ylmethoxy)pyrazolo[1,5-d][1,2,4]triazine;

and salts thereof.

7. The compound of claim 1 which is selected from the group consisting of:

7-(2,4-difluorophenyl)-3-(1,1-dimethylethyl)-2-(2-methyl-2H-[1,2,4]triazol-3-ylmethoxy)pyrazolo[1,5-d][1,2,4]triazine;

7-(2,4-difluorophenyl)-3-(1,1-dimethylethyl)-2-(2-ethyl-2H-[1,2,4]triazol-3-ylmethoxy)pyrazolo[1,5-d][1,2,4]triazine;

2-(2-ethyl-2H-[1,2,4]triazol-3-ylmethoxy)-3,7-bis(2-fluorophenyl)-pyrazolo[1,5-d][1,2,4]triazine;

3,7-bis(2-fluorophenyl)-2-(1-methyl-1H-[1,2,4]triazol-3-ylmethoxy)-pyrazolo[1,5-d][1,2,4]triazine;

3,7-bis(2-fluorophenyl)-2-(3-methyl-3H-[1,2,3]triazol-4-ylmethoxy)-pyrazolo[1,5-d][1,2,4]triazine;

3,7-bis(2-fluorophenyl)-2-(1-methyl-1H-[1,2,3]triazol-4-ylmethoxy)-pyrazolo[1,5-d][1,2,4]triazine;

3,7-bis(2-fluorophenyl)-2-(6-methylpyridin-2-ylmethoxy)pyrazolo[1,5-d][1,2,4]triazine;

3,7-bis(2-fluorophenyl)-2-(pyridin-3-ylmethoxy)pyrazolo[1,5-d][1,2,4]triazine;

3,7-bis(2-fluorophenyl)-2-(pyridin-4-ylmethoxy)pyrazolo[1,5-d][1,2,4]triazine;

2-(3-cyclobutyloxypyridin-2-ylmethoxy)-3,7-bis(2-fluorophenyl)-pyrazolo[1,5-d][1,2,4]triazine;

2-[3,7-bis(2-fluorophenyl)pyrazolo[1,5-d][1,2,4]triazin-2-yloxymethyl]-pyridin-3-yloxyacetonitrile;

3,7-bis(2-fluorophenyl)-2-(3-methoxypyridin-2-ylmethoxy)pyrazolo[1,5-d][1,2,4]triazine;

2-(3-ethoxypyridin-2-ylmethoxy)-3,7-bis(2-fluorophenyl)pyrazolo[1,5-d][1,2,4]triazine;

3,7-bis(2-fluorophenyl)-2-(3-methylpyridin-2-ylmethoxy)pyrazolo[1,5-d][1,2,4]triazine;

N-[3-[3,7-bis(2-fluorophenyl)pyrazolo[1,5-d][1,2,4]triazin-2-yloxymethyl]benzyl]-N,N-dimethylamine;

3,7-bis(2-fluorophenyl)-2-(4-methylthiazol-2-ylmethoxy)pyrazolo[1,5-d][1,2,4]triazine;

3,7-bis(2-fluorophenyl)-2-(5-methylthiazol-2-ylmethoxy)pyrazolo[1,5-d][1,2,4]triazine;

3,7-bis(2-fluorophenyl)-2-(thiazol-4-ylmethoxy)pyrazolo[1,5-d][1,2,4]triazine;

3,7-bis(2-fluorophenyl)-2-(2-isopropyl-2H-[1,2,4]triazol-3-ylmethoxy)-pyrazolo[1,5-d][1,2,4]triazine;

6-[3,7-bis(2-fluorophenyl)pyrazolo[1,5-d][1,2,4]triazin-2-yloxymethyl]-nicotinonitrile;

3,7-bis(2-fluorophenyl)-2-(pyridazin-3-ylmethoxy)pyrazolo[1,5-d][1,2,4]triazine;

3,7-bis(2-fluorophenyl)-2-(pyrazin-2-ylmethoxy)pyrazolo[1,5-d][1,2,4]triazine;

3,7-bis(2-fluorophenyl)-2-(pyrimidin-4-ylmethoxy)pyrazolo[1,5-d][1,2,4]triazine;

3,7-bis(2-fluorophenyl)-2-(quinoxalin-2-ylmethoxy)pyrazol[1,5-d][1,2,4]triazine;

3-(2-fluorophenyl)-7-(furan-3-yl)-2-(2-methyl-2H-[1,2,4]triazol-3-ylmethoxy)pyrazolo[1,5-d][1,2,4]triazine;

3,7-bis(2-fluorophenyl)-2-(1-methyl-1H-benzimidazol-2-ylmethoxy)-pyrazolo[1,5-d][1,2,4]triazine;

3,7-bis(2-fluorophenyl)-2-([1,2,4]triazolo[1,5-a]pyridin-2-ylmethoxy)-pyrazolo[1,5-d][1,2,4]triazine;

3,7-bis(2-fluorophenyl)-2-(5,6,7,8-tetrahydro[1,2,4]triazolo[1,5-a]pyridin-2-ylmethoxy)pyrazolo[1,5-d][1,2,4]triazine;

2-[3,7-bis(2-fluorophenyl)pyrazolo[1,5-d][1,2,4]triazin-2-yloxymethyl]-5,6,7,8-tetrahydro-[1,2,4]triazolo[1,5-a]pyrazine;

2-[2-(2,2-difluoroethyl)-2H-[1,2,4]triazol-3-ylmethoxy]-3,7-bis(2-fluorophenyl)pyrazolo[1,5-d][1,2,4]triazine;

2-[2-(2-fluoroethyl)-2H-[1,2,4]triazol-3-ylmethoxy]-3,7-bis(2-fluorophenyl)pyrazolo[1,5-d][1,2,4]triazine;

7-(2,5-difluorophenyl)-3-(2-fluorophenyl)-2-(2-methyl-2H-[1,2,4]triazol-3-ylmethoxy)pyrazolo[1,5-d][1,2,4]triazine;

7-(2-chlorophenyl)-3-(2-fluorophenyl)-2-(2-methyl 2H-[1,2,4]triazol-3-ylmethoxy)pyrazolo[1,5-d][1,2,4]triazine;

7-cyclopropyl-3-(2-fluorophenyl)-2-(2-methyl-2H-[1,2,4]triazol-3-ylmethoxy)pyrazolo[1,5-d][1,2,4]triazine;

3,7-bis(2-fluorophenyl)-2-(1,5-dimethyl-1H-pyrazol-3-ylmethoxy)-pyrazolo[1,5-d][1,2,4]triazine;

2-(2-ethyl-2H-[1,2,4]triazol-3-ylmethoxy)-7-(2-fluorophenyl)-3-(furan-2-yl)pyrazolo[1,5-d][1,2,4]triazine;

2-(2-ethyl-2H-[1,2,4]triazol-3-ylmethoxy)-7-(2-fluorophenyl)-3-(thien-2-yl)pyrazolo[1,5-d][1,2,4]triazine;

2-(2-ethyl-2H-[1,2,4]triazol-3-ylmethoxy)-7-(2-fluropheny))-3-(thien-3-yl)pyrazolo[1,5-d][1,2,4]triazine;

3-(3-aminophenyl)-7-(2-fluorophenyl)-2-(2-methyl-2H-[1,2,4]triazol-3-ylmethoxy)pyrazolo[1,5-d][1,2,4]triazine;

7-(2-fluorophenyl)-2-(2-methyl-2H-[1,2,4]triazol-3-ylmethoxy)-3-[3-(pyridin-3-yl)phenyl]pyrazolo[1,5-d][1,2,4]triazine;

7-(2-fluorophenyl)-3-iodo-2-(2-methyl-2H-[1,2,4]triazol-3-ylmethoxy)-pyrazolo[1,5-d][1,2,4]triazine;

3-(3-cyanophenyl)-7-(2-fluorophenyl)-2-(2-methyl-2H-[1,2,4]triazol-3-ylmethoxy)pyrazolo[1,5-d][1,2,4]triazine;

and salts thereof.

8. A pharmaceutical composition comprising a compound of formula I as defined in claim 1 or a pharmaceutically acceptable salt thereof in association with a pharmaceutically acceptable carrier.

9. A method for the treatment and/or prevention of anxiety, which comprises administering to a patient in need of such treatment an effective amount of a compound of formula I as defined in claim 1 or a pharmaceutically acceptable salt thereof.

* * * * *